(12) United States Patent
Kaufman et al.

(10) Patent No.: US 9,648,880 B2
(45) Date of Patent: May 16, 2017

(54) ANTIFUNGAL AGENTS AND USES THEREOF

(71) Applicants: University of Massachusetts, Boston, MA (US); Worcester Polytechnic Institute, Worcester, MA (US)

(72) Inventors: Paul Kaufman, Shrewsbury, MA (US); Jessica Lopes Da Rosa-Spiegler, Shrewsbury, MA (US); Reeta Prusty Rao, Shrewsbury, MA (US); Ahmed Fazly, Shrewsbury, MA (US)

(73) Assignees: University of Massachusetts, Boston, MA (US); Worcester Polytechnic Institute, Worcester, MA (US)

( * ) Notice: Subject to any disclaimer, the term of this patent is extended or adjusted under 35 U.S.C. 154(b) by 15 days.

(21) Appl. No.: 14/017,914

(22) Filed: Sep. 4, 2013

(65) Prior Publication Data
US 2014/0142107 A1    May 22, 2014

Related U.S. Application Data

(60) Provisional application No. 61/696,647, filed on Sep. 4, 2012, provisional application No. 61/784,197, filed on Mar. 14, 2013.

(51) Int. Cl.
| | | |
|---|---|---|
| *A01N 43/84* | (2006.01) | |
| *A61K 31/496* | (2006.01) | |
| *A01N 37/22* | (2006.01) | |
| *A01N 43/12* | (2006.01) | |
| *A01N 43/36* | (2006.01) | |
| *A01N 43/42* | (2006.01) | |
| *A01N 43/58* | (2006.01) | |
| *A01N 43/60* | (2006.01) | |
| *A01N 43/713* | (2006.01) | |
| *A61K 31/166* | (2006.01) | |
| *A61K 31/167* | (2006.01) | |
| *A61K 31/381* | (2006.01) | |
| *A61K 31/44* | (2006.01) | |
| *A61K 31/47* | (2006.01) | |
| *A61K 31/495* | (2006.01) | |
| *A61K 31/5025* | (2006.01) | |
| *A61K 31/506* | (2006.01) | |
| *A61K 31/517* | (2006.01) | |
| *A61K 31/519* | (2006.01) | |
| *A61K 31/5375* | (2006.01) | |

(52) U.S. Cl.
CPC ............ *A01N 43/84* (2013.01); *A01N 37/22* (2013.01); *A01N 43/12* (2013.01); *A01N 43/36* (2013.01); *A01N 43/42* (2013.01); *A01N 43/58* (2013.01); *A01N 43/60* (2013.01); *A01N 43/713* (2013.01); *A61K 31/166* (2013.01); *A61K 31/167* (2013.01); *A61K 31/381* (2013.01); *A61K 31/44* (2013.01); *A61K 31/47* (2013.01); *A61K 31/495* (2013.01); *A61K 31/496* (2013.01); *A61K 31/506* (2013.01); *A61K 31/5025* (2013.01); *A61K 31/517* (2013.01); *A61K 31/519* (2013.01); *A61K 31/5375* (2013.01)

(58) Field of Classification Search
None
See application file for complete search history.

(56) References Cited

U.S. PATENT DOCUMENTS

| | | | |
|---|---|---|---|
| 2006/0009806 A1* | 1/2006 | Heruth .................... | A61N 1/05 607/3 |
| 2008/0293699 A1 | 11/2008 | Reed et al. | |

FOREIGN PATENT DOCUMENTS

EP    0 548 798    *    6/1993    ........... C07D 295/18

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface).*
Jordan, V. C. (Nature Reviews: Drug Discovery, 2, 2003, 205-213).*
EP 0 548798, published Jun. 30, 1993.*
International Search Report for International Application No. PCT/US13/57994 mailed Apr. 15, 2014 (4 pages).
Written Opinion of the International Searching Authority for International Application No. PCT/US13/57994 mailed Apr. 15, 2014 (6 pages).
Patel et al., "Synthesis of novel 3-(5-sulfanyl-1,3,4-oxadiazol-2-yl)-2H-chromen-2-one condensed *s*-triazinyl piperazines and piperidines as antimicrobial agents," Med Chem Res. 21:3119-3132 (2012).
Upadhayaya et al., "Optically active antifungal azoles: synthesis and antifungal activity of (2R,3S)-2-(2,4-difluorophenyl)-3-(5-{2-[4-aryl-piperazin-1-yl]-ethyl}-tetrazol-2-yl/1-yl)-1-[1,2,4]-triazol-1-yl-butan-2-ol.," Bioorg Med Chem. 12(9):2225-38 (2004).

* cited by examiner

*Primary Examiner* — Jeffrey S Lundgren
*Assistant Examiner* — William Lee
(74) *Attorney, Agent, or Firm* — Clark & Elbing LLP

(57) ABSTRACT

Antimicrobial agents, compositions that include the agent(s) and use(s) thereof are provided. Also disclosed are screening assays for identifying antimicrobial agents.

24 Claims, 37 Drawing Sheets

Figure 1 (Con't)
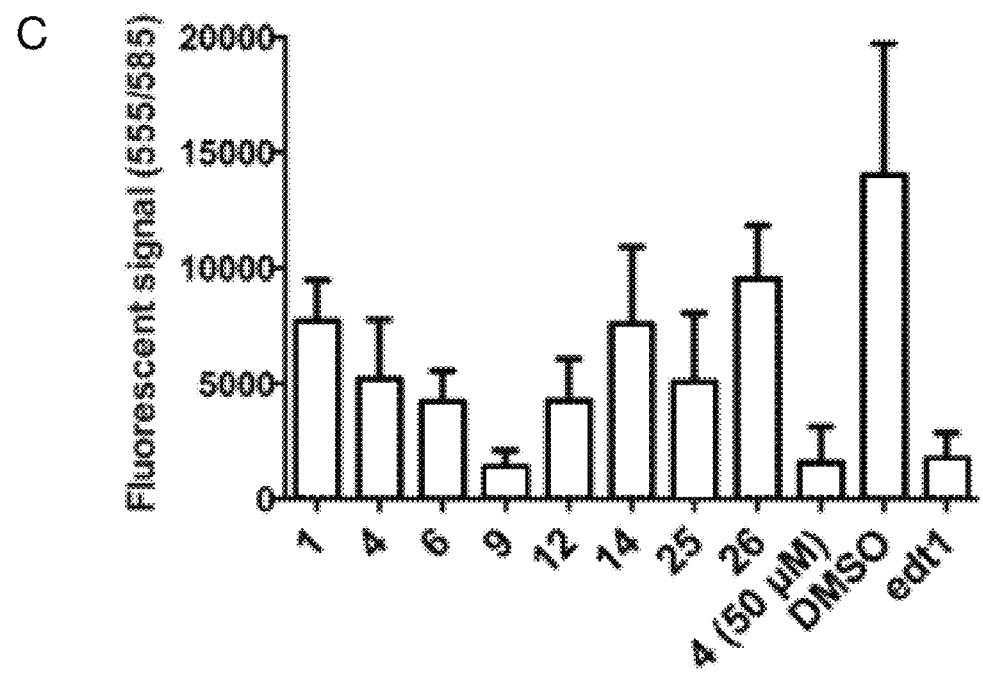
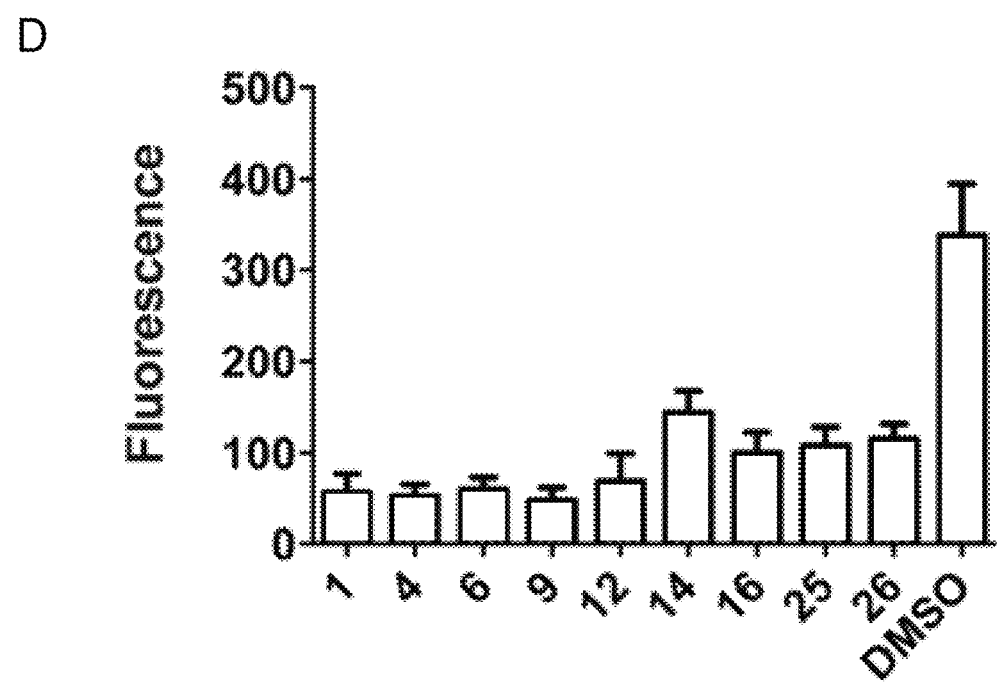

Figure 1 (Con't)
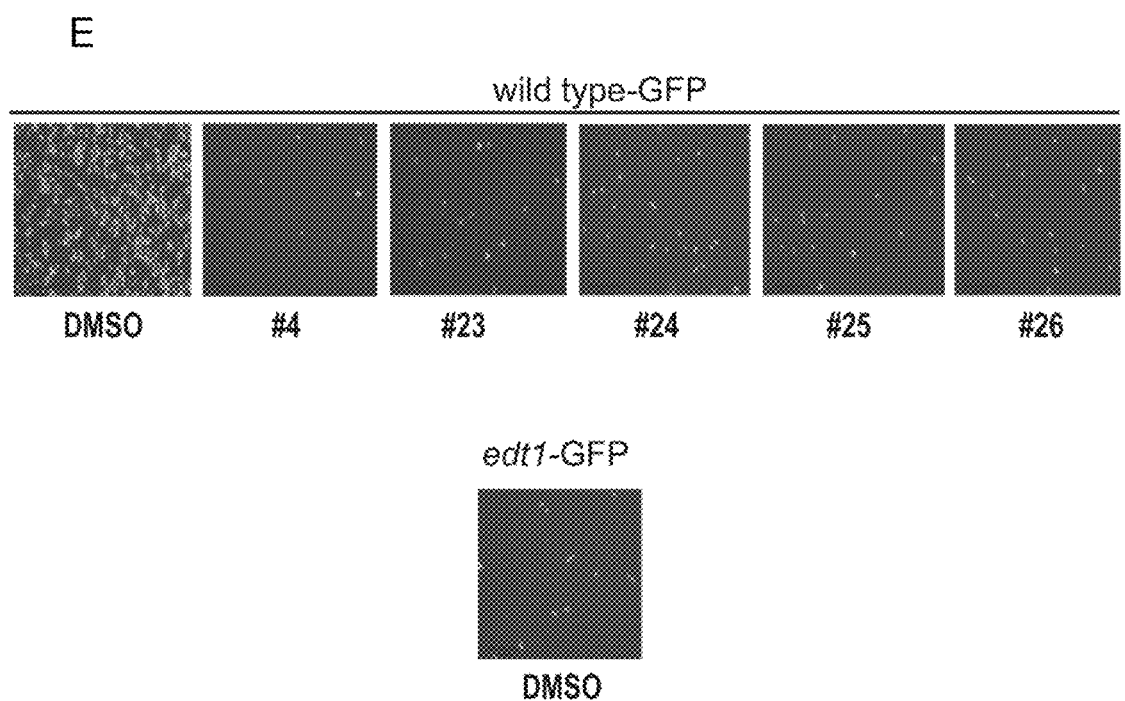

Figure 2 (Con't)
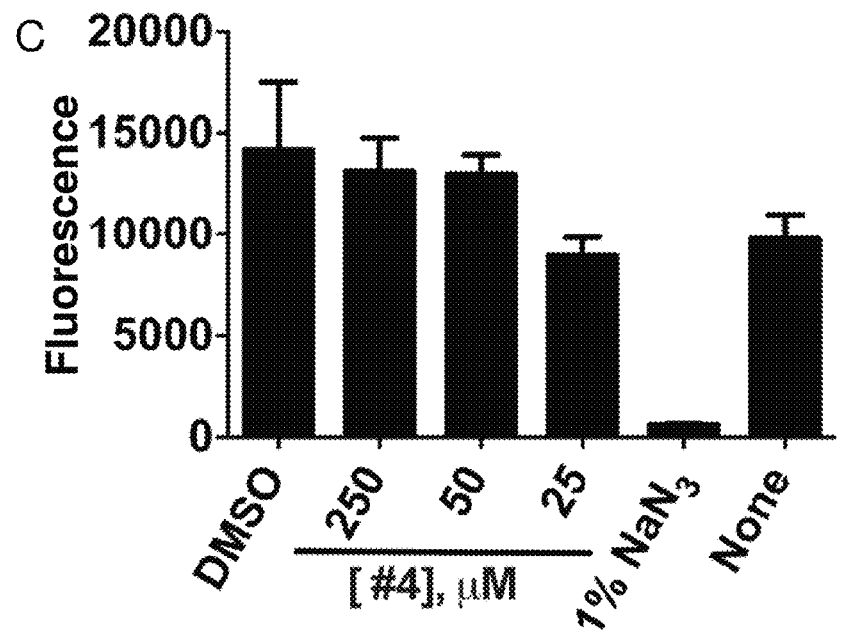
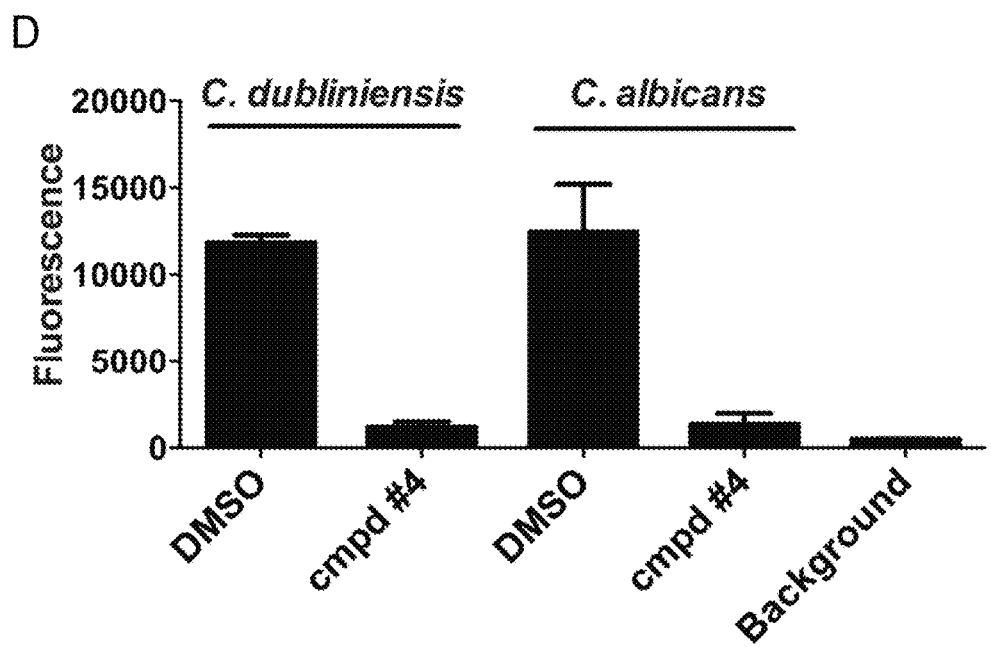

A

Figure 5 (Con't)
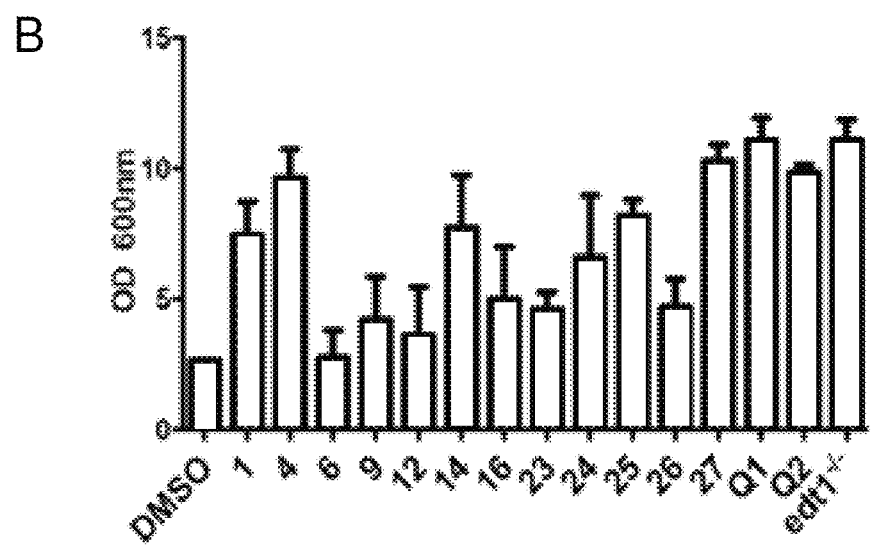
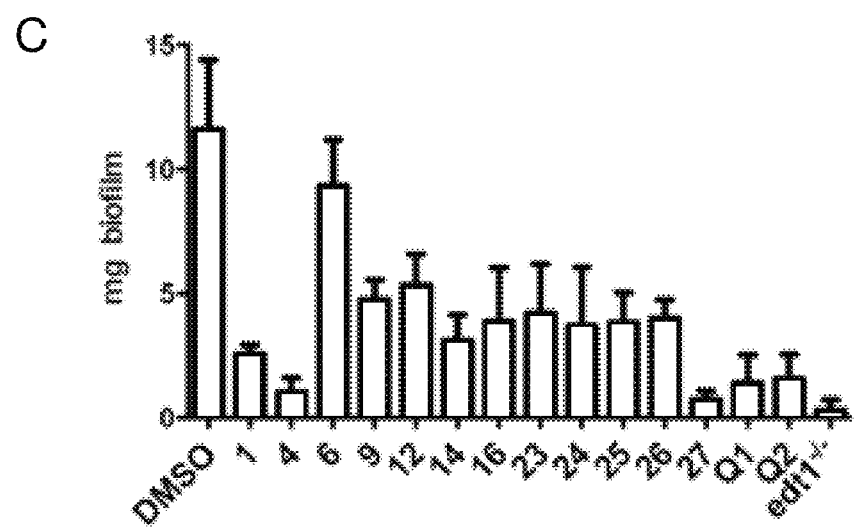

A

Scaffold 1   Compound #4

Scaffold 2   Compound #12

B

Figure 11 (Con't)
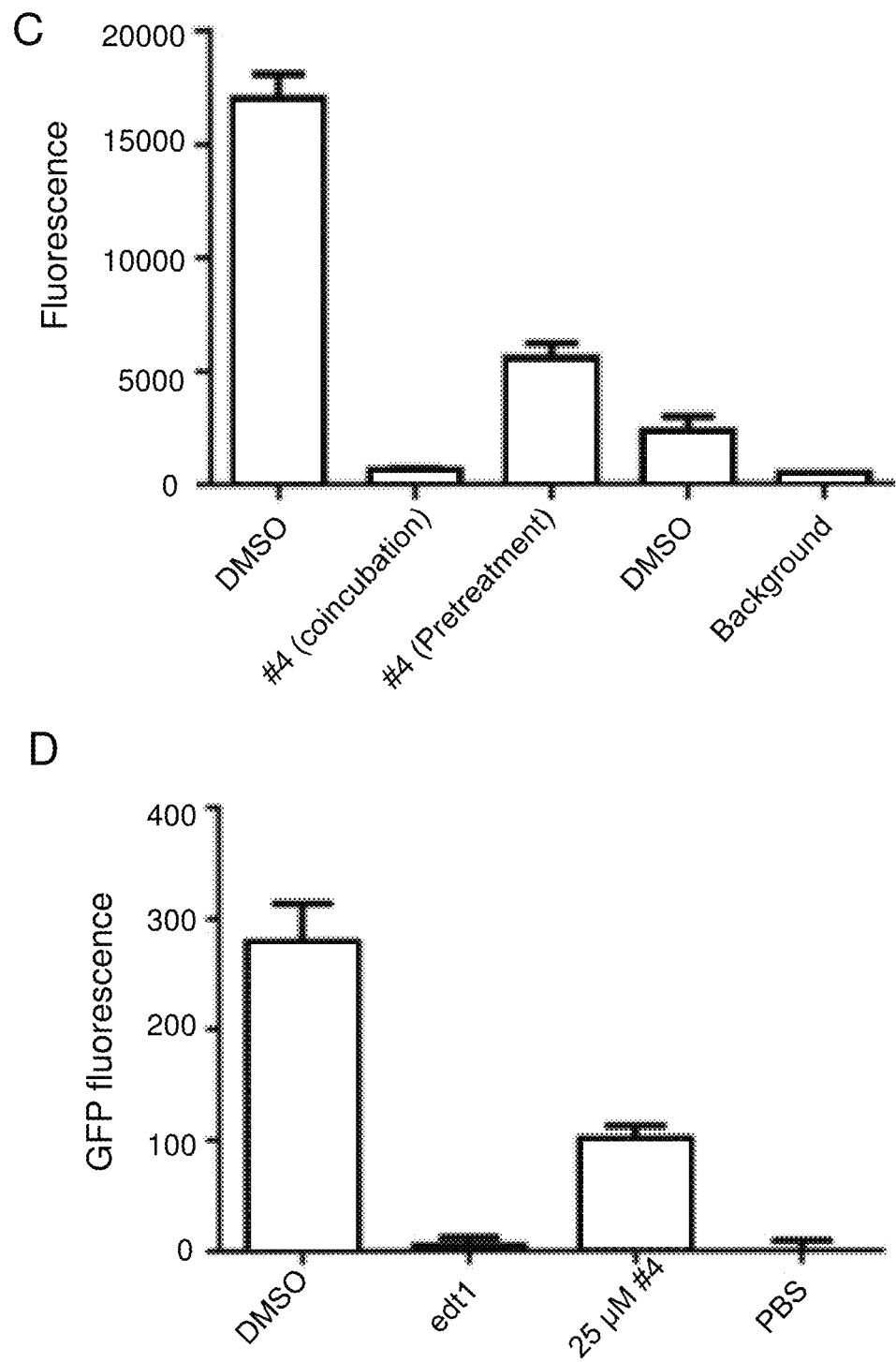

Figure 14 (Con't)
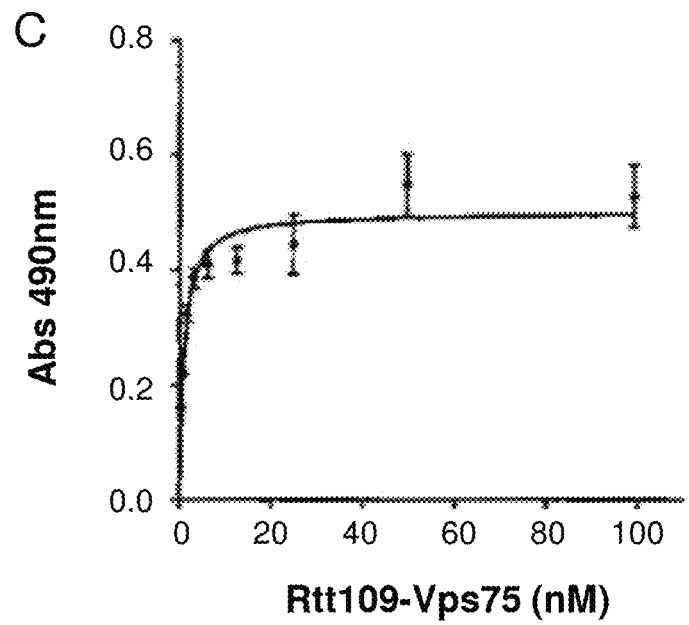
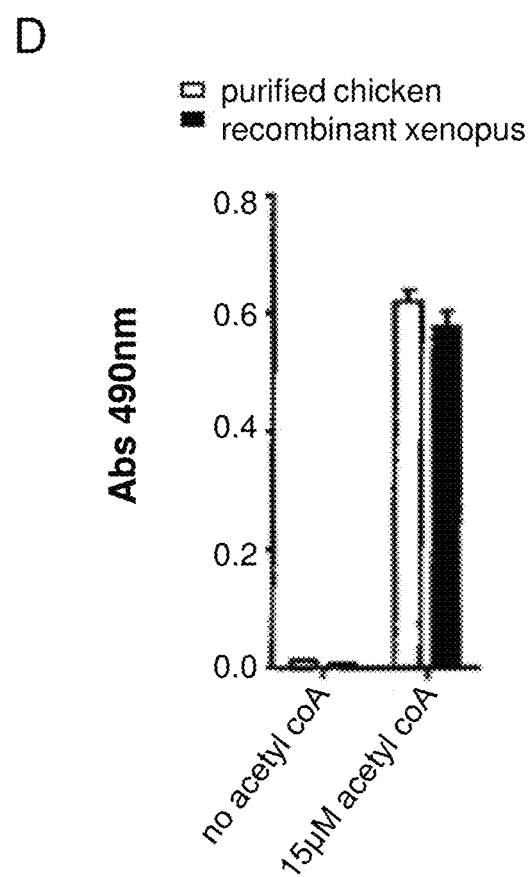

Figure 14 (Con't)
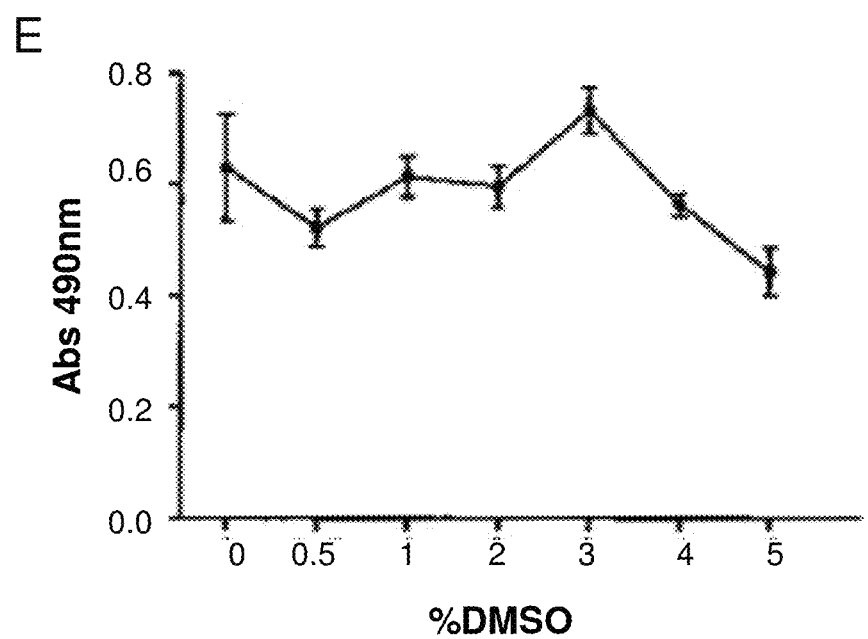
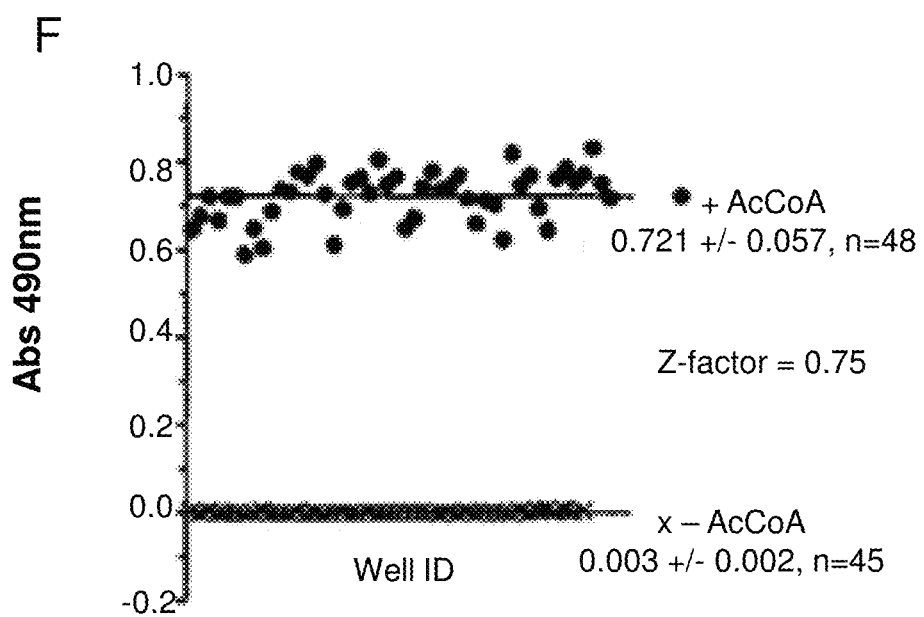

PDK38

PDK23

PDK13

A

B

ANTIFUNGAL AGENTS AND USES THEREOF

STATEMENT AS TO FEDERALLY FUNDED RESEARCH

This invention was made with government support under grant number R01 GM55712, R21 NS066432, F31 AI078726, and P30 AI42845-14 awarded by the NIH. The government has certain rights in this invention.

BACKGROUND OF THE INVENTION

*Candida albicans* is the most widespread fungal pathogen of humans and one of the most frequent hospital-acquired infections (Gudlaugsson, *Clin. Infect. Dis.* 37:1172-1177, 2003; Miller, *Clin. Infect. Dis.* 15:523-530, 2001; Pappas, *Clin. Infect. Dis.* 37:634-643, 2003). The estimated annual cost of treating nosocomial *Candida* infections exceeds $1 billion per year (Miller, supra; Pappas, supra). As an opportunistic pathogen, it is responsible for common clinical problems including, e.g., oral thrush and vaginitis, but can also lead to life-threatening systemic infections (candidiasis) in immunocompromised individuals (Fidel, *Clin. Microbiol. Rev.* 9:335-348, 1996), resulting in 30-50% mortality rates (Gudlaugsson, supra; Rangel-Frausto, *Clin. Infect. Dis.* 29:253-258, 1999). A contributing factor to these statistics is the ability of *C. albicans* to develop resistance to antifungal drugs (Cowen, *Proc. Nat'l. Acad. Sci. U.S.A.* 99:9284-9286, 2002). Moreover, most effective antifungal drugs also cause serious side effects, in many cases because of the significant homology between mammalian and fungal drug targets (Cowen, supra). With such complications, new strategies for combating fungal infections without toxicity to humans are a high medical priority.

Adhesion to surfaces is the first critical step in establishing a fungal infection. *Candida* cells with a planktonic "yeast" morphology initiate adhesion, and a subsequent transition from yeast to hyphal morphology contributes to invasion of the host tissue and formation of biofilms (Bendel, *Crit. Care Med.* 31:501-507, 2003; Saville, *Eukaryot. Cell* 2:1053-1060, 2003; Lo et al., *Cell* 90:939-949, 1997; Finkel, *Nat. Rev. Microbiol.* 9:109-118, 2010). Biofilm formation is a medically crucial step in pathogenesis, because biofilm-associated infections normally do not respond to conventional treatment, and because systemic candidiasis usually results from biofilms originating on intravascular devices and catheters (Douglas, *Trends Microbiol.* 11:30-36, 2003; Blankenship, *Curr. Opin. Microbiol.* 9:588-594, 2006; Nobile et al., *Eukaryot. Cell* 5:1604-1610, 2006). *Candida* cells released from these devices can be disseminated into the bloodstream, where fungal organisms adhere to endothelial surfaces and then penetrate blood vessels, spreading infection to multiple organs. Because biofilm-associated medical devices are resistant to treatment with existing therapeutics, it is often necessary to remove the devices in order to completely treat infections (Bauters, *J. Clin. Microbiol.* 40:1838-1839, 2002).

There still exists a need for effective antifungal agents that can be used to combat fungal infections without toxicity to humans.

SUMMARY OF INVENTION

In a first aspect, the invention features methods of using a compound having a structure according to formula (I),

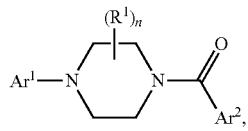

or a stereoisomer thereof, or a salt thereof, wherein n is an integer between 0-4;

each $R^1$, when present, is, independently, OH, halogen, optionally substituted C1-C6 alkyl, or two $R^1$ on the same carbon combine to form an oxo group;

$Ar^1$ is optionally substituted phenyl or optionally substituted monocyclic 5- or 6-membered heteroaryl; and $Ar^2$ is optionally substituted phenyl or optionally substituted heteroaryl.

In some embodiments, n is 1 or 2.

In some embodiments, each $R^1$, when present, is optionally substituted C1-C6 alkyl.

In some embodiments, the compound has a structure according to formula (I-a),

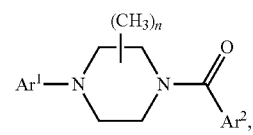

where n is 0 or 1.

In some embodiments, $Ar^1$ is a phenyl that includes 1 or 2 substituents that are electron-withdrawing (e.g., F, Cl, Br, I, CN, or $NO_2$). In certain embodiments, $Ar^1$ is a phenyl having a $NO_2$ substituent. In other embodiments, $Ar^1$ includes 1, 2, or 3 substituents independently selected from halogen and unsubstituted C1-C6 alkyl.

In other embodiments, $Ar^2$ is unsubstituted phenyl.

In some embodiments, $Ar^2$ is optionally substituted benzothiophene or optionally substituted phenyl. In certain embodiments, $Ar^2$ is unsubstituted phenyl or unsubstituted benzothiophene. In other embodiments, $Ar^2$ is phenyl having 1, 2, or 3 substituents selected, independently, from $NO_2$, CN, optionally substituted C1-C6 alkyl, or halogen. In further embodiments, the substituents are, independently, selected from F, Cl, Br, and unsubstituted C1-C6 alkyl.

Exemplary compounds of formula (I) are described in Table 1.

TABLE 1

| No. | Structure |
|---|---|
| 1 | 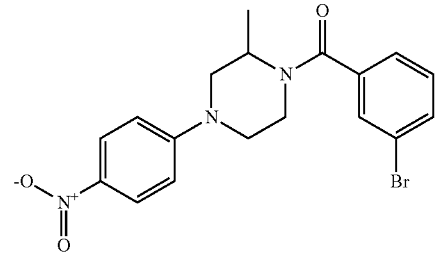 |

TABLE 1-continued

| No. | Structure |
|---|---|
| 2 | 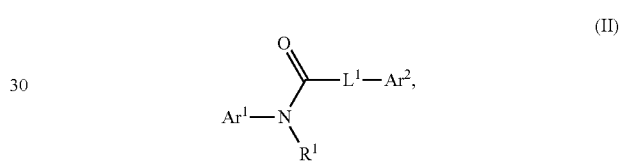 |
| 3 | 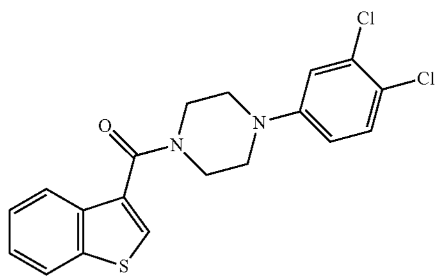 [SMILES: O=C(c1csc2ccccc12)N1CCN(c2ccc(Cl)c(Cl)c2)CC1] |
| 4 | 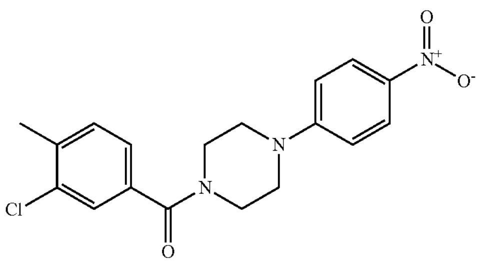 [SMILES: Cc1ccc(C(=O)N2CCN(c3ccc([N+](=O)[O-])cc3)CC2)cc1Cl] |
| 5 | 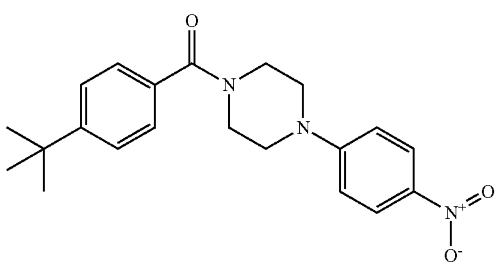 [SMILES: CC(C)(C)c1ccc(C(=O)N2CCN(c3ccc([N+](=O)[O-])cc3)CC2)cc1] |
| 6 | 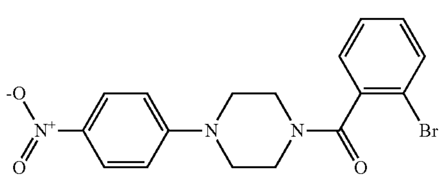 |
| 7 | 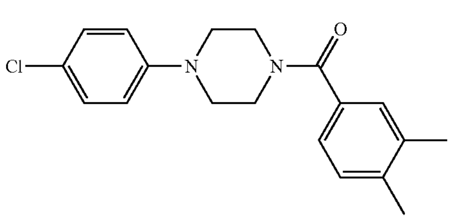 [SMILES: Cc1ccc(C(=O)N2CCN(c3ccc(Cl)cc3)CC2)cc1C] |

TABLE 1-continued

| No. | Structure |
|---|---|
| 8 | 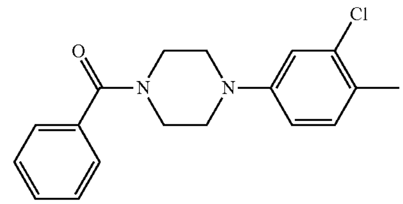 [SMILES: Cc1ccc(N2CCN(C(=O)c3ccccc3)CC2)cc1Cl] |
| 9 | 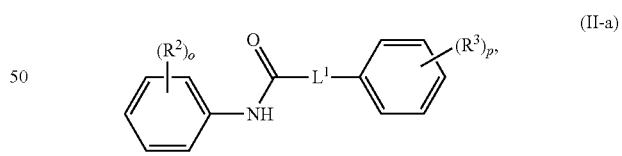 |

In other embodiments, the compound has a structure according to formula (II), $$Ar^1-N(R^1)-C(=O)-L^1-Ar^2 \quad (II)$$

or a salt thereof, wherein
R$^1$ is H or optionally substituted C1-C6 alkyl;
each Ar$^1$ and Ar$^2$ is, independently, an optionally substituted phenyl group; and
L$^1$ is a covalent bond, —O(CH$_2$)$_n$—, or —(CH$_2$)$_n$O—, wherein n is an integer between 0-3.

In some embodiments, R$^1$ is H.
In other embodiments, L$^1$ is a covalent bond, —O(CH$_2$)—, or —(CH$_2$)O—.
In some embodiments, the compound has a structure according to formula (II-a), $$(R^2)_o\text{-Ph-NH-C(=O)-L}^1\text{-Ph-}(R^3)_p \quad (II\text{-}a)$$

wherein
each of o and p is, independently, an integer between 1-3;
each R$^2$ and R$^3$ is, independently, selected from halogen, optionally substituted C1-C6 alkyl, optionally substituted C1-C6 alkoxy; CN, NO$_2$, CO$_2$H, or CO$_2$R$^4$; and
R$^4$ is optionally substituted C1-C6 alkyl or optionally substituted phenyl.

In some embodiments, o is 1 or 2.
In other embodiments, p is 1 or 2.
In still other embodiments, L$^1$ is a bond.
In certain embodiments, each R$^2$ and R$^3$ is selected, independently, from F, Cl, Br, NO$_2$, unsubstituted C1-C6 alkyl, CO$_2$H, and CO$_2$ (unsubstituted C1-C6 alkyl).

Exemplary compounds of formula (II) are described in Table 2.

TABLE 2

| No. | Structure |
|---|---|
| 10 | 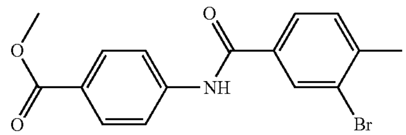 [SMILES: COC(=O)c1ccc(NC(=O)c2ccc(C)c(Br)c2)cc1] |
| 11 | 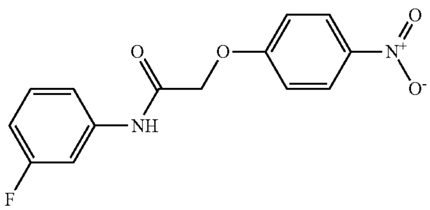 [SMILES: O=C(COc1ccc([N+](=O)[O-])cc1)Nc1cccc(F)c1] |
| 12 | 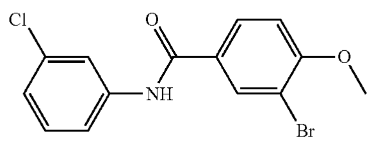 [SMILES: COc1ccc(C(=O)Nc2cccc(Cl)c2)cc1Br] |

In another aspect, the invention features compounds selected from the compounds of Table 3.

TABLE 3

| No. | Structure |
|---|---|
| 13 | 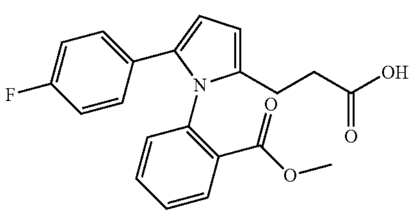 [SMILES: COC(=O)c1ccccc1-n1c(CCC(=O)O)ccc1-c1ccc(F)cc1] |
| 14 | 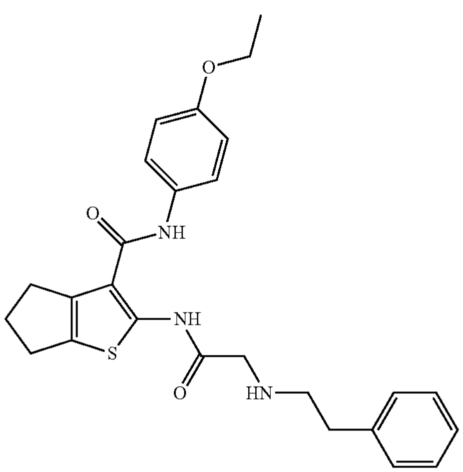 [SMILES: CCOc1ccc(NC(=O)c2c(NC(=O)CNCCc3ccccc3)sc3c2CCC3)cc1] |

TABLE 3-continued

| No. | Structure |
|---|---|
| 15 | 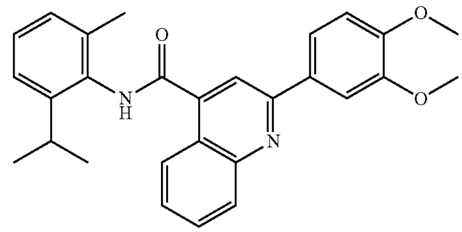 [SMILES: COc1ccc(-c2cc(C(=O)Nc3c(C)cccc3C(C)C)c3ccccc3n2)cc1OC] |
| 16 | 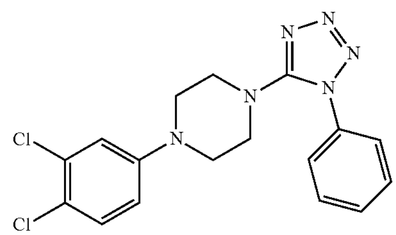 [SMILES: Clc1ccc(N2CCN(c3nnnn3-c3ccccc3)CC2)cc1Cl] |
| 17 | 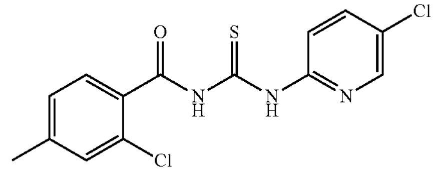 [SMILES: Cc1ccc(C(=O)NC(=S)Nc2ccc(Cl)cn2)c(Cl)c1] |
| 18 | 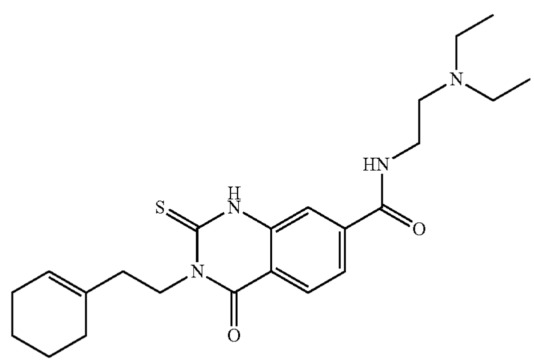 [SMILES: CCN(CC)CCNC(=O)c1ccc2c(=O)n(CCC3=CCCCC3)c(=S)[nH]c2c1] |
| 19 | 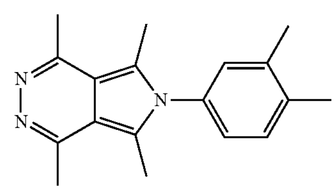 [SMILES: Cc1ccc(-n2c(C)c3c(C)nnc(C)c3c2C)cc1C] |
| 20 | 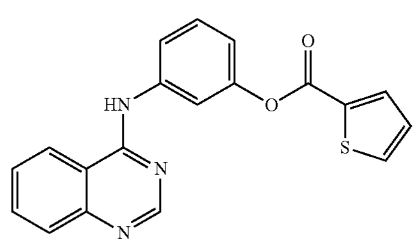 [SMILES: O=C(Oc1cccc(Nc2ncnc3ccccc23)c1)c1cccs1] |

TABLE 3-continued

| No. | Structure |
|-----|-----------|
| 21 | 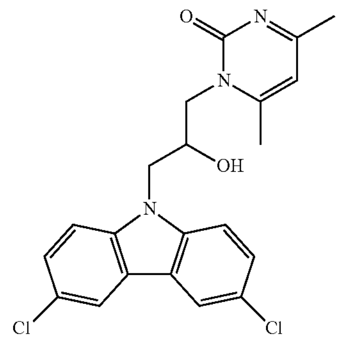 [SMILES: Cc1cc(C)n(CC(O)Cn2c3ccc(Cl)cc3c3cc(Cl)ccc32)c(=O)n1] |
| 22 | 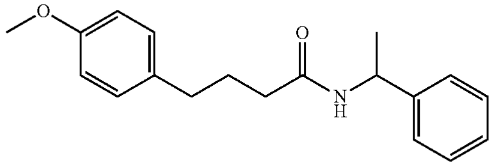 [SMILES: COc1ccc(CCCC(=O)NC(C)c2ccccc2)cc1] |
| 23 | 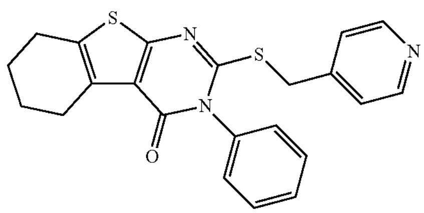 [SMILES: O=c1c2c3c(sc2nc(SCc2ccncc2)n1-c1ccccc1)CCCC3] |
| 24 | 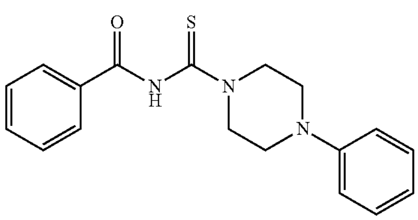 [SMILES: O=C(NC(=S)N1CCN(c2ccccc2)CC1)c1ccccc1] |
| 25 | 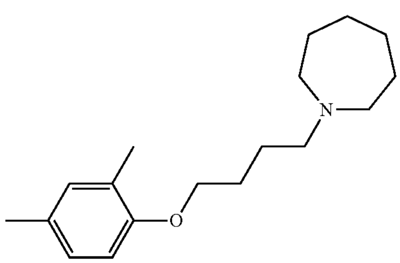 [SMILES: Cc1ccc(OCCCCN2CCCCCC2)c(C)c1] |
| 26 | 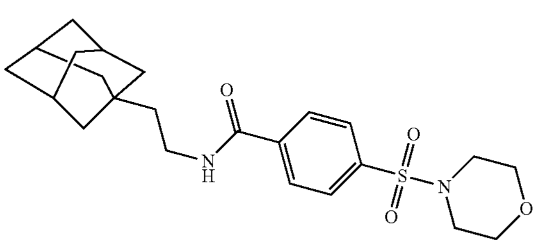 [SMILES: O=C(NCCC12CC3CC(CC(C3)C1)C2)c1ccc(S(=O)(=O)N2CCOCC2)cc1] |

TABLE 3-continued

| No. | Structure |
|-----|-----------|
| 27 | 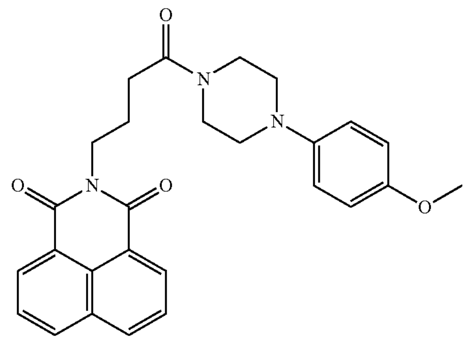 [SMILES: COc1ccc(N2CCN(C(=O)CCCN3C(=O)c4cccc5cccc(c45)C3=O)CC2)cc1] |

In some embodiments, variants of the compounds of Table 3 can be used in the methods described herein. For example, where a compound includes a phenyl group (e.g., any of Compounds (13)-(27)), the phenyl group can be modified to be unsubstituted or to be substituted with 1, 2, 3, 4, or 5 substituents selected, independently, from optionally substituted C1-C6 alkyl, optionally substituted C1-C6 alkoxy, halogen, CN, $NO_2$, $CO_2H$, and $CO_2R^X$, where $R^X$ is an optionally substituted C1-C6 alkyl or an optionally substituted phenyl.

Similarly, compounds of Table 3 that include a heteroaryl group can be modified in order that the heteroaryl group is unsubstituted or substituted with, e.g., 1 or 2 substituents selected, independently, from optionally substituted C1-C6 alkyl, optionally substituted C1-C6 alkoxy, halogen, CN, $NO_2$, $CO_2H$, and $CO_2R^X$, where $R^X$ is an optionally substituted C1-C6 alkyl or an optionally substituted phenyl.

In other embodiments, the length of an alkylene linker in a Table 3 compound (e.g., Compounds (13), (14), (18), (22), (23), and (25)-(27)) can also be varied. For example, the alkylene linker can be varied such that it includes between 1-6 carbons (e.g., a C1-C6 alkylene, a C1-4 alkylene, a C1-2 alkylene, or even a C1 alkylene). Further, the alkylene may be unsubstituted or substituted.

In still other embodiments, carboxylic acid (e.g., $CO_2H$) can be replaced with the corresponding alkyl ester or phenyl ester. Regioisomers or linkage isomers of the compounds of Table 3 can also be used in the methods described herein.

In a second aspect, the invention relates to a method of treating a microbial infection (e.g., a fungal (e.g., an infection caused by a *Candida* spp., such as *C. albicans, C. parapsiliosis, C. krusei, C. tropicalis, C. glabrata, C. parapsilosis, C. lusitaniae, C. kefyr, C. guilliermondii*, and/or *C. dubliniensis*, particularly an infection by *C. albicans*), bacterial, yeast, and/or mold infection) by administering to a subject (e.g., a mammal, such as a human) in need thereof a composition that includes a compound of formula (I):

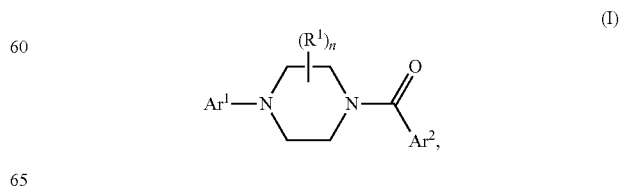

or a stereoisomer thereof, or a salt thereof, wherein
n is an integer between 0-4 (e.g., n is 1 or 2);

each R¹, when present, is, independently, OH, halogen, optionally substituted C1-C6 alkyl, or two R¹ on the same carbon combine to form an oxo group;

Ar¹ is optionally substituted phenyl or optionally substituted monocyclic 5- or 6-membered heteroaryl; and Ar² is optionally substituted phenyl or optionally substituted heteroaryl.

In an embodiment, each R¹, when present, is optionally substituted C1-C6 alkyl. In another embodiment, the compound has a structure according to formula (I-a):

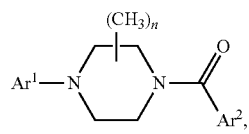

where n is 0 or 1.

In still other embodiments, Ar¹ is a phenyl that includes 1 or 2 substituents that are electron-withdrawing (e.g., F, Cl, Br, I, CN, or NO₂); Ar¹ is a phenyl having a NO₂ substituent; Ar¹ includes 1, 2, or 3 substituents independently selected from halogen and unsubstituted C1-C6 alkyl; Ar² is unsubstituted phenyl; Ar² is optionally substituted benzothiophene or optionally substituted phenyl; Ar² is unsubstituted phenyl or unsubstituted benzothiophene; and/or Ar² is phenyl having 1, 2, or 3 substituents selected, independently, from NO₂, CN, optionally substituted C1-C6 alkyl, or halogen (e.g., the substituents of the phenyl of Ar² are, independently, selected from F, Cl, Br, and unsubstituted C1-C6 alkyl).

In other embodiments of the method, the compound has a structure selected from one of the following:

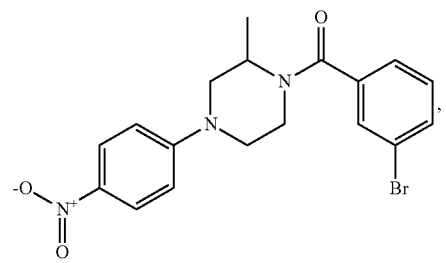

1

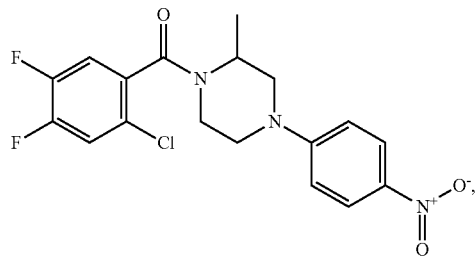

2

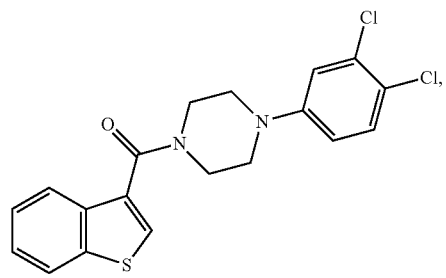

3

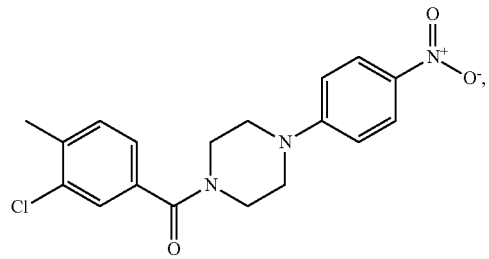

4

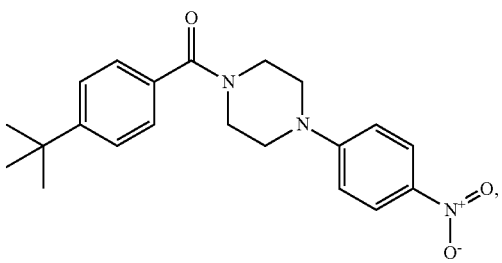

5

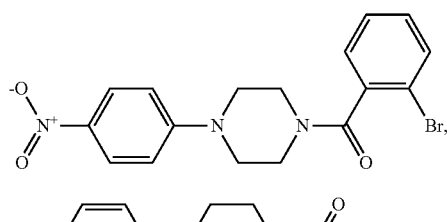

6

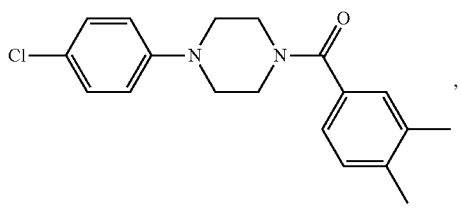

7

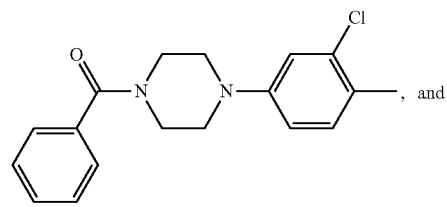

8, and

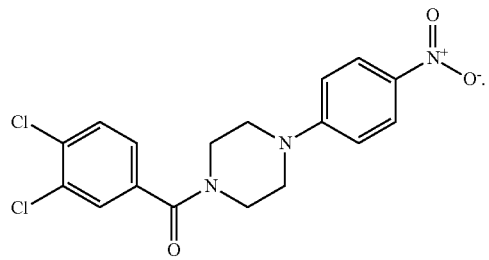

9

The method also includes administering more than one compound of formula I to the subject (e.g., one or more of compounds 1 to 9, in particular, at least compound 4 and one other compound of formula I).

In yet another embodiment of the method, the composition includes a pharmaceutically acceptable carrier. In still other embodiments, treating, according to the method, includes inhibiting and/or reducing (e.g., by at least 10% (e.g., at least 20%, 30%, 40%, 50%, 60%, 70%, 80%, 90%, 95%, or 100%)) at least one function (e.g., adhesion, yeast-to-hyphal morphological transition, biofilm formation, and/or growth) of the microbial agent.

In a third aspect, the invention features a method of treating a microbial infection (e.g., a fungal (e.g., an infection caused by a *Candida* spp., such as *C. albicans, C. parapsiliosis, C. krusei, C. tropicalis, C. glabrata, C. parapsilosis, C. lusitaniae, C. kefyr, C. guilliermondii,* and/or *C. dubliniensis*, particularly an infection by *C. albicans*), bacterial, yeast, and/or mold infection) by administering to a subject (e.g., a mammal, such as a human) in need thereof a composition comprising a compound of formula (II):

$$Ar^1-N(R^1)-C(O)-L^1-Ar^2 \quad (II)$$

or a salt thereof, wherein
$R^1$ is H or optionally substituted C1-C6 alkyl;
each $Ar^1$ and $Ar^2$ is, independently, an optionally substituted phenyl group; and
$L^1$ is a covalent bond, $-O(CH_2)_n-$, or $-(CH_2)_nO-$, wherein n is an integer between 0-3.

In several embodiments, $R^1$ is H; $L^1$ is a covalent bond, $-O(CH_2)-$, or $-(CH_2)O-$; and/or the compound has a structure according to formula (II-a):

$$(R^2)_o\text{-Ph-NH-C(O)-L}^1\text{-Ph-}(R^3)_p \quad (II\text{-a})$$

wherein
each of o and p is, independently, an integer between 1-3;
each $R^2$ and $R^3$ is, independently, selected from halogen, optionally substituted C1-C6 alkyl, optionally substituted C1-C6 alkoxy; CN, $NO_2$, $CO_2H$, or $CO_2R^4$; and
$R^4$ is optionally substituted C1-C6 alkyl or optionally substituted phenyl.

In still other embodiments, o is 1 or 2; p is 1 or 2; $L^1$ is a bond; each $R^2$ and $R^3$ is selected, independently, from F, Cl, Br, $NO_2$, unsubstituted C1-C6 alkyl, $CO_2H$, and $CO_2$ (unsubstituted C1-C6 alkyl); and/or the compound has a structure selected from one of the following:

10

11

12

In yet other embodiments, the method includes administering more than one compound of formula II to said subject (e.g., one or more of compounds 10-12, in particular, at least compound 12 and one other compound of formula II).

In yet another embodiment of the method, the composition includes a pharmaceutically acceptable carrier. In still other embodiments, treating, according to the method, includes inhibiting and/or reducing (e.g., by at least 10% (e.g., at least 20%, 30%, 40%, 50%, 60%, 70%, 80%, 90%, 95%, or 100%)) at least one function (e.g., adhesion, yeast-to-hyphal morphological transition, biofilm formation, and/or growth) of the microbial agent.

In a fourth aspect, the invention features a method of treating a microbial infection (e.g., a fungal (e.g., an infection caused by a *Candida* spp., such as *C. albicans, C. parapsiliosis, C. krusei, C. tropicalis, C. glabrata, C. parapsilosis, C. lusitaniae, C. kefyr, C. guilliermondii,* and/or *C. dubliniensis*, particularly an infection by *C. albicans*), bacterial, yeast, and/or mold infection) by administering to a subject (e.g., a mammal, such as a human) in need thereof a composition having a compound selected from one or more of the following:

13

14

15
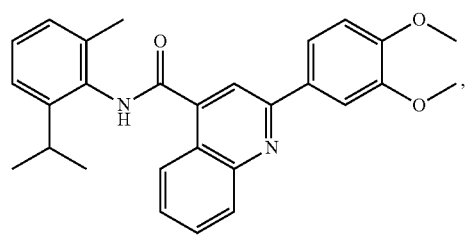
16
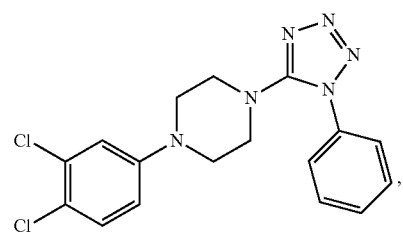
17
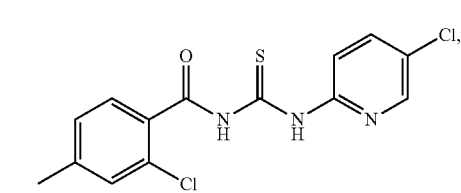
18
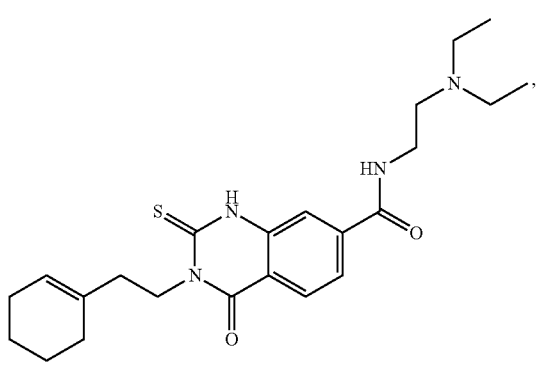
19
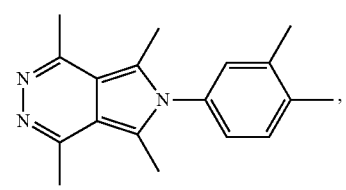
20
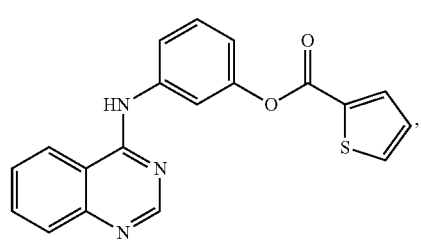
21
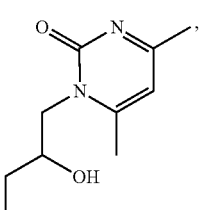
22
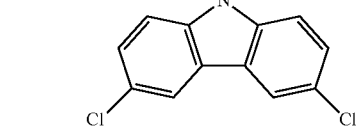
23
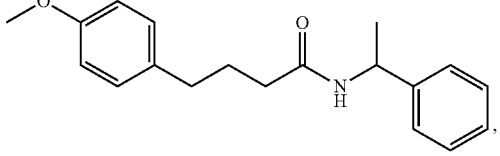
24
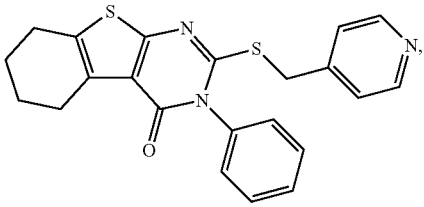
25
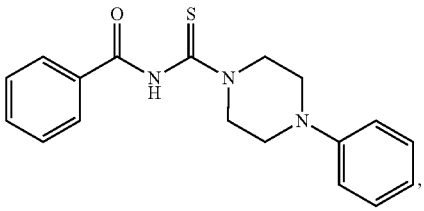
26
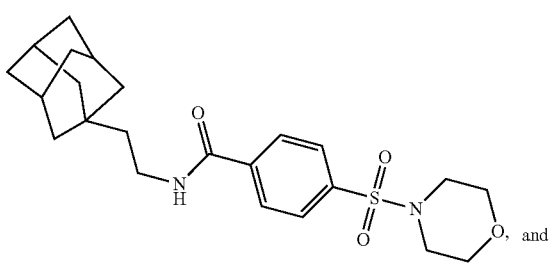
, and

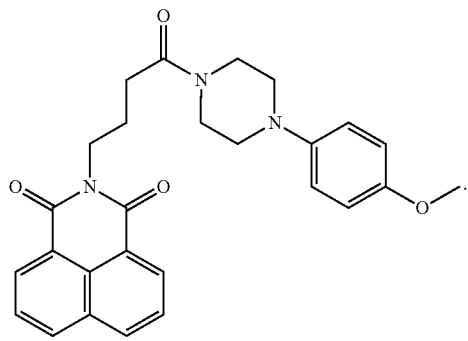

27

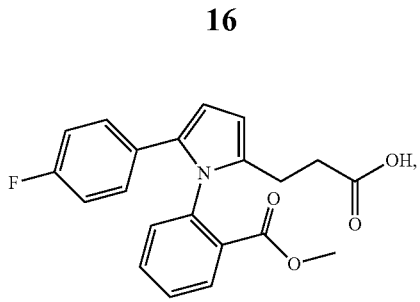

13

In other embodiments, the method includes administering more than one of the compounds (e.g., 13 to 27) to the subject and/or the composition includes a pharmaceutically acceptable carrier. In still other embodiments, treating, according to the method, includes inhibiting and/or reducing (e.g., by at least 10% (e.g., at least 20%, 30%, 40%, 50%, 60%, 70%, 80%, 90%, 95%, or 100%)) at least one function (e.g., adhesion, yeast-to-hyphal morphological transition, biofilm formation, and/or growth) of the microbial agent.

In a fifth aspect, the invention features a composition that includes an anti-microbial compound incorporated therein or coated thereto, in which the compound is selected from one or more of the following:

a) a compound of formula (I):

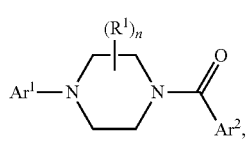

(I)

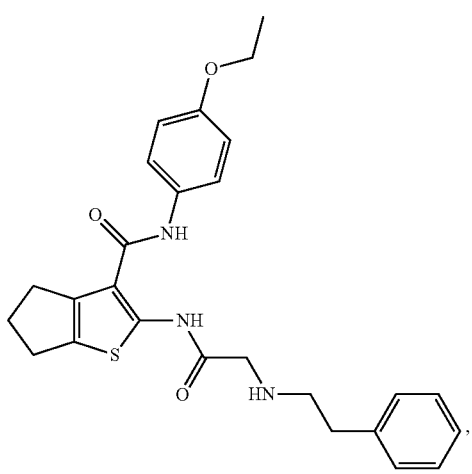

14 or a stereoisomer thereof, or a salt thereof, wherein n is an integer between 0-4;

each $R^1$, when present, is, independently, OH, halogen, optionally substituted C1-C6 alkyl, or two $R^1$ on the same carbon combine to form an oxo group;

$Ar^1$ is optionally substituted phenyl or optionally substituted monocyclic 5- or 6-membered heteroaryl; and $Ar^2$ is optionally substituted phenyl or optionally substituted heteroaryl; and/or b) a compound of formula (II):

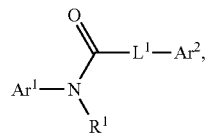

(II)

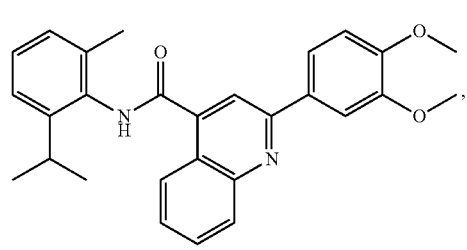

15 or a salt thereof, wherein $R^1$ is H or optionally substituted C1-C6 alkyl;

each $Ar^1$ and $Ar^2$ is, independently, an optionally substituted phenyl group; and $L^1$ is a covalent bond, —O(CH$_2$)$_n$—, or —(CH$_2$)$_n$O—, wherein n is an integer between 0-3; and/or c) a compound selected from one or more of the following:

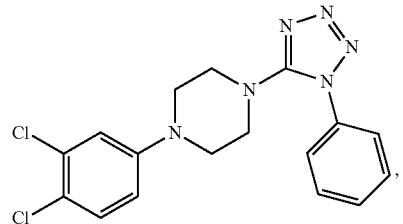

16

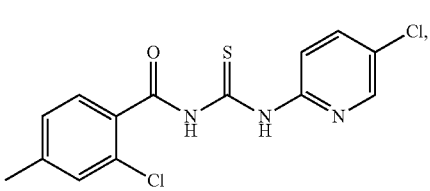

17

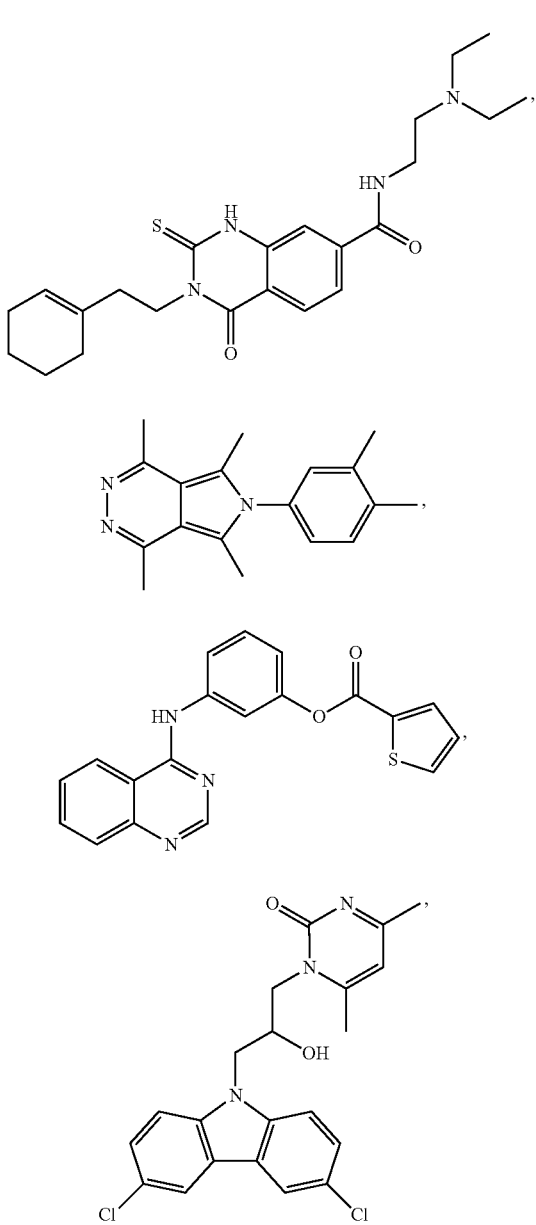
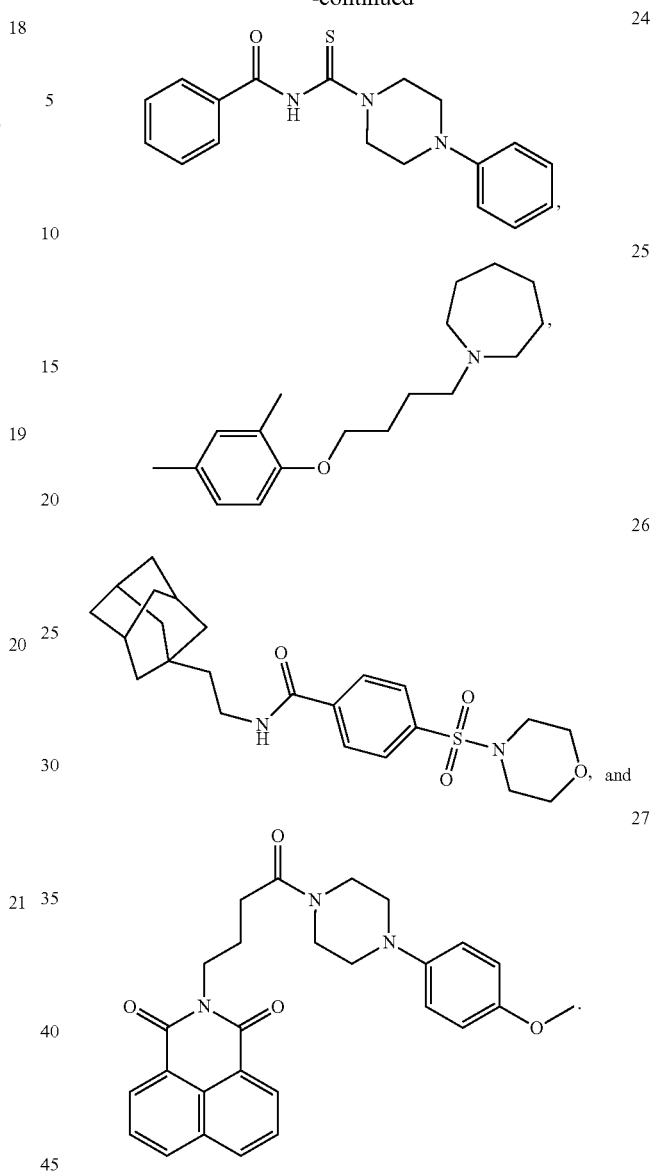

In an embodiment, the compound is

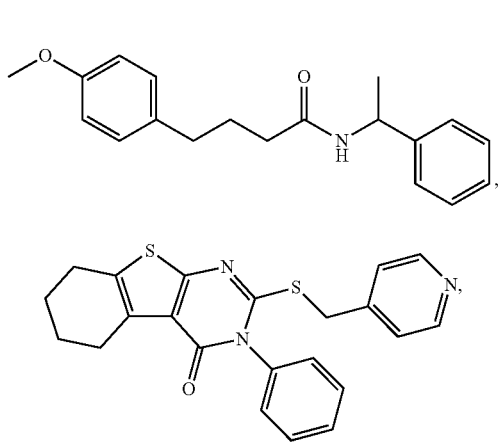

In several other embodiments, the composition is a medical device (e.g., a cardiac-assist device, an artificial heart valve, a catheter, a central line, an intravenous (IV) line, a joint, a stent, a prosthetic implant, a pacemaker, a conduit, a cannula, an appliance, a scaffold, an artificial sphincter, a pessary, a tube, a drain, a trochar or plug, an implant, a rod, a screw, an orthopedic or implantable prosthetic device or appliance, a suture, a drug delivery device, an oral implant, a denture, and/or a brace; and/or a cuff, a dressing material, a mesh, a hernia patch, a wound dressing, a bandage, a syringe, and/or gloves; and/or a household product, a cosmetic product, a pharmaceutical product, a washing or cleaning formulation, a medical device surface, a medical device material, a fabric, a plastic, a surface of a plastic article, a paper, a nonwoven material, a wood, leather, and/or a metal surface). In still other embodiments, the antimicrobial compound reduces and/or inhibits at least one function (e.g., adhesion, yeast-to-hyphal morphological transition, biofilm formation, and/or growth) of a microbial agent (e.g., a fungus (e.g., a *Candida* spp., such as *C. albicans, C. parapsiliosis, C. krusei, C. tropicalis, C. glabrata, C. parapsilosis, C. lusitaniae, C. kefyr, C. guilliermondii*, and/or *C. dubliniensis*, particularly *C. albicans*), a bacteria, yeast, and/or a mold). In still other embodiments, the compound is incorporated into a thermoset, thermoplastic, elastomeric, and/or crosslinked polymer (e.g., a polymer selected from a polyolefin, polyamide, polyurethane, polyacrylate, polyacrylamide, polycarbonate, polystyrene, polyvinyl acetates, polyvinyl alcohol, polyester, halogenated vinyl polymer, such as polyvinyl chloride (PVC), a natural or synthetic rubber, an alkyd resin, an epoxy resin, an unsaturated polyester, an unsaturated polyamide, a polyimide, a silicone, a carbamate containing polymer, a fluorinated polymer, a crosslinkable acrylic resin, such as a substituted acrylic ester, an epoxy acrylate, a urethane acrylate, and/or a polyester acrylate, and/or a block co-polymer thereof). In preferred embodiments, the composition inhibits and/or reduces adhesion of a fungus (e.g., *C. albicans*) to a surface.

In a sixth aspect, the invention relates to a method for achieving an antimicrobial, preservative, and/or microorganism adhesion inhibiting effect for the protection within an article and/or material (e.g., a medical device) or on the surface of an article and/or material (e.g., a medical device) that includes applying the composition described in the fifth aspect, or an adduct or salt thereof, to the article and/or material. In several embodiments, the medical device is a cardiac-assist device, an artificial heart valve, a catheter, a central line, an intravenous (IV) line, a joint, a stent, a prosthetic implant, a pacemaker, a conduit, a cannula, an appliance, a scaffold, an artificial sphincter, a pessary, a tube, a drain, a trochar or plug, an implant, a rod, a screw, an orthopedic or implantable prosthetic device or appliance, a suture, a drug delivery device, an oral implant, a denture, and/or a brace; and/or a cuff, a dressing material, a mesh, a hernia patch, a wound dressing, a bandage, a syringe, and/or gloves; and/or a household product, a cosmetic product, a pharmaceutical product, a washing or cleaning formulation, a medical device surface, a medical device material, a fabric, a plastic, a surface of a plastic article, a paper, a nonwoven material, a wood, leather, and/or a metal surface. In still other embodiments, the compound of the composition reduces and/or inhibits at least one function (e.g., adhesion, yeast-to-hyphal morphological transition, biofilm formation, and/or growth) of a microbial agent (e.g., a fungal (e.g., an infection caused by a *Candida* spp., such as *C. albicans, C. parapsiliosis, C. krusei, C. tropicalis, C. glabrata, C. parapsilosis, C. lusitaniae, C. kefyr, C. guilliermondii*, and/or *C. dubliniensis*, particularly an infection by *C. albicans*), bacterial, yeast, and/or mold infection) by administering to a subject (e.g., a mammal, such as a human). In yet another embodiment, the composition achieves an anti-fungal effect when administered to the subject. In still other embodiments, the compound is incorporated into a thermoset, thermoplastic, elastomeric, and/or crosslinked polymer (e.g., a polymer selected from a polyolefin, polyamide, polyurethane, polyacrylate, polyacrylamide, polycarbonate, polystyrene, polyvinyl acetates, polyvinyl alcohol, polyester, halogenated vinyl polymer, such as polyvinyl chloride (PVC), a natural or synthetic rubber, an alkyd resin, an epoxy resin, an unsaturated polyester, an unsaturated polyamide, a polyimide, a silicone, a carbamate containing polymer, a fluorinated polymer, a crosslinkable acrylic resin, such as a substituted acrylic ester, an epoxy acrylate, a urethane acrylate, and/or a polyester acrylate, and/or a block co-polymer thereof). In still another embodiment, the method includes applying the composition to the surface of the article and/or material.

In a seventh aspect, the invention relates to a method of treating a microbial infection (e.g., a fungal (e.g., an infection caused by a *Candida* spp., such as *C. albicans, C. parapsiliosis, C. krusei, C. tropicalis, C. glabrata, C. parapsilosis, C. lusitaniae, C. kefyr, C. guilliermondii*, and/or *C. dubliniensis*, particularly an infection by *C. albicans*), bacterial, yeast, and/or mold infection) by administering to a subject (e.g., a mammal, such as a human) in need thereof a composition that includes an Rtt109 inhibitor (e.g., one or more of KB7, PDK38, PDK9, PDK23, PDK47, PDK13, PDK17, PDK35, and/or PDK36, in particular KB7, PDK23, and/or PDK13; preferably KB7). In an embodiment, the composition includes a pharmaceutically acceptable carrier. In still other embodiments, treating, according to the method, includes inhibiting and/or reducing (e.g., by at least 10% (e.g., at least 20%, 30%, 40%, 50%, 60%, 70%, 80%, 90%, 95%, or 100%)) at least one function (e.g., adhesion, yeast-to-hyphal morphological transition, biofilm formation, and/or growth) of the microbial agent.

In an eighth aspect, the invention relates to a composition that includes incorporated therein or coated thereto an Rtt109 inhibitor (e.g., one or more of KB7, PDK38, PDK9, PDK23, PDK47, PDK13, PDK17, PDK35, and/or PDK36, in particular KB7, PDK23, and/or PDK13; preferably KB7). In several embodiments, the composition is a medical device (e.g., a cardiac-assist device, an artificial heart valve, a catheter, a central line, an intravenous (IV) line, a joint, a stent, a prosthetic implant, a pacemaker, a conduit, a cannula, an appliance, a scaffold, an artificial sphincter, a pessary, a tube, a drain, a trochar or plug, an implant, a rod, a screw, an orthopedic or implantable prosthetic device or appliance, a suture, a drug delivery device, an oral implant, a denture, and/or a brace; and/or a cuff, a dressing material, a mesh, a hernia patch, a wound dressing, a bandage, a syringe, and/or gloves; and/or a household product, a cosmetic product, a pharmaceutical product, a washing or cleaning formulation, a medical device surface, a medical device material, a fabric, a plastic, a surface of a plastic article, a paper, a nonwoven material, a wood, leather, and/or a metal surface). In still other embodiments, the Rtt109 inhibitor reduces and/or inhibits at least one function (e.g., adhesion, yeast-to-hyphal morphological transition, biofilm formation, and/or growth) of a microbial agent (e.g., a fungus (e.g., a *Candida* spp., such as *C. albicans, C. parapsiliosis, C. krusei, C. tropicalis, C. glabrata, C. parapsilosis, C. lusitaniae, C. kefyr, C. guilliermondii*, and/or *C. dubliniensis*, particularly *C. albicans*), a bacteria, yeast, and/or a mold). In still other embodiments, the Rtt109 inhibitor is incorporated into a thermoset, thermoplastic, elastomeric, and/or crosslinked polymer (e.g., a polymer selected from a polyolefin, polyamide, polyurethane, polyacrylate, polyacrylamide, polycarbonate, polystyrene, polyvinyl acetates, polyvinyl alcohol, polyester, halogenated vinyl polymer, such as polyvinyl chloride (PVC), a natural or synthetic rubber, an alkyd resin, an epoxy resin, an unsaturated polyester, an unsaturated polyamide, a polyimide, a silicone, a carbamate containing polymer, a fluorinated polymer, a crosslinkable acrylic resin, such as a substituted acrylic ester, an epoxy acrylate, a urethane acrylate, and/or a polyester acrylate, and/or a block co-polymer thereof). In preferred embodiments, the Rtt109 inhibitor inhibits and/or reduces adhesion of a fungus (e.g., *C. albicans*) to a surface.

In a ninth aspect, the invention relates to a method for screening a test compound for an antimicrobial, preservative, and/or microorganism adhesion inhibiting effect for the protection within an article and/or material (e.g., a medical device) or on the surface of an article and/or material (e.g., a medical device) and/or for an antimicrobial effect for the treatment of a microbial infection (e.g., a fungal (e.g., an infection caused by a *Candida* spp., such as *C. albicans, C. parapsiliosis, C. krusei, C. tropicalis, C. glabrata, C. parapsilosis, C. lusitaniae, C. kefyr, C. guilliermondii,* and/or *C. dubliniensis*, particularly an infection by *C. albicans*), bacterial, yeast, and/or mold infection) in a subject (e.g., a mammal, such as a human) in need thereof that includes: assaying the test compound using the polystyrene adhesion assay described in, e.g., Example 1 (e.g., as a standard throughput or high throughput assay); assaying the test compound using the crystal violet assay described in, e.g., Example 9; and/or assaying the test compound using the Rtt109 enzymatic assay described in, e.g., Examples 10 and 11; and determining whether the test compound reduces or inhibits at least one function (e.g., adhesion, yeast-to-hyphal morphological transition, biofilm formation, and/or growth) of the microbial agent, e.g., by at least 10% (e.g., at least 20%, 30%, 40%, 50%, 60%, 70%, 80%, 90%, 95%, or 100%), relative to a control. For example, the test compound may reduce or inhibit microbial growth by at least 10% (e.g., at least 20%, 30%, 40%, 50%, 60%, 70%, 80%, 90%, 95%, or 100% (e.g., kills the microbial agent), relative to a control, or acts as a microbistatic or microbicidal agent. In a preferred embodiment, the assay may identify the test compound as an anti-fungal agent that reduces or inhibits fungal growth by at least 10% (e.g., at least 20%, 30%, 40%, 50%, 60%, 70%, 80%, 90%, 95%, or 100% (e.g., kills the fungus), relative to a control, or that acts as a fungistatic or fungicidal agent.

DEFINITIONS

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like Typically, the alkyl, alkenyl and alkynyl groups contain 1-12 carbons (e.g., C1-C12 alkyl) or 2-12 carbons (e.g., C2-C12 alkenyl or C2-C12 alkynyl). In some embodiments, the alkyl groups are C1-C8, C1-C6, C1-C4, C1-C3, or C1-C2 alkyl groups; or C2-C8, C2-C6, C2-C4, or C2-C3 alkenyl or alkynyl groups. Further, any hydrogen atom on one of these groups can be replaced with a substituent as described herein.

As used herein, the terms "alkylene," "alkenylene," and "alkynylene," or the prefix "alk" refer to divalent or trivalent groups having a specified size, typically C1-C2, C1-C3, C1-C4, C1-C6, or C1-C8 for the saturated groups (e.g., alkylene or alk) and C2-C3, C2-C4, C2-C6, or C2-C8 for the unsaturated groups (e.g., alkenylene or alkynylene). They include straight-chain, branched-chain, and cyclic forms as well as combinations of these, containing only C and H when unsubstituted. Because they are divalent, they can link together two parts of a molecule, as exemplified by X in the compounds described herein. Examples are methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a C1 alkylene that is substituted by =O, for example. For example, the term "alkaryl," as used herein, represents an aryl group, as defined herein, attached to the parent molecular group through an alkylene group, as defined herein, and the term "alkheteroaryl" refers to a heteroaryl group, as defined herein, attached to the parent molecular group through an alkylene group, as defined herein. The alkylene and the aryl or heteroaryl group are each optionally substituted as described herein.

The term "alkoxy" represents a chemical substituent of formula —OR, where R is an optionally substituted alkyl group (e.g., C1-C6 alkyl group), unless otherwise specified. In some embodiments, the alkyl group can be substituted, e.g., the alkoxy group can have 1, 2, 3, 4, 5, or 6 substituent groups as defined herein. Similarly, the term "alkaryloxy" represents a chemical substituent of formula —OR, where R is an optionally substituted alkaryl group.

By "anti-fungal agent" or "anti-fungal compound" is meant an agent that reduces or inhibits fungal growth by at least 10% (e.g., at least 20%, 30%, 40%, 50%, 60%, 70%, 80%, 90%, 95%, or 100% (e.g., kills the fungus)). For example, an anti-fungal agent of the invention may be "fungistatic" and/or "fungicidal."

"Pathogenic fungi" include fungi that can cause disease in humans and have two primary morphological appearances. More than 100 species of fungi have pathogenic potential for humans. Their complex cell wall provides a protective covering that have made fungi impervious to many antimicrobial agents. Disease presentation can often be caused by morphological manifestation of fungus. For example, fungal mycelia will develop into fungal "bezoars" that can obstruct, for example, the urinary system. Budding yeast forms can be associated with infection or abscess.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S, and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl, and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, pyridyl, indolyl, pyrimidyl, pyridazinyl, benzothiazolyl or benzimidazolyl, pyrazolyl, imidazolyl, isoxazolyl, thiazolyl, benzothiazolyl, or indolyl. Even more particularly, such moiety is phenyl, pyridyl, or pyrimidyl and even more particularly, it is phenyl.

By "carboxylic acid ester" is meant a group having the structure —CO$_2$R', where R' is selected from H, optionally substituted C$_{1-6}$ alkyl, optionally substituted cycloalkyl, optionally substituted heterocyclyl, optionally substituted aryl, or optionally substituted heteroaryl. When R' is not H, R may be unsubstituted or substituted with, for example, 1, 2, 3, 4, 5, or 6 substituents.

Halo may be any halogen atom, especially F, Cl, Br, or I, and more particularly it is fluoro or chloro.

By "an effective amount" is meant an amount of a compound of the invention that can be used to treat, prevent, delay the onset of, or inhibit the progression of a fungal infection (e.g., use as an anti-fungal agent or compound). The effective amount of an active compound(s) used to practice therapeutic or prophylactic methods of the invention (e.g., to treat, inhibit, or reduce conditions caused by or contributed to by a fungal infection) or for fungistatic or fungicidal methods of the invention varies depending upon the manner of administration, the age, body weight, and general health of the subject or the particular application of the active compound(s) (e.g., as a coating or incorporated into a device or other material of the invention). Those of skill in the art are capable to determining an amount of an active compound of the invention that can be applied as the "effective" amount.

By "fungal infection" or "mycoses" is meant an invasion of a host animal by fungal cells. For example, the infection may include the excessive growth of fungi that are normally present in or on the animal, or growth of fungi that are not normally present in or on the animal. More generally, a fungal infection can be any situation in which the presence of a fungal population is detrimental or damaging to a host animal. As used herein, "fungal infection" includes a primary fungal infection as well as an opportunistic fungal infection.

An "oxo" group is a substituent having the structure C═O, where there is a double bond between a carbon and an oxygen atom.

Typical optional substituents on aromatic or heteroaromatic groups include independently halo (e.g., F, Cl, Br, or I), CN, NO$_2$, CF$_3$, OCF$_3$, COOR', CONR'$_2$, OR', SR', SOR', SO$_2$R', NR'$_2$, NR'(CO)R', NR'C(O)OR', NR'C(O)NR'$_2$, NR'SO$_2$NR'$_2$, or NR'SO$_2$R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl, and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from ═O and ═NOR' where R' is H or an optionally substituted group selected from alkyl, alkenyl, alkynyl, heteroalkyl, heteroalkenyl, heteroalkynyl, heteroaryl, and aryl (all as defined above).

Electron-withdrawing substituents are those substituents that decrease electron density at the site of attachment. Electron-withdrawing substituents typically positive Hammett substituent constants. Exemplary electron-withdrawing substituents include halogen (e.g., F, Cl, Br, or I), NO$_2$, CN, carbonyl groups (e.g., aldehydes, ketones, carboxylic acids, carboxylic esters, and acyl chlorides), haloalkyls, sulfonic acids, sulfonamides, sulfonate esters, and quaternary ammonium salts.

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido (—N$_3$), nitro (—NO$_2$), cyano (—CN), acyloxy(—OC(═O)R'), acyl (—C(═O)R'), alkoxy (—OR'), amido (—NR'C(═O)R" or —C(═O)NRR'), amino (—NRR'), carboxylic acid (—CO$_2$H), carboxylic ester (—CO$_2$R'), carbamoyl (—OC(═O)NR'R" or —NRC(═O)OR'), hydroxy (—OH), isocyano (—NC), sulfonate (—S(═O)$_2$OR), sulfonamide (—S(═O)$_2$NRR' or —NRS(═O)$_2$R'), or sulfonyl (—S(═O)$_2$R), where each R or R' is selected, independently, from H, C1-C6 alkyl or heteroalkyl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

As used herein, the term "subject" can be a human, non-human primate, or other mammal, such as but not limited to dog, cat, horse, cow, pig, turkey, goat, fish, monkey, chicken, rat, mouse, and sheep.

As used herein, the term "treat," "treated," or "treating" when used with respect to a disorder, such as an infectious disease (e.g., a fungal infection) refers to a therapeutic or prophylactic treatment that increases the resistance of a subject to development of the disease (e.g., to infection with a pathogen, such as a fungus) or, in other words, decreases the likelihood that the subject will develop the disease (e.g., become infected with the pathogen), that increases the ability of a subject that has developed disease (e.g., a pathogenic (e.g., fungal) infection) to fight the disease (e.g., reduce or eliminate at least one symptom typically associated with the infection) or prevent the disease from becoming worse, or that decreases, reduces, or inhibits at least one function of the pathogen (e.g., a fungus, such as *Candida albicans*), such as the ability to adhere to a substrate, to form a biofilm, to switch from a yeast to hyphal morphology, to adhere to human cells (e.g., human epithelial cells), and/or to grow by at least 10% (e.g., at least 20%, 30%, 40%, 50%, 60%, 70%, 80%, 90%, 95%, or 100%).

BRIEF DESCRIPTION OF DRAWINGS

FIG. 1A is a photograph showing a crystal violet-stained plate from a small molecule screen. Wild-type C. albicans strain SC5314 or adhesion-defective edt1$^{-/-}$ cells were plated in the presence of 1% DMSO vehicle (positive control) or small molecules at 50 µM, followed by extensive washing to remove unbound cells. Cells that remained were then visualized by staining with crystal violet and quantified by absorbance at 590 nm. Screen details and data normalization are described in the Materials and Methods. FIG. 1B is a graph showing the results of an alamarBlue-based polystyrene adhesion assay with compounds at 25 µM. Using the vital dye alamarBlue as the detection reagent, the 26 primary candidates from the screen were retested at 25 µM, alongside a DMSO positive control. The mean and standard deviation of data from 8 wells were measured. FIG. 1C is a graph showing the results of a retest of polystyrene adhesion assay of FIG. 1B with compounds at 7.5 µM. FIG. 1D is a graph showing the results of a GFP-based adhesion assay. C. albicans strains expressing GFP (SC5314-GFP and edt1$^{-/-}$-GFP) or untagged SC5314 were mixed with compounds at 25 µM or DMSO, and bound to polystyrene plates. Unbound cells were removed by washing. GFP fluorescence was measured, and background fluorescence of wells containing untagged SC5314 was subtracted from signals. Mean and std. dev. for 8 wells are shown. FIG. 1E is a series of photographs showing fluorescence microscopy results of the GFP assay. Wells from the experiment in FIG. 1D were photographed using a 20× objective and FITC filters.

FIG. 2A is a graph showing the results of fluorescence detection of adhesion of multiple Candida species to A549 cells. Human A549 cells were grown to confluence on 48-well plates. SC5314-GFP, edt1$^{-/-}$-GFP or untagged SC5314 were added to triplicate wells and incubated at 37° C. for 90 min with 1% DMSO or 25 µM of the indicated compounds in 1% DMSO. Wells were washed extensively to remove unbound fungi, and GFP fluorescence was measured on a plate reader. FIG. 2B is a series of photographs showing florescence microscopy of C. albicans adhered to A549 monolayers. Representative bright-field (DIC) and corresponding GFP fluorescence images from the experiment in FIG. 2A. FIG. 2C is a graph showing the results of a human cell toxicity assay. A549 cells were coincubated with 1% DMSO, 250, 100, or 50 µM compound #4 or 1% sodium azide for 24 hrs, and cell viability was then measured using alamarBlue. FIG. 2D is a graph showing that adhesion by C. dublinensis is inhibited by compound #4. Adhesion assay as in FIG. 1B, with 25 µM compound #4 tested.

FIG. 3A shows the structures of compounds. #9 was analyzed to determine if the aryl group substitution of compound #4 is important. The piperazinyl quinolone #Q1 was described (Youngsaye, Bio & Med Chem. Ltrs. 21: 5502-5505, 2011) as a compound that reverses fluconazole resistance. Compound #Q2 is a piperazinyl quinolone with the same aryl group substitutions as #4. FIG. 3B is a graph showing that compounds #Q1 and Q2 do not inhibit C. albicans adhesion to polystyrene. Assay performed as in FIG. 1B, with 25 µM compounds. FIG. 3C is a graph showing that compounds #Q1 and Q2 do not inhibit C. albicans adhesion to human A549 cells. Assay performed as in FIG. 2A, with 25 µM compounds.

FIG. 4A is a series of photographs showing microscopic analysis of hyphal development in the presence of the indicated compounds at 12.5 µM. Cells containing an HWP1 promoter-driven RFP reporter were grown in Spider media for 16 hours and photographed using DIC or fluorescence microscopy (RFP) as indicated (64× objective). FIG. 4B is a series of photographs showing the dose-dependent effects of compound #4, 12 and Q1 on hyphal development. Compounds at 10, 5, 2.5 µM as indicated were tested as above.

FIG. 5A is a series of photographs showing biofilm formation on silicone elastomers. Biofilm assay was performed with SC5314-GFP and edt1$^{\Delta/\Delta}$-GFP and photographed after 60 hrs. Indicated compounds were added at 50 µM. Turbid medium indicates planktonic cells unattached to silicone elastomers when biofilm formation is inhibited. Clear medium with the cell attached to the silicone elastomer indicate establishment of functional biofilm. Each treatment was done in triplicate. FIG. 5B is a graph showing quantitation of turbidity of medium. Media was removed from the wells, vortexed vigorously and the OD at 600 nm was measured in a spectrophotometer. FIG. 5C is a graph showing quantitation of dry weight of biofilm. Dry weight in mg of air-dried silicone elastomers.

FIG. 6A is a graph showing the lifespan of C. elegans exposed to C. albicans treated with 12.5 µM compound #4 (lower graph line) or 12.5 µM fluconazole (upper graph line) compared to untreated (middle graph line). Worms treated with compound #4 display significantly increased survival compared to untreated worms (p<0.012 for drug treated worms compared to untreated). FIG. 6B is a series of photographs showing microscopic analysis of ex vivo vaginal mucosal biofilm formation. Mice were administered estrogen and vaginae were harvested. Tissues were either uninfected, or pretreated with DMSO or 50 µM compound #4, and then inoculated with C. albicans SC5314 ($10^6$ blastoconidia) and incubated for 24 h. Tissues were bisected and processed for scanning electron microscopy (SEM), or confocal microscopy (CM) after staining with Calcofluor to detect yeast (blue) and Concavalin A to visualize extracellular matrix (red). SEM images were taken at 1000× magnification, and CM images at 600× magnification. The figure shows representative images of areas of biofilm growth from two independent repeats, n=6 vaginal explants per experiment.

FIG. 7 is a graph showing Z'-factor measurement for Alamar Blue-based adhesion assay. Overnight cultures of SC5314 cells were diluted to 0.5 OD/ml in fresh SCM and plated onto an Immulon 2HB 96 well microtiter plate. 48 wells were treated with either 1% DMSO or 25 µM compound #4, and alamarBlue-based adhesion assays were performed as described in the Methods. Z' factor was calculated as described (Zhang et al., J. Biomol. Screen 4:67-73, 1999).

FIG. 8A is a graphs showing the IC50 for compound #4 measured using GFP adhesion assay. Assay performed as in FIG. 1D with the indicated concentrations of compound #4. Mean and standard deviations from 4 replicate well measurements are shown. FIG. 8B is a graph showing the effect of compound #4 on growth rate of SC5314 in liquid culture. SC5314 was grown in liquid YPD in a 30° C. shaker in the presence of 1% DMSO or compounds #4, 5, 6, 7 or 8 at 50 µM and the $OD_{600}$ of the culture was measured at the indicated times. Cultures were also observed in the microscope, and we confirmed that the cells retained the budding yeast morphology during the course of this experiment.

FIG. 9A shows the chemical structures of the two scaffold groups identified. FIG. 9B is a graph showing that scaffold 1 compound #4 does not synergize with scaffold 2 compound #12 in inhibiting adhesion to polystyrene. Assay performed as in FIG. 1B, with the indicated compound concentrations.

FIGS. 10A-10B. FIGS. 10A and 10B are graphs showing that, unlike compound #Q1, compound #4 does not synergize with low concentrations fluconazole to inhibit growth of clinical Candida strains. Candida strains were identified from AIDS patients (3919, an initial progenitor isolate, and the subsequently isolated 4617 and 4639 strains). These were coincubated in the presence of either compounds #4, #Q1, fluconazole alone or a combination of fluconazole with either #4 or #Q1 for 24 hrs in polystyrene plates at 37° C. Viability was assessed using alamarBlue reagent as described (Youngsaye, supra). FIG. 10A shows the results using strain 4617, while FIG. 10B shows the results using strain 4639.

FIG. 4A is a graph showing the results of pretreatment of polystyrene with candidate compounds. Indicated compounds at 50 µM were incubated in polystyrene 96-well plates overnight. Wells were washed three times with 100 µl of PBS. C. albicans adhesion was then measured using the vital dye alamarBlue, with no additional drug treatment. FIG. 11B is a graph showing titration of compounds #1, 4 and 9 for pre-binding to polystyrene. Indicated concentrations of compounds were pre-incubated with polystyrene plates as above prior to the adhesion assays. FIG. 11C is a graph showing the inhibition of adhesion by pretreatment of C. albicans SC5314 cells with compound #4 prior to introduction to plastic. SC5314 cells were treated with 25 µM compound #4 or DMSO in liquid culture prior to their introduced into polystyrene plates. Cells were washed with PBS prior to resuspension into SCM and seeding into 96-well plates for adhesion assays using alamarBlue detection of remaining cells. The pretreated cells were assayed alongside a standard adhesion assay in which compound #4 and the cells were coincubated with the plastic simultaneously. FIG. 11D is a graph showing the results of an assay performed as in FIG. 11C, except that SC5314-GFP cells were used, and then detected via fluorescence measurement. edt1 indicates non-adherent mutant cells, PBS indicates background fluorescence in absence of cells.

FIG. 13 are photographs showing two different 96-well plates from the screen. The left-hand columns on each plate marked "edt1$^{-/-}$" contained mutant C. albicans cells lacking the Edt1 protein required for efficient adhesion to surfaces, and serve as negative controls. The right-hand columns marked "DMSO" contained wild-type C. albicans cells and serve as positive controls. The wells in the middle 10 columns had compounds from the library added. Note that some display greatly reduced adhesion (arrows—Wells D8 and H9); these represent our primary candidates of interest. We have also observed many compounds that appear to promote adhesion (arrows—Wells E3 and H10); the high frequency of this class suggests these may result from non-specific aggregation effects of hydrophobic compounds.

FIG. 14A is a photograph showing recombinant Rtt109 and Vps75, either produced as single proteins (lanes 1 and 2) or as a complex in bacteria. FIG. 14B is a photograph showing 10 µg total nuclear protein from either wild-type or asf1 cells analyzed by immunoblotting with anti-H3K56ac rabbit sera. "H3" indicates full length H3, which is acetylated on K56 in the wt strain, and "H3Δ" indicates a proteolytic product. "*" indicates a cross-reactive species indicating equal loading of the two lanes. FIG. 14C is a graph showing enzymatic detection of H3K56 ac in a 96 well plate, in the presence of the indicated amounts of enzyme. FIG. 14D is a graph comparing histone sources and measuring the background observed in the absence of added acetyl CoA, as in FIG. 14C. FIG. 14E is a graph showing DMSO sensitivity of the assay. FIG. 14F is a preliminary Z-factor score in the 96-well format, with 200 ng H3/H4 and 40 ng Rtt109/Vps75 per assay.

FIG. 17 is a graph showing the Z-score in the 384-well format. A 384-well plate of acetylation reactions was analyzed using the indicated conditions, with half of the reactions containing and half lacking acetyl-CoA. The Z-factor in this experiment was 0.85.

FIG. 18 is a graph showing the results of a screen plate of 384 assays. The plate included positive and negative control wells (+ and − AcCoA, respectively); the Z-score for the control wells on this plate was 0.90. Triangles represent tests of library compounds. Note that two compounds inhibited the assay below the pictured 75% inhibition cutoff line.

FIG. 19 is a graphs showing candidate compound titration in assays with Rtt109-Vps75. Acetylation relative to a vehicle only positive control for triplicate assays is shown.

FIG. 21 is a graph showing candidate compound titration in assays with Rtt109+Asf1/H3/H4. Acetylation relative to a vehicle-only positive control for triplicate assays is shown.

FIG. 22 shows the structures of candidate anti-fungal compounds.

FIG. 23 is a graph showing the results of a fluorescence-based assay for histone acetylation by Rtt109+Vps75. Data from triplicate assays are shown performed under the same reaction conditions (187 nM H3/H4) as used in the ELISA.

FIG. 24A shows the structure of a candidate anti-fungal compound ("KB7"). FIG. 24B is a graph showing the IC50 curve for Rtt109-Vps75 catalysis. 50 nM Rtt109-Vps75 and 15 µM H3n21 peptide were incubated with DMSO (vehicle) or KB7 at the indicated concentrations for 5 minutes at 30° C. HAT reactions were initiated with 30

µM Acetyl coEnzyme A. Release of coEnzyme A was detected at various time points for 10 minutes to quantify reaction rates. Non-linear curve fit indicates an IC50 value of 55.18 nM, $R^2$=0.94. FIG. 24C is a graph showing HAT activity of P300 and Gcn5 at the indicated KB7 concentrations. HAT reactions were performed as described above with 15 µg/ml P300 or Gcn5.

FIG. 25A is a graph showing that acetylation of H3K56 is inhibited by KB7. End-point HAT reactions were performed with 50 nM Rtt109, 300 µM (H3-H4)$_2$ tetramers, 50 nM Vps75 or 400 nM Asf1n at 30° C. for 30 minutes. Reactions were incubated with DMSO (vehicle) or 500 nM KB7 for 5 minutes prior to initiation with 15 µM acetyl coEnzyme A. Acetylated H3K56 was detected by ELISA using a specific rabbit anti-serum. n=2. FIG. 25B is a graph showing that HAT activity of P300 is not inhibited by KB7. End-point reactions were also monitored for 15 µg/ml P300 as described in FIG. 25A. Acetylated histone H4 was monitored by ELISA using a polyclonal anti-acetyl H4 antibody. n=1.

FIGS. 26A-26B are photographs showing that hyphal development occurs normally in RPMI tissue culture media in the absence of treatment (FIG. 26A) and in the presence of 1% DMSO (control; FIG. 26B). *Aspergillus* hyphal development was inhibited in the presence of 50 µM and 100 µM compound #4 (FIGS. 26C and 26D, respectively).

FIGS. 27A and 27B are graphs showing that the growth of *Cryptococcus gatti* was inhibited by 50 µM and 100 µM compound #4 growth, whereas no effect on growth was observed in the untreated (control) and 1% DMSO treated samples.

FIGS. 28A and 28B show the time course of hyphal development of *C. albicans* ells grown in Spider media for the indicated periods of time in the presence of DMSO (control; FIG. 28A) or Compound #4 (FIG. 28B).

FIG. 29A is a series of photomicrographs showing the effect of compound #4 on SC5314 cells grown at 37° C. for the indicated time in Spider media or supplemented YNB+10% bovine serum. DMSO is a control. FIG. 29B shows the effect of compound #4 on colonly morphology of *C. albicans* SC5314 cells. Solid Spider media agar plates were overlayed with either 1% DMSO or 50 □M #4. *C. albicans* SC5314 cells were spotted onto these plates and incubated at 37° C. for 2 days before photography. The upper images were taken with a digital camera; single colonies below were imaged using a microscope with 12.5× magnification.

FIG. 30A is a schematic diagram of some of the signaling pathways that govern hyphal gene expression. For simplicity, only those genes investigated in this figure are shown. FIG. 30B is a series of photomicrographs showing the effects of compound #4 on constitutively filamentous mutant strains in the cAMP-PKA pathway. Wild-type SC5314, efg1-T206E, ras1-G13V, and ADH1pr-gpa2-Q355L cells were grown in the presence of 1% DMSO or 50 µM compound #4 in Spider medium at 37° C. for 4 hrs, stained with Calcofluor white and photographed using DIC or fluorescent microscopy (20× objective). FIG.

30C is a series of two photomicrographs showing that Compound #4 blocks filamentation induced by GlcNAc or constitutive overexpression of the GlcNac-activated transcription factor Cph1. Images obtained as in FIG. 30B. FIG. 30D is a series of photomicrographs showing that Compound #4 does not block genotoxic stress-induced filamentation. SC5314 cells grown in YPD at 30° C. in the presence of 50 mM hydroxyurea (HU) in combination with either 1% DMSO or 50 mM compound #4. Images obtained as in FIG. 30B. FIG. 30E is a series of photomicrographs showing that Compound #4 inhibits the hyperfilamentous growth of a strain that constitutively overexpresses the Gpr1 protein. Colonies were grown on solid Spider media agar overlayed with either 1% DMSO or 50 µM #4 and incubated at 37° C. for 3 days. Colony edges were imaged with a 10× objective.

DETAILED DESCRIPTION

Figure 1:
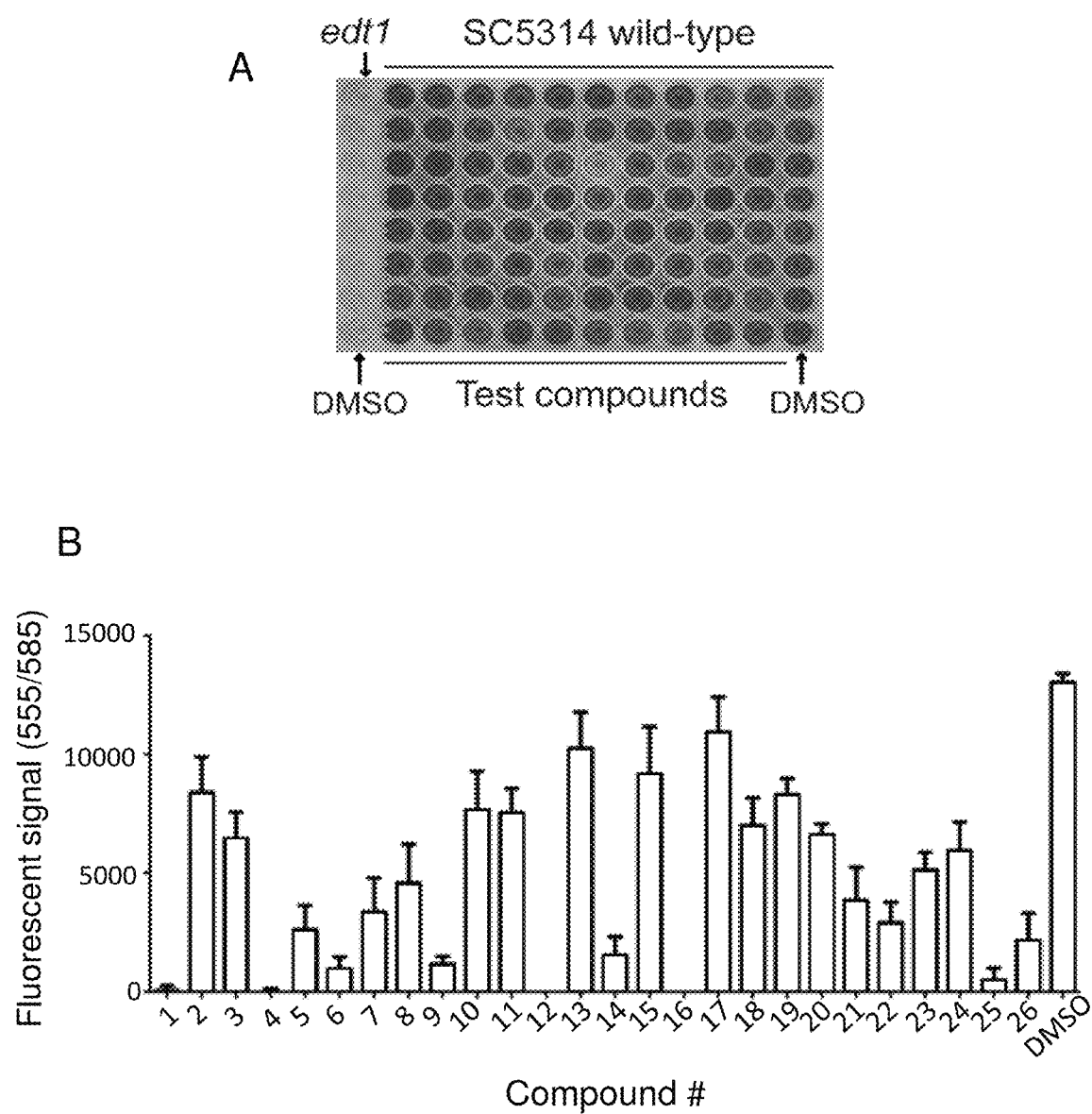
FIGS. 1A-1E. Chemical inhibition of *Candida albicans* adhesion to polystyrene.

Pathogenesis by fungi, such as *Candida albicans*, begins with adhesion to host cells or implanted medical devices, followed by biofilm formation. We have developed assays to identify small molecules and other agents that inhibit adhesion of *C. albicans* to surfaces, such as polystyrene surfaces. Compounds we have identified using these assays also inhibit binding of *C. albicans* to cultured human epithelial cells, the yeast-to-hyphal morphological transition, biofilm formation on silicone mesh, and pathogenesis in a nematode infection model, and thee also alter fungal morphology in a mouse mucosal infection assay. Other compounds identified herein share some but not all of these activities. Therefore, we have identified compounds that can address various aspects of fungal pathogenesis, and that can be used as novel antifungal agents.

We report here development of assays for the identification of compounds that prevent adhesion of *C. albicans* to polystyrene surfaces. In secondary assays, we discovered one compound (compound #4, Table 1) that inhibits adhesion not only to polystyrene, but also to human cells. Furthermore, this compound inhibits the *C. albicans* yeast-to-hyphal morphological switch, impairs biofilm formation on silicone mesh, reduces fungal pathogenesis in a nematode infection model, and alters biofilm morphology in a mouse mucosal infection model.

Compositions of the Invention

The present invention provides compounds that are antimicrobial agents (e.g., anti-fungal agents) that can be used in the treatment or prophylaxis of a subject (e.g., a human) and in the treatment of surfaces and/or devices (e.g., medical devices). The compounds of the invention can be incorporated into materials used to produce devices (e.g., medical devices) and can be added to disinfectants, cosmetics, household products, textiles, and plastics. The compounds of the invention include compounds having the structure according to Formula (I):

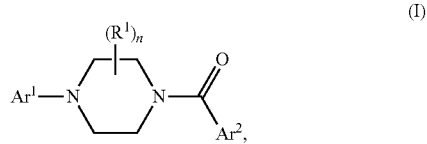

or a stereoisomer thereof, or a salt thereof, wherein
n is an integer between 0-4;

each $R^1$, when present, is, independently, OH, halogen, optionally substituted C1-C6 alkyl, or two $R^1$ on the same carbon combine to form an oxo group;

$Ar^1$ is optionally substituted phenyl or optionally substituted monocyclic 5- or 6-membered heteroaryl; and $Ar^2$ is optionally substituted phenyl or optionally substituted heteroaryl.

In some embodiments, n is 1 or 2, each $R^1$, when present, is optionally substituted C1-C6 alkyl, and/or the compound has a structure according to formula (I-a):

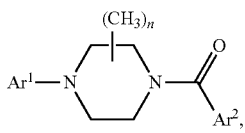

where n is 0 or 1.

With regard to the compounds of formula (I-a), $Ar^1$ may be a phenyl that includes 1 or 2 substituents that are electron-withdrawing (e.g., F, Cl, Br, I, CN, or $NO_2$). In certain embodiments, $Ar^1$ may be a phenyl having a $NO_2$ substituent. In other embodiments, $Ar^1$ includes 1, 2, or 3 substituents independently selected from halogen and unsubstituted C1-C6 alkyl. In other embodiments, $Ar^2$ may be unsubstituted phenyl. In some other embodiments, $Ar^2$ may be optionally substituted benzothiophene or optionally substituted phenyl. In certain embodiments, $Ar^2$ may be unsubstituted phenyl or unsubstituted benzothiophene. In other embodiments, $Ar^2$ may be phenyl having 1, 2, or 3 substituents selected, independently, from $NO_2$, CN, optionally substituted C1-C6 alkyl, or halogen. In further embodiments, the substituents may be, independently, selected from F, Cl, Br, and unsubstituted C1-C6 alkyl.

Exemplary compounds of formula (I) are described in Table 1 (above).

The compounds of the invention also include compounds having the structure according to Formula (II):

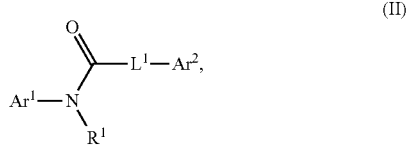

or a salt thereof, wherein $R^1$ is H or optionally substituted C1-C6 alkyl;

each $Ar^1$ and $Ar^2$ is, independently, an optionally substituted phenyl group; and $L^1$ is a covalent bond, $-O(CH_2)_n-$, or $-(CH_2)_nO-$, wherein n is an integer between 0-3.

With regard to the compounds of formula (II), in some embodiments, $R^1$ is H, $L^1$ is a covalent bond, $-O(CH_2)-$, or $-(CH_2)O-$, and/or the compound has a structure according to formula (II-a):

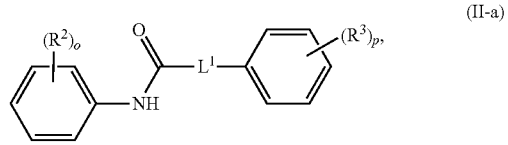

wherein each of o and p is, independently, an integer between 1-3;

each $R^2$ and $R^3$ is, independently, selected from halogen, optionally substituted C1-C6 alkyl, optionally substituted C1-C6 alkoxy; CN, $NO_2$, $CO_2H$, or $CO_2R^4$; and $R^4$ is optionally substituted C1-C6 alkyl or optionally substituted phenyl.

With regard to the compound of formula (II-a), In some embodiments, o may be 1 or 2. In other embodiments, p may be 1 or 2. In still other embodiments, $L^1$ is a bond. In certain embodiments, each $R^2$ and $R^3$ may be selected, independently, from F, Cl, Br, $NO_2$, unsubstituted C1-C6 alkyl, $CO_2H$, and $CO_2$ (unsubstituted C1-C6 alkyl).

Exemplary compounds of formula (II) are described in Table 2 (above).

The compounds of the invention also include those shown in Table 3 (above). In some embodiments, variants of the compounds of Table 3 can be used in the methods described herein. For example, where a compound includes a phenyl group (e.g., any of Compounds (13)-(27)), the phenyl group can be modified to be unsubstituted or to be substituted with 1, 2, 3, 4, or 5 substituents selected, independently, from optionally substituted C1-C6 alkyl, optionally substituted C1-C6 alkoxy, halogen, CN, $NO_2$, $CO_2H$, and $CO_2R^X$, where $R^X$ is an optionally substituted C1-C6 alkyl or an optionally substituted phenyl.

Similarly, compounds of Table 3 that include a heteroaryl group can be modified in order that the heteroaryl group is unsubstituted or substituted with, e.g., 1 or 2 substituents selected, independently, from optionally substituted C1-C6 alkyl, optionally substituted C1-C6 alkoxy, halogen, CN, $NO_2$, $CO_2H$, and $CO_2R^X$, where $R^X$ is an optionally substituted C1-C6 alkyl or an optionally substituted phenyl.

In other embodiments, the length of an alkylene linker in a Table 3 compound (e.g., Compounds (13), (14), (18), (22), (23), and (25)-(27)) can also be varied. For example, the alkylene linker can be varied such that it includes between 1-6 carbons (e.g., a C1-C6 alkylene, a C1-4 alkylene, a C1-2 alkylene, or even a C1 alkylene). Further, the alkylene may be unsubstituted or substituted.

In still other embodiments, carboxylic acid (e.g., $CO_2H$) can be replaced with the corresponding alkyl ester or phenyl ester. Regioisomers or linkage isomers of the compounds of Table 3 can also be used in the compositions and methods described herein.

Uses of the Compositions of the Invention

The present invention also features uses of the compounds of the invention or an adduct or salt thereof (e.g., compounds of formula (I), (I-a), (II), and (II-a), as well as those compounds shown in Tables 1, 2, and 3) for treating and/or inhibiting infection by a microbe, such as a fungus, yeast, mold, and bacterium, in a subject (e.g., a human). Administration of the compound(s) may be topical, mucosal, e.g., oral, nasal, vaginal, rectal, parenteral, transdermal, subcutaneous, intramuscular, intravenous, via inhalation, ophthalmic, and other convenient routes. Pharmaceutical compositions that include the compound(s) can be prepared for a variety of modes of administration and can be administered in a variety of unit dosage forms depending upon the method of administration.

The compounds of the invention may be administered to treat a variety of microbial infections. The compositions and methods of this invention are especially useful for treating or preventing a pathologic condition associated with a microbial infection and/or for decreasing bacterial and/or fungal growth in an animal or a human in need of such treatment.

The compositions and methods of this invention are especially useful for treating mucosa or other tissues of the oral cavity, a wound selected from the group consisting of an ulcer, a laceration, a deep penetrating wound and a surgical wound, and other diseases and disorders caused by microbial infection. For example, the patient to be treated may suffer from a fungal, yeast, and/or mold infection. Fungal infections (mycoses) can cause conditions including the following: dermatophytoses, dermatophytoma, a tinea infection (e.g., tinea capitis, tinea corporis, tinea pedis, tinea barbae, tinea cruris, tinea manuum, tinea faciale, tinea unguium, and tinea versicolor), onychomycosis, perionychomycosis, pityriasis versicolor, oral thrush, vaginal candidosis, respiratory tract candidosis, biliary candidosis, esophageal candidosis, urinary tract candidosis, systemic candidosis, mucocutaneous candidosis, mycetoma, cryptococcosis, aspergillosis, mucormycosis, chromoblastomycosis, paracoccidioidomycosis, North American blastomycosis, histoplasmosis, coccidioidomycosis, and sporotrichosis, each of which can be treated using the compositions of the invention. In addition, diseases caused by fungal infection include "systemic mycoses." These fungal infections are generalized throughout the body. Often, systemic infections are acquired via inhalation of airborne spores and initiated in the lungs. Examples of systemic infections that can be treated using the compositions of the invention include mucocutaneous candidosis, chromoblastomycosis, mycetoma, cryptococcosis, aspergillosis, mucormycosis, paracoccidioidomycosis, North American blastomycosis, histoplasmosis, coccidioidomycosis (San Joaquin or valley fever), and sporotrichosis. As with most systemic pathogens, if left untreated, serious life-threatening infections can develop. In some embodiments of the invention, the patient to be treated is an immunocompromised host, for example, those infected by HIV, those undergoing chemotherapy, transplant recipients, or cancer patients receiving immunosuppressive medications. In some embodiments of the invention, the subject to be treated is a premature or low birthweight infant and the compositions and methods of this invention are useful for reducing the risk of bacterial or fungal infection or sepsis in these patients. For example, the methods of the invention include administering a compound(s) of the invention (formulated in a pharmaceutically acceptable carrier) to a person colonized with pathogenic bacteria or fungus. The patient may be an immunocompromised patient affected with leukaemia, lymphoma, carcinoma, sarcoma, allogenic transplant, congenital or acquired immunodeficiency, cystic fibrosis, or AIDS. In some instances, the patient is treated for a biofilm-associated infection that is a nosocomial infection. In some cases a biofilm-associated infection is a mixed infection, comprising multiple different microorganisms. In some cases an individual suffering from a biofilm-associated infection is at increased risk of contracting a second infection. Biofilms are often associated with cystic fibrosis, endocarditis, osteomyelitis, otitis media, urinary tract infections, oral infections, and dental caries, among other conditions, each of which can be treated by administering a composition of the invention that includes one or more compounds of the invention or an adduct or salt thereof (e.g., compounds of formula (I), (I-a), (II), and (II-a), as well as those compounds shown in Tables 1, 2, and 3, such as compounds #4, 9, and/or 12).

The compositions and methods of this invention are especially useful for reducing the risk of bacterial infection in a human. Pathogenic bacteria include those selected from the group consisting of pneumococcal species, methicillin-resistant *Staphylococcus aureus*, multi-drug resistant *Pseudomonas* species, *Nesseria* sp., *Hemophilus* sp., *Proteus* sp., *Klebsiella* sp., and *Escherichia coli*. The compositions and methods of this invention are also useful for reducing the risk of infection by gram negative bacteria in a person. Gram negative bacteria include those selected from the group consisting of *Salmonella*, e.g. *S. Typhimurium, S. Enteritidis, S. arizonae, S. bongori, S. cholerae-suis, S. choleraesuis, S. enterica, S. paratyphi, S. pullorum, S. subterranea*, and *S. typhi* or *Pseudomonas*, e.g.; a bacterium of the *Pseudomonas aeruginosa* group such as *P. aeruginosa* group *P. aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans*, and *P. straminea*.

The compositions and methods of this invention are especially useful for reducing the risk of fungal or yeast infection in a human. Pathogenic fungi or yeast include those selected from the group consisting of a *Trichophyton* species, *Epidermophyton* species, *Candida* species, *Microsporum* species, *Aspergillus* species, *Paecilomyces* species, *Fusarium* species, *Acremonium* species, *Chaetomium* species, *Phoma* species, *Scopulariopsis* species, *Scytalidium* species, *Alternaria* species, *Epicoccum* species, *Curvularia* species, and any combination thereof.

The *Trichophyton* species can be, for example, *T. ajelloi, T. concentricum, T. equinum, T. erinacei, T. flavescens, T. gloriae, T. interdigitale, T. megnini, T. mentagrophytes, T. phaseoliforme, T. rubrum, T. schoenleini, T. simii, T. soudanense, T. terrestre, T. tonsurans, T. vanbreuseghemii, T. verrucosum, T. violaceum*, or *T. yaoundei*. The *Epidermophyton* species can be, for example, *E. floccosum* or *E. stockdaleae*. The *Candida* species can be, for example, *C. albicans, C. parapsiliosis, C. krusei, C. tropicalis, C. glabrata, C. parapsilosis, C. lusitaniae, C. kefyr, C. guilliermondii*, or *C. dubliniensis*. The *Microsporum* species can be, for example, *M. canis, M. gypseum, M. audouini, M. gallinae, M. ferrugineum, M. distortum, M. nanum, M. cookie*, or *M. vanbreuseghemii*. The *Epicoccum* species can be, for example, *E. nigrum*. The *Aspergillus* species can be, for example, *A. sydowii, A. terreus, A. niger, A. terreus, A. fumigatus, A. flavus, A. clavatus, A. glaucus* group, *A. nidulans, A. oryzae, A. terreus, A. ustus*, or *A. versicolor*. The *Paecilomyces* species can be, for example, *P. lilacinus* or *P. variotii*. The *Fusarium* species can be, for example, *F. oxysporum, F. solani*, or *F. semitectum*. The *Chaetomium* species can be, for example, *C. atrobrunneum, C. funicola, C. globosum*, or *C. strumarium*. The *Scopulariopsis* species can be, for example, *S. brevicaulis, S. candida, S. koningii, S. acremonium, S. flava, S. cinerea, S. trigonospora, S. brumptii, S. chartarum, S. fusca*, or *S. asperula*. The *Scytalidium* species can be, for example, *S. dimidiatum, S. hyalinum, S. infestans, S. japonicum*, or *S. lignicola*. The *Alternaria* species can be, for example, *A. alternate, A. chartarum, A. dianthicola, A. geophilia, A. infectoria, A. stemphyloides*, or *A. teunissima*. The *Curvularia* species can be, for example, *C. brachyspora, C. clavata, C. geniculata, C. lunata, C. pallescens, C. senegalensis*, or *C. verruculosa*.

In a preferred embodiment, the method includes treating a subject, e.g., a human, for candidiasis using a pharmaceutical composition that contains one or more of the compounds of the invention or an adduct or salt thereof (e.g., compounds of formula (I), (I-a), (II), and (II-a), as well as those compounds shown in Tables 1, 2, and 3, such as, e.g., compound #s 4, 9, and/or 12). *Candida* is a yeast and the most common cause of opportunistic mycoses worldwide. It is also a frequent colonizer of human skin and mucous membranes. Patients receiving fluconazole prophylaxis are particularly at risk of developing infections due to fluconazole-resistant *Candida krusei* and *Candida glabrata* strains (Barchiesi et al., *Eur. J. Epidemiol.* 9:455-456, 1993). Nevertheless, the diversity of *Candida* spp. that is encountered in infections is expanding and the emergence of other species that were rarely in play in the past is now likely. The clinical spectrum of candidiasis is extremely diverse. Almost any organ or system in the body can be affected. Candidiasis may be superficial and local or deep-seated and disseminated. Disseminated infections arise from hematogenous spread from the primarily infected locus. *Candida albicans* is the most pathogenic and most commonly encountered species among all. Its ability to adhere to host tissues, produce secretory aspartyl proteases and phospholipase enzymes, and transform from yeast to hyphal phase are the major determinants of its pathogenicity. Thus, the methods of the present invention include administration of one or more compounds of the invention to a subject (e.g., a human) in need of treatment for candidiasis (e.g., infection with *C. albicans*). In an embodiment, the subject being treated is diagnosed with a fluconazole-resistant *Candida* infection.

Yet another embodiment of the present invention is a process for imparting microbial control properties to a fluid composition, in which the process includes adding an anti-microbial composition of the invention, as defined hereinabove, to the fluid composition. Fluid compositions involved in this embodiment of the invention may be, but are not limited to, aqueous compositions susceptible to come into contact with, and subsequently infect, e.g., an animal or a human being.

The compounds of the invention can be used in anti-microbial compositions to reduce or inhibit biofilm formation on surfaces, e.g., surfaces of medical devices, such as an implantable medical device (e.g., a cardiac-assist device, an artificial heart valve, a catheter, a central line, an IV line, a joint, a stent, a prosthetic implant, a pacemaker, conduit, cannula, appliance, scaffold, an artificial sphincter, a pessary, tube, drain, trochar or plug, implant, a rod, a screw, or orthopedic or implantable prosthetic device or appliance, a suture, a drug delivery device, an oral implant, a denture, a brace, etc.), a cuff, dressing materials, a mesh, a hernia patch, a wound dressing, a bandage, syringes, gloves, and the like. In some embodiments, the compound or an adduct or salt thereof (e.g., compounds of formula (I), (I-a), (II), and (II-a), as well as those compounds shown in Tables 1, 2, and 3, such as, e.g., compound #s 4, 9, and/or 12) is incorporated into the materials used to manufacture the medical device. In other embodiments, the compound (e.g., compounds of formula (I), (I-a), (II), and (II-a), as well as those compounds shown in Tables 1, 2, and 3, such as, e.g., compound #s 4, 9, and/or 12) is used as a component of a coating applied to the surface of the medical device.

The compounds of the invention (e.g., compounds of formula (I), (I-a), (II), and (II-a), as well as those compounds shown in Tables 1, 2, and 3, such as, e.g., compound #s 4, 9, and/or 12) can also be used in non-medical applications such as in coatings or films in protecting surfaces from bio-fouling. Such surfaces include surfaces in contact with water, such as swimming pool liners, water cooling surfaces, hoses, water dispensers, water storage and distribution systems for drinking water or aquaculture, and surfaces in contact with marine environments (including fresh water, brackish water and salt water environments), for example, the hulls of ships, surfaces of docks or the inside of pipes in circulating or pass-through water systems. Other surfaces are susceptible to similar biofouling, for example walls exposed to rain water, walls of showers, roofs, gutters, pool areas, saunas, floors and walls exposed to damp environs such as basements or garages and even the housing of tools and outdoor furniture. For the treatment or disinfection of surfaces, the compounds of the invention may be applied in an amount ranging from 0.1 to 100000 mg per square meter surface. Application of the present compounds and/or formulations may follow known methods. For example, surfaces may be treated, e.g., by spraying, dipping; bulk materials are commonly equipped with the present compounds in powder form or in form of solutions or dispersions, e.g., by commonly known mixing or kneading processes.

The compounds of the invention can be used in the anti-microbial (e.g., anti-fungal) treatment of surfaces (e.g., as a disinfectant), and as an anti-microbial agent in, e.g., pharmaceutical compositions (e.g., an eye drop formulation, an inhalant, an adhesive paste, an anti-inflammatory skin care preparation, a wound healing formulation, and an agent against dermatophytes for use in products against seborrheic dermatitis, psoriasis and athletes foot in formulation types such as creams, lotions, gels, powders, oils, tonics, sprays, wet wipes, etc.), cosmetics (e.g., an eye make-up or an eye make-up remover, a sunscreen lotion, an after-sun skin care preparation, a revitalizing skin care preparation, an anti-aging skin care preparation, and an anti-acne composition), hygiene products (e.g., a tooth paste or gel, a mouth wash, a gargle, a hair treatment (e.g., an oil, spray, or hair gel, a shampoo, and a hair conditioner), a feminine hygiene composition, such as a feminine hygiene washing lotion or spray, a bath additive, a hair care preparation, a liquid or solid soap (based on synthetic surfactants and salts of saturated and/or unsaturated fatty acids), a lotion or cream, a deodorant, an aqueous or alcoholic solution, e.g., a cleansing solution for the skin, a nonwoven article (e.g. nappies/diapers, sanitary towels, panty liners, and cloths), an oil or a powder), household products (e.g., household and general-purpose cleaners for cleaning and disinfecting hard surfaces and in liquid or powder washing agents or softeners), and textiles (e.g., undyed and dyed or printed fiber materials, e.g., of silk, wool, polyamide, or polyurethanes, and especially cellulosic fiber materials of all kinds, such as, for example, natural cellulose fibers, such as cotton, linen, jute, and hemp, as well as cellulose and regenerated cellulose, leather, and the like) and plastics (e.g., polyethylene, polypropylene, polyurethane, polyester, polyamide, polycarbonate, latex, etc.). The pharmaceutical compositions are optionally in the form of an aqueous paste or gel or a liquid, such as an aqueous liquid or viscous liquid. Fields of use of the compositions of the invention include, for example, floor coverings, plastics coatings, plastics containers and packaging materials; kitchen and bathroom utensils (e.g., brushes, shower curtains, sponges, bathmats), latex, filter materials (air and water filters), and mattresses.

The compounds of the invention can also be used to reduce or inhibit microbial growth in industrial formulations, such as coatings, paints, and lubricants, and in paper treatment, especially in paper treatment liquors and printing thickeners of starch or cellulose derivatives.

The compounds of the invention can also be used to reduce or inhibit microbial growth on agricultural products, such as foods and vegetables.

In addition, the compounds of the invention are capable of penetrating biofilms on living and non-living surfaces, of preventing the adhesion of microbes (e.g., fungal microbes) to surfaces and any further build-up of the biofilm, of detaching such biofilm and/or inhibiting the further growth of the biofilm-forming micro-organisms in the biological matrix, or of killing such micro-organisms.

The compounds of this invention (e.g., compounds of formula (I), (I-a), (II), and (II-a), as well as those compounds shown in Tables 1, 2, and 3, such as, e.g., compound #s 4, 9, and/or 12) are also useful in preventing bio-fouling, or eliminating or controlling microbe accumulation on the surfaces either by incorporating the compounds into the article or surface of the article in question or by applying the compounds to these surfaces as part of a coating or film. When applied as a part of a film or coating, the compounds of the invention may be part of a composition which also includes a binder. The binder may be any polymer or oligomer compatible with the compounds of the invention. The binder may be in the form of a polymer or oligomer prior to preparation of the anti-microbial composition, or may form by polymerization during or after preparation, including after application to the substrate. In certain applications, such as certain coating applications, it may be desirable to crosslink the oligomer or polymer of the composition after application. The term binder, as used in the present invention, also includes materials such as glycols, oils, waxes and surfactants commercially used in the care of wood, plastic, glass and other surfaces. Examples include water proofing materials for wood, vinyl protectants, protective waxes and the like.

The compounds of the invention (e.g., compounds of formula (I), (I-a), (II), and (II-a), as well as those compounds shown in Tables 1, 2, and 3, such as, e.g., compound #s 4, 9, and/or 12) may be incorporated into a composition and applied as a coating or a film to an article or surface. When the composition is a thermoplastic film, which is applied to a surface, for example, by the use of an adhesive or by melt applications including calendaring and co-extrusion, the binder may be the thermoplastic polymer matrix used to prepare the film. When the composition is a coating, it may be applied as a liquid solution or suspension, a paste, gel, or oil, or the coating composition may be a solid, for example, a powder coating which is subsequently cured by heat, UV light, or other method known in the art. As the composition of the invention may be a coating or a film, the binder can be comprised of any polymer used in coating formulations or film preparation. For example, the binder may be a thermoset, thermoplastic, elastomeric, or inherently crosslinked or crosslinked polymer. Thermoset, thermoplastic, elastomeric, and inherently crosslinked or crosslinked polymers include, e.g., polyolefin, polyamide, polyurethane, polyacrylate, polyacrylamide, polycarbonate, polystyrene, polyvinyl acetates, polyvinyl alcohols, polyester, halogenated vinyl polymers, such as PVC, natural and synthetic rubbers, alkyd resins, epoxy resins, unsaturated polyesters, unsaturated polyamides, polyimides, silicon containing polymers, carbamate containing polymers, fluorinated polymers, crosslinkable acrylic resins derived from, e.g., substituted acrylic esters, e.g., from epoxy acrylates, urethane acrylates, or polyester acrylates. The polymers may also be blends and copolymers of the preceding chemistries. Biocompatible coating polymers, such as, e.g., poly[alkoxyalkanoate-co-3-hydroxyalkenoate] (PHAE) polyesters (Geiger et. al., *Polymer Bulletin* 52, 65-70, 2004), can also serve as binders in the present invention.

Alkyd resins, polyesters, polyurethanes, epoxy resins, silicone containing polymers, polyacrylates, polyacrylamides, fluorinated polymers and polymers of vinyl acetate, vinyl alcohol and vinyl amine are non-limiting examples of common coating binders useful in the present invention. Other coating binders, of course, are part of the present invention.

Coatings are frequently crosslinked with, for example, melamine resins, urea resins, isocyanates, isocyanurates, polyisocyanates, epoxy resins, anhydrides, poly acids and amines, with or without accelerators.

The compositions of the present invention (e.g., compounds of formula (I), (I-a), (II), and (II-a), as well as those compounds shown in Tables 1, 2, and 3, such as, e.g., compound #s 4, 9, and/or 12) may, for example, be a coating applied to a surface that is exposed to conditions favorable for bioaccumulation. The presence of the compound(s) of the invention in the coating reduces or inhibits the adherence of a microbial organism(s) (e.g., fungi, such as *C. albicans*) to the surface.

The compounds of the present invention may be part of a complete coating or paint formulation, such as a marine gel-coat, shellac, varnish, lacquer or paint, or may be incorporated into a composition through the use of one or more polymers or binders, as a carrier substance, such as those described above. Other additives that are typically encountered in such coating formulations or applications will find optional use in the present compositions, as well.

The coating may be prepared as a solvent or aqueous composition. Aqueous coatings are typically considered more environmentally friendly. The coating may include, for example, an aqueous dispersion that includes a compound of the invention, which may also be bound to or incorporated with a polymer, binder, or other carrier substance, such as those discussed above, or a water based coating or paint. The coating may be applied to a surface that has already been coated, such as a protective coating, or applied as a clear coat or a protective wax over a previously uncoated article.

The coating compositions of the invention may be applied to a surface by any conventional means including, e.g., spin coating, dip coating, spray coating, draw down, or by brush, roller or other applicator. A drying or curing period may be needed. Coating or film thickness may vary depending on application and would be apparent to one skilled in the art.

Compositions containing a compound of the invention may be in the form of a protective laminate film. Such a film typically includes thermoset, thermoplastic, elastomeric, or crosslinked polymers. Examples of such polymers include, but are not limited to, polyolefin, polyamide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyl resins, epoxy resins, unsaturated polyesters, unsaturated polyamides, polyimides, fluorinated polymers, silicon containing and carbamate polymers. The polymers may also be blends and copolymers of the preceding chemistries. When the composition is a preformed film it may be applied to a surface by, for example, the use of an adhesive, or co-extruded onto the surface. It may also be mechanically affixed via fasteners, which may further utilize a sealant or caulk. A plastic film may also be applied with heat, which includes calendaring, melt applications, and shrink wrapping.

Compositions containing a compound of the invention may be part of a polish, such a furniture polish, or a dispersant or surfactant formulation, such as a glycol or mineral oil dispersion or other formulation as used in for example wood protection. Examples of useful surfactants include, but are not limited to, polyoxyethylene-based surface-active substances, including polyoxyethylene sorbitan tetraoleate (PST), polyoxyethylene sorbitol hexaoleate (PSH), polyoxyethylene 6 tridecyl ether, polyoxyethylene 12 tridecyl ether, polyoxyethylene 18 tridecyl ether, TWEEN™ surfactants, TRITON™ surfactants, and the polyoxyethylene-polyoxypropylene copolymers such as the PLURONIC™ and POLOXAMER™ product series (from BASF). Other matrix-forming components include dextrans, linear PEG molecules (MW 500 to 5,000,000), star-shaped PEG molecules, comb-shaped and dendrimeric, hyperbranched PEG molecules, as well as the analogous linear, star, and dendrimer polyamine polymers, and various carbonated, perfluorinated (e.g., DUPONT ZONYL™ fluorosurfactants) and siliconated (e.g., dimethylsiloxane-ethylene oxide block copolymers) surfactants.

Given the wide array of applications for the present anti-microbial compositions, the composition may contain other additives such as antioxidants, UV absorbers, hindered amines, phosphites or phosphonites, benzofuran-2-ones, thiosynergists, polyamide stabilizers, metal stearates, nucleating agents, fillers, reinforcing agents, lubricants, emulsifiers, dyes, pigments, dispersants, other optical brighteners, flame retardants, antistatic agents, blowing agents and the like, such as the materials listed below, or mixtures thereof. The substrate can be an inorganic or organic substrate, for example, a metal or metal alloy; a thermoplastic, elastomeric, inherently crosslinked or crosslinked polymer as described above; a natural polymer such as wood or rubber; a ceramic material; glass; leather or other textile. The substrate may be, for example, non-metal inorganic surfaces such as silica, silicon dioxide, titanium oxides, aluminum oxides, iron oxides, carbon, silicon, various silicates and sol-gels, masonry, and composite materials such as fiberglass and plastic lumber (a blend of polymers and wood shavings, wood flour or other wood particles). The inorganic or organic substrate may be, for example, a metal or metal alloy, a thermoplastic, elastomeric, inherently crosslinked or crosslinked polymer, a ceramic material or a glass. The substrate may be a multi-layered article comprised of the same or different components in each layer. The surface coated or laminated may be the exposed surface of an already applied coating or laminate. The inorganic or organic substrate to be coated or laminated can be in any solid form. For example, polymer substrates may be plastics in the form of films, injection-molded articles, extruded workpieces, fibres, felts or woven fabrics. For example molded or extruded polymeric articles used in construction or the manufacture of durable goods such as siding, fascia and mailboxes can all benefit from being coated with or prepared using a composition that includes a compound of the invention.

Plastics which would benefit from being coated with or prepared using a composition that includes a compound of the invention include, but are not limited to, plastics used in medical devices (e.g., in-dwelling medical devices, such as catheters, and other devices, such as those described above), plastics used in construction or the manufacture of durable goods or machine parts, including outdoor furniture, boats, siding, roofing, glazing, protective films, decals, sealants, composites like plastic lumber and fiber reinforced composites, functional films including films used in displays as well as articles constructed from synthetic fibers such as awnings, fabrics such as used in canvas or sails and rubber articles such as outdoor matting and other uses cited in this disclosure. Exemplary of such plastics are polypropylene, polyethylene, PVC, POM, polysulfones, styrenics, polyamides, urethanes, polyesters, polycarbonate, acrylics, butadiene, thermoplastic polyolefins, ionomers, unsaturated polyesters and blends of polymer resins including ABS, SAN and PC/ABS.

The anti-microbial compounds of the invention are also effective in protecting useful plants, such as plants in agriculture, in horticulture and in forests, plant parts and seeds from disease and spoilage. For example, the present invention also provides a method of applying to useful plants, the locus thereof or propagation material thereof a composition which includes one or more compounds of the invention. The compositions can be used, e.g., as foliar, soil and seed treatment fungicides. The compositions of the present invention are of particular interest for controlling a large number of fungi in various useful plants or their seeds, especially in field crops, such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits. When applied to plants, the anti-microbial compounds of the invention are applied at a rate of 1 to 5000 g active ingredient per hectare (a.i./ha), for example 2 to 2000 g a.i./ha, for example, 5 to 2000 g a.i./ha, for example, 10 to 1000 g a.i./ha, e.g. 50, 75, 100, 200, 250, 500, 800, 1000, 1500 g a.i./ha. In agricultural practice the application rates depend on the type of effect desired, and typically range from 20 to 4000 g of total antimicrobials per hectare. When treating seed, rates of 0.001 to 50 g of the present anti-microbial compounds, for example 0.01 to 10 g, per kg of seed, are generally sufficient.

The composition comprising the anti-microbial compounds of the invention may be employed in any conventional form, for example in the form a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants. Such compositions may be produced in conventional manner, e.g., by mixing the active ingredients with appropriate formulation inerts (diluents, solvents, fillers and optionally other formulating ingredients such as surfactants, biocides, anti-freeze, stickers, thickeners and compounds that provide adjuvancy effects). F or example, formulations to be applied in spraying forms, such as water dispersible concentrates (e.g. EC, SC, DC, OD, SE, EW, EO and the like), wettable powders and granules, typically contain surfactants, such as wetting and dispersing agents and other compounds that provide adjuvancy effects. In general, the formulations include from 0.01 to 90% by weight of at least one of the anti-microbial compounds of the invention, from 0 to 20% agriculturally acceptable surfactant and 10 to 99.99% solid or liquid formulation inerts and adjuvant(s), and optionally other active agents, particularly microbiocides or conservatives or the like. Concentrated forms of compositions generally contain in between about 2 and 80%, for example, between about 5 and 70% by weight of total active agent. Application forms of formulation may for example contain from 0.01 to 20% by weight, for example from 0.01 to 5% by weight of active agent.

The materials, products, formulations, or compositions described above usually contain the compound(s) of the present invention (e.g., compounds of formula (I), (I-a), (II), and (II-a), as well as those compounds shown in Tables 1, 2, and 3, such as, e.g., compound #s 4, 9, and/or 12) in an amount within the range of 0.01 to 50% by weight (e.g., 0.1 to 25% by weight, 0.5 to 15% by weight, or 0.5 to 10% by weight), relative to the overall weight of the material, product, formulation, or composition.

Pharmaceutical Compositions, Dosages, and Routes of Administration

Pharmaceutical compositions of the invention, which include one or more compounds of the invention or an adduct or salt thereof (e.g., compounds of formula (I), (I-a), (II), and (II-a), as well as those compounds shown in Tables 1, 2, and 3, such as compound #s 4, 9, and/or 12) can be administered for prophylactic, therapeutic, and/or hygienic use. Such administration can be by topical, mucosal, e.g., oral, nasal, vaginal, rectal, parenteral, transdermal, subcutaneous, intramuscular, intravenous, via inhalation, ophthalmic, and other convenient routes. The pharmaceutical compositions can be administered in a variety of unit dosage forms depending upon the method of administration. For example, unit dosage forms suitable for oral administration include powder, tablets, pills, capsules and lozenges.

Pharmaceutical compositions of the invention can also be delivered by means of a microparticle or nanoparticle, a liposome, a nanoemulsion (see, e.g., U.S. Pat. No. 8,226,965), or other delivery vehicle or matrix. A number of biocompatible polymeric materials are known in the art to be of use for drug delivery purposes. Examples include polylactide-co-glycolide, polycaprolactone, polyanhydride, and copolymers or blends thereof.

The compositions for administration will commonly include a solution of a compound of the invention (e.g., compounds of formula (I), (I-a), (II), and (II-a), as well as those compounds shown in Tables 1, 2, and 3, such as, e.g., compound #s 4, 9, and/or 12) dissolved in or admixed with a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions, such as pH adjusting and buffering agents, toxicity adjusting agents and the like, for example, sodium acetate, sodium chloride, potassium chloride, calcium chloride, sodium lactate and the like. The concentration of anti-microbial compound(s) in these formulations can vary widely, and will be selected primarily based on fluid volumes, viscosities, body weight, and the like in accordance with the particular mode of administration selected and the patient's needs.

Thus, a typical pharmaceutical composition of the invention for intravenous administration would include about 0.0001 to about 100, or about 0.001 to about 10, or about 0.01 to about 10, mg of the compound(s) per patient per day. Dosages from about 0.001 mg, up to about 1000 mg, per patient per day may be used, particularly when administered to a secluded site and not into the blood stream, such as into a body cavity or into a lumen of an organ. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

Compositions containing the anti-microbial compound(s) of the invention or an adduct or salt thereof (e.g., compounds of formula (I), (I-a), (II), and (II-a), as well as those compounds shown in Tables 1, 2, and 3, such as, e.g., compound #s 4, 9, and/or 12) can be administered for therapeutic or prophylactic treatments. In therapeutic applications, compositions are administered to a patient suffering from a disease, e.g., a fungal infection, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the anti-microbial compound(s) of the invention to effectively treat the patient.

The therapeutic composition of the invention can be combined for therapeutic use with additional active ingredients, e.g., in conventional pharmaceutically acceptable carriers or diluents, along with physiologically innocuous stabilizers and excipients; see Berkow (Ed.), The Merck Manual, Merck, Rahway, N.J. These combinations can be filtered sterile and placed into dosage forms as by lyophilization in dosage vials or storage in stabilized aqueous preparations.

The invention further provides a pharmaceutical composition for treating a human bacterial or fungal infection that includes one or more compounds of the invention in an amount effective to treat a human bacterial or fungal infection and a pharmaceutically acceptable carrier. The compositions may also include, e.g., one or more antibiotics. In a preferred method, the treatment of a bacterial infection includes the addition of an antibiotic(s) for combination or synergistic therapy with a compound of the invention or an adduct or salt thereof (e.g., compounds of formula (I), (I-a), (II), and (II-a), as well as those compounds shown in Tables 1, 2, and 3, such as, e.g., compound #s 4, 9, and/or 12). The appropriate antibiotic administered will typically depend on the susceptibility of the bacteria such as whether the bacteria is gram negative or gram positive, and will be easily discernable by one of skill in the art.

Examples of particular classes of antibiotics useful for combination or synergistic therapy with a compound of the invention, either in the same composition or individually, include aminoglycosides (e.g., amikacin, gentamicin, kanamycin, netilmicin, tobramycin, streptomycin, azithromycin, clarithromycin, erythromycin, erythromycin estolate/ethylsuccinate/gluceptate/lactobionate/stearat), beta-lactams, such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin, and piperacillin), cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin), quinolones and fluoroquinolones (e.g., fleroxacin, nalidixic acid, norfloxacin, ciprofloxacin, ofloxacin, enoxacin, lomefloxacin and cinoxacin), carbepenems (e.g., imipenem), tetracyclines and macrolides (e.g., doxycycline, minocycline, tetracycline, erythromycin, and clarithromycin), monobactams (e.g., aztreonam), and glycopeptides (e.g., vancomycin, teicoplanin). Other antibiotics include chloramphenicol, clindamycin, trimethoprim, sulfamethoxazole, nitrofurantoin, rifampin and mupirocin. These compositions can be administered to reduce or inhibit biofilm formation or maintenance, e.g., in a human subject.

The quantities of agents necessary for effective therapy depend upon many different factors, including means of administration, target site, physiological state of the patient, and other medicaments administered. Thus, treatment dosages may be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (Eds.), (1990) Goodman and Gilman's: The Pharmacological Basis of Therapeutics, 8th ed., Pergamon Press, Tarrytown, N.Y., and in Remington's Pharmaceutical Sciences, 17th ed. (1990), Mack Publishing Co., Easton, Pa. Methods for administration are discussed herein and below, e.g., for oral, intravenous, intraperitoneal, or intramuscular administration, transdermal diffusion, and others. Pharmaceutically acceptable carriers may include water, saline, buffers, and other compounds described, e.g., in The Merck Index, Merck & Co., Rahway, N.J. See also (e.g.) Avis et al. (Eds.), (1993) Pharmaceutical Dosage Forms: Parenteral Medications, Dekker, New York, and Leiberman et al. (Eds.), (1990) Pharmaceutical Dosage Forms Disperse Systems, Dekker, New York. Slow-release formulations or slow-release apparatus may be utilized for continuous administration.

Therapeutic formulations may be administered in any conventional dosage formulation. Whereas it is possible for the active ingredient to be administered alone, it is preferable to present it as a pharmaceutical formulation. Formulations comprise at least one active ingredient (e.g., one or more of the compounds of the invention or an adduct or salt thereof (e.g., compounds of formula (I), (I-a), (II), and (II-a), as well as those compounds shown in Tables 1, 2, and 3, such as compound #4), together with one or more acceptable carriers therefor. Each carrier is preferably both pharmaceutically and physiologically acceptable in the sense of being compatible with the other ingredients and not injurious to the patient. Formulations include those suitable for mucosal, e.g., oral, vaginal, topical, rectal, nasal, or parenteral administration (including subcutaneous, intramuscular, intravenous and intradermal administration). The formulations may conveniently be presented in unit dosage form and may be prepared by any methods well known in the art of pharmacy: e.g., Gilman et al. (Eds.), (1990) Goodman and Gilman's: The Pharmacological Basis of Therapeutics, 8th ed., Pergamon Press; and Remington's Pharmaceutical Sciences, 17th ed. (1990), Mack Publishing Co., Easton, Pa. Further, the invention may be combined with or used in association with other chemotherapeutic or chemopreventive agents.

Therapeutic compositions according to the invention that include a compound(s) of the invention or an adduct or salt thereof (e.g., compounds of formula (I), (I-a), (II), and (II-a), as well as those compounds shown in Tables 1, 2, and 3, such as, e.g., compound #s 4, 9, and/or 12) may be formulated into topical preparations for local therapy by including a therapeutically effective concentration of the anti-fungal agent(s) in a mucosal or dermatological vehicle. The amount to be administered, and the concentration in the topical formulations, depend upon the vehicle selected, the clinical condition of the patient, the systemic toxicity and the stability of the formulation. Thus, a physician knows to employ the appropriate preparation containing the appropriate concentration of therapeutic agents in the formulation, as well as the appropriate amount of formulation to administered depending upon clinical experience with the patient in question or with similar patients. The concentration of therapeutic compounds of the invention for mucosal or topical formulations is in the range of greater than from about 0.01 mg/ml to about 2500 mg/ml. Typically, the concentration of the compounds of the invention in the compositions for topical formulations is in the range of greater than from about 1 mg/ml to about 200 mg/ml. Solid dispersions of the compositions according to the invention, as well as solubilized preparations, may be used. Thus, the precise concentration to be used in the vehicle is subject to modest experimental manipulation in order to optimize the therapeutic response. For example, greater than about 10 mg anti-fungal compound/100 grams of vehicle may be useful, e.g., with 1% w/w hydrogel or other known vehicles. Suitable vehicles, in addition to gels, are oil-in-water or water-in-oil emulsions using mineral oils, petroleum and the like.

Mucosal or topical preparations of the therapeutic composition either for systemic or local delivery may be employed and may contain excipients as described above for parenteral administration and other excipients used in a topical preparation such as cosolvents, surfactants, oils, humectants, emollients, preservatives, stabilizers and antioxidants. Pharmacologically acceptable buffers may be used, e.g., Tris or phosphate buffers. The topical formulations may also optionally include one or more agents variously termed enhancers, surfactants, accelerants, adsorption promoters or penetration enhancers, such as an agent for enhancing percutaneous penetration of the therapeutic compounds of the invention or other agents. Such agents should desirably possess some or all of the following features as would be known to the ordinarily skilled artisan: pharmacological inertness, non-promotive of body fluid or electrolyte loss, compatible with the therapeutic composition (non-inactivating), and capable of formulation into creams, gels or other topical delivery systems as desired.

Topical preparations may be applied daily (once, twice, thrice, or as needed) directly to the skin or mucosa and are then preferably occluded, i.e., protected by overlaying a bandage, polyolefin film or other barrier impermeable to the topical preparation.

Alternatively, the composition of the invention may be administered orally. Typically, a therapeutically effective oral dose of a composition according to the invention is in the range from about 0.05 mg/kg body weight to about 50 mg/kg body weight per day. In one embodiment, an effective dose is in the range from about 0.05 mg/kg body weight to about 5 mg/kg body weight per day.

In one embodiment, the pharmaceutical composition is administered vaginally. For intravaginal administration, the therapeutic agents may be formulated as is known in the art for direct application to the vaginal area. Forms chiefly conditioned for vaginal application take the form, for example, of creams, milks, gels, dispersion or micro-emulsions, lotions thickened to a greater or lesser extent, impregnated pads, ointments, aerosol formulations (e.g., sprays or foams), creams, lotions, pastes, jellies, sprays, and aerosols. Alternatively, the composition can be formulated to be part of an adhesive polymer, such as polyacrylate or acrylate/vinyl acetate copolymer. The dose will be dependent upon the properties of the specific composition employed, e.g., its activity and biological half-life, the concentration of composition in the formulation, the site and rate of dosage, the clinical tolerance of the patient involved, the disease afflicting the patient and the like, as is well within the skill of the physician.

In addition, the compositions of the invention may be administered to the lung(s) of a subject by any suitable means, e.g., be inhaled into a patient's respiratory tract and lungs through the nose or mouth. The composition of the invention can be aerosolized in a variety of forms, such as, but not limited to, dry powder inhalants, metered dose inhalants, or liquid/liquid suspensions. When administered by inhalation, carriers such as polyethylene glycol or glycols, DPPC, methylcellulose, powdered dispersing agents can be used. In some embodiments of the invention, a composition of the invention is administered by inhalation, for example, in a nebulized form. For example, delivery may be by use of a single-use delivery device, a mist nebulizer, a breath-activated powder inhaler, an aerosol metered-dose inhaler (MDI) or any other of the numerous nebulizer delivery devices available in the art. Additionally, mist tents or direct administration through endrotracheal tubes may also be used. In addition, delivery via an intratracheal or nasopharyngeal mode will be efficacious for certain indications. The dose will be dependent upon the properties of the specific composition employed, e.g., its activity and biological half-life, the concentration of composition in the formulation, the site and rate of dosage, the clinical tolerance of the patient involved, the disease afflicting the patient and the like, as is well within the skill of the physician.

The compositions of the present invention may be administered in solution. The compositions thereof may be in a solution having a suitable pharmaceutically acceptable buffer such as phosphate, Tris(hydroxymethyl)aminomethane-HCl or citrate and the like. Buffer concentrations should be in the range of 1 to 100 mM. The composition solution may also contain a salt, such as sodium chloride or potassium chloride in a concentration of 50 to 150 mM. An effective amount of a stabilizing agent, such as an albumin, a globulin, a gelatin, a protamine or a salt of protamine may also be included, and may be added to a solution containing composition or to the composition from which the solution is prepared.

The compositions of the invention can be administered in the form of an article or carrier such as a bandage, insert, syringe-like applicator, tablet, suppository, pessary, powder/talc or other solid, solution, liquid, spray, aerosol, douche, ointment, tampon, foam, cream, gel, paste, microcapsules, vaginal sponge, vaginal ring, controlled release formulation, sustained release formulation or bioadhesive gel (e.g., a mucoadhesive thermo-gelling composition (see, for example, U.S. 2003/0204180, which is incorporated herein by reference)).

The term "unit dosage" and its grammatical equivalents as used herein refer to physically discrete units suitable as unitary dosages for human patients and other warm blooded animals, each unit containing a predetermined effective and potentiating amount of at least one compound of the invention calculated to produce the desired therapeutic effect in association with the required physiologically tolerable carrier, e.g., a diluent or a vehicle. The specifications for the unit dosage forms of this invention are dictated by and are directly dependent on (a) the unique characteristics of the active ingredient(s) and the particular therapeutic effect to be achieved, and (b) the limitations inherent in the art of compounding for therapeutic use in humans and other animals. Examples of suitable unit dosage forms in accord with this invention are tablets, capsules, pills, powder packets, granules, wafers, and the like, segregated multiples of any of the foregoing, as well as liquid solutions, emulsions and suspensions. The amount of each active ingredient that is administered in vivo depends on the age and weight of the patient, the particular disease to be treated and its severity, the frequency of administration, and the route of administration.

In any treatment regimen, the therapeutic composition may be administered to a patient either singly or in a cocktail containing other therapeutic agents, compositions, or the like, including, but not limited to, immunosuppressive agents, tolerance-inducing agents, potentiators and side-effect relieving agents. Particularly preferred are immunosuppressive agents useful in suppressing allergic reactions of a host. Preferred immunosuppressive agents include prednisone, melphalain, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexiline, verapamil, amantadine and chloroquine. All of these agents are administered in generally accepted efficacious dose ranges such as those disclosed in the Physician's Desk Reference, 41st Ed., Publisher Edward R. Barnhart, N.J. (1987).

Compositions of the invention that include one or more compounds of the invention or an adduct or salt thereof (e.g., compounds of formula (I), (I-a), (II), and (II-a), as well as those compounds shown in Tables 1, 2, and 3, such as, e.g., compound #s 4, 9, and/or 12) may also be formulated in controlled or sustained release compositions. The compounds of the invention may be encapsulated within a biodegradable-biocompatible polymeric matrix. The biodegradable-biocompatible polymeric matrix can be used to provide sustained release of a compound(s) of the invention for a period of 10 to up to 100 days in an aqueous physiological environment.

Controlled drug delivery from a biodegradable-biocompatible matrix offers profound advantages over conventional drug/antigen dosing. Drugs/antigens can be used more effectively and efficiently, less drug/antigen is required for optimal therapeutic effect and, in the case of drugs, toxic side effects can be significantly, reduced or essentially eliminated through drug targeting. The stability of some drugs/antigens can be improved allowing for a longer shelf-life, and drugs/antigens with a short half-life can be protected within the matrix from destruction, thereby ensuring sustained release of active agent over time. The benefit of a continuous sustained release of drug/antigen is beneficial because drug levels can be maintained within a constant therapeutic range and antigen can be presented either continuously or in a pulsatile mode as required to stimulate the optimal immune response. All of this can be accomplished with a single dose of encapsulated drug/antigen. Sustained release compositions include those described in, e.g., U.S. Pat. No. 6,309,669.

EXAMPLES

The following examples are to illustrate the invention. They are not meant to limit the invention in any way.

Example 1

Identifying Small Molecule Inhibitors of *C. albicans* Adhesion

To detect small molecules that interfere with adhesion of *Candida albicans*, we modified a previous protocol for measuring adhesion of *Saccharomyces cerevisiae* to polystyrene (Reynolds, 2001). We observed that *C. albicans* cells bind strongly 96-well polystyrene plates that have been optimized for protein binding (see Methods), and we used this robustly-bound substrate to set a high threshold for inhibitors of adhesion. After binding, *C. albicans* cells were stained with crystal violet, followed by washing to remove unbound dye and cells. Cells that remained bound after washing were then detected by measuring dye absorbance at 590 nm (see Methods for details). We screened a library of 30,000 small molecules (Chembridge) at a final concentration of 50 µM, testing for effects on adhesion by the wild-type clinical isolate *C. albicans* strain SC5314 (Gillum, *Mol and Gen Gene MGG*. 198: 179-182, 1984). As a negative control, each plate contained a column of wells containing SC5314 cells exposed only to DMSO vehicle (FIG. 1A, last column). As a positive control for poor adhesion, each plate also included a column of wells containing *C. albicans* edt1$^{-/-}$ mutant cells (Wheeler, *PloS Pathog*. 4: e1000227, 2008) that lack a cell wall protein important for adhesion (FIG. 1A, first column). We ranked the normalized scores for each compound (see Methods). Forty compounds inhibited adhesion by >75%, and many of these fell into two scaffold families. Omitting compounds within this list that were very similar, we reordered 26 of the candidate compounds (termed #1-8 and 10-26; Table 1-3) for subsequent characterization.

Figure 7:
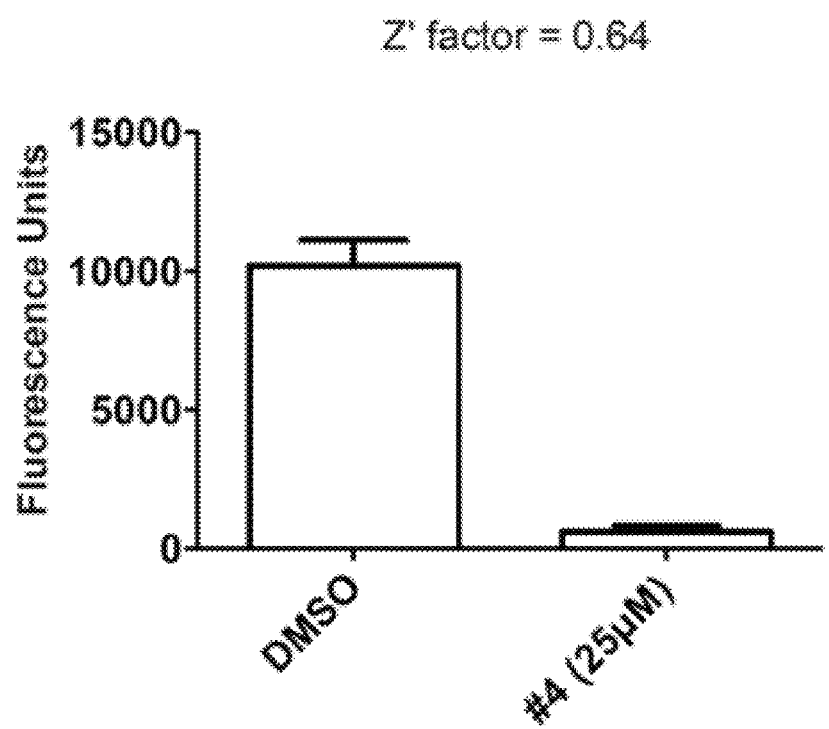
FIG. 7.

We prioritized the candidate compounds by testing the dose-dependence of their effects. Because of the laborious washing required to remove background crystal violet dye staining, we developed adhesion assays using alternative detection reagents. Previous experiments screens have used the vital dye alamarBlue to measure *Candida* viability (Lafleur, *J. Antimicrob Chemother*. 66: 820-826, 2011; Youngsaye supra), so we tested this reagent as a way to measure cells remaining adhered after washing. We found that after two rounds of washing, alamarBlue robustly detected the adhesion differences between the wild-type SC5314 and edt1$^{-/-}$ mutant cells (FIG. 1B; FIG. 7). The majority of the reordered compounds were effective at reducing *Candida* adhesion at 50 µM, the concentration originally tested during the screen. However, upon reducing the concentration to 25 µM, some of these compounds were substantially less effective (FIG. 1B). Although compounds that were still effective at 25 µM were less generally less so at 7.5 µM (FIG. 1C), many candidates still reduced adhesion by >50% at this lower concentration.

Because alamarBlue measures the metabolic activity of live cells, we sought to confirm these data with a different assay that directly detected cells remaining after washing, regardless of any potential effects on viability or metabolism. To do this, we measured adhesion of cells plated and washed as before, but here using a *C. albicans* strain encoding GFP. This allowed us to measure adhesion both in a fluorescence plate reader and by microscopy (FIGS. 1D and 1E). Indeed, these GFP-based assays confirmed that all the compounds effective at 25 µM in the alamarBlue-based assay impair *C. albicans* adhesion to polystyrene. We conclude that our chemical screen detected multiple compounds that block adhesion to polystyrene, and that these can be assayed via multiple detection methods.

Example 2

One Candidate Compound Inhibits *C. albicans* Adhesion to Human Cells, Affects Multiple Pathogenic *Candida* Species, and is not Toxic to Human Cells In addition to experiments with inert surfaces, we also tested how the candidate compounds would affect *C. albicans* adherence to human cells, measuring binding of Green Fluorescent Protein (GFP)-encoding *C. albicans* cells to monolayers of human lung epithelial A549 cells, which are an effective substrate for *Candida* adhesion (Kitamura, *Antimicrob Agents Chemother*. 53: 3963-3971, 2009). We tested each of reordered compounds, and observed that compound #4 was by far the strongest inhibitor of adhesion to human epithelial cells, as shown by both fluorescence quantitation (FIG. 2A), and by microscopy (FIG. 2B). We also demonstrated that compound #4 does not affect the viability of this human cell line, even at concentrations much larger than those used in the adhesion assay (e.g. 250 µM, FIG. 2C). We conclude that compound #4 is not toxic to this human cell line under our assay concentrations, but can impair fungal adhesion both to inert surfaces and to cultured human epithelial cells.

To test the applicability of compound #4 to other fungal pathogens, we examined adhesion by additional pathogenic *Candida* species (Junqueira, *BMC Microbiol*. 11: 1-9, 2011). Specifically, we observed that compound #4 caused similar inhibition of polystyrene adhesion by *C. dublinensis* and *C. albicans* (FIG. 2D), as well as for *C. tropicalis*. Compound #4 therefore inhibits adhesion by multiple pathogenic *Candida* species.

We performed several additional experiments to characterize the ability of compound #4 to inhibit *Candida* adhesion to polystyrene. First, titration over a wide range of concentrations showed that it has an IC50 value ~3 µM in the GFP-based adhesion assay (FIG. 8A). Second, we tested whether compound #4 affects *C. albicans* cell growth rate. Measuring growth rates in liquid culture, we observed that compound #4, but not the other compounds tested (compounds #5-8; Table 1), reduced the doubling time (FIG. 8B). Therefore, compound #4 slows *C. albicans* growth but is minimally toxic to human epithelial cells (FIG. 2C), properties that are desirable for candidate antifungal compounds.

Example 3

Figure 9:
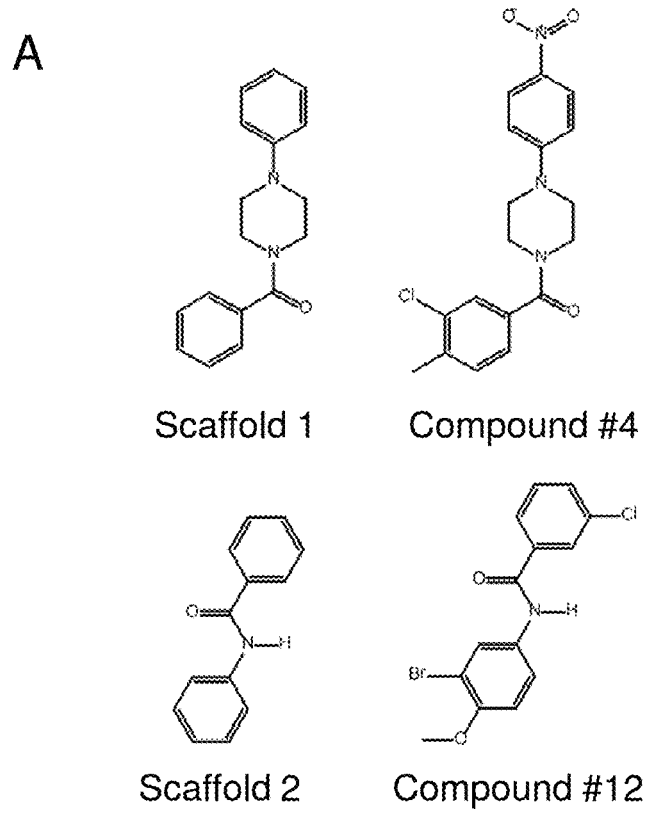
FIGS. 9A-9B. Test of synergy between scaffold 1 and 2.
Figure 9:
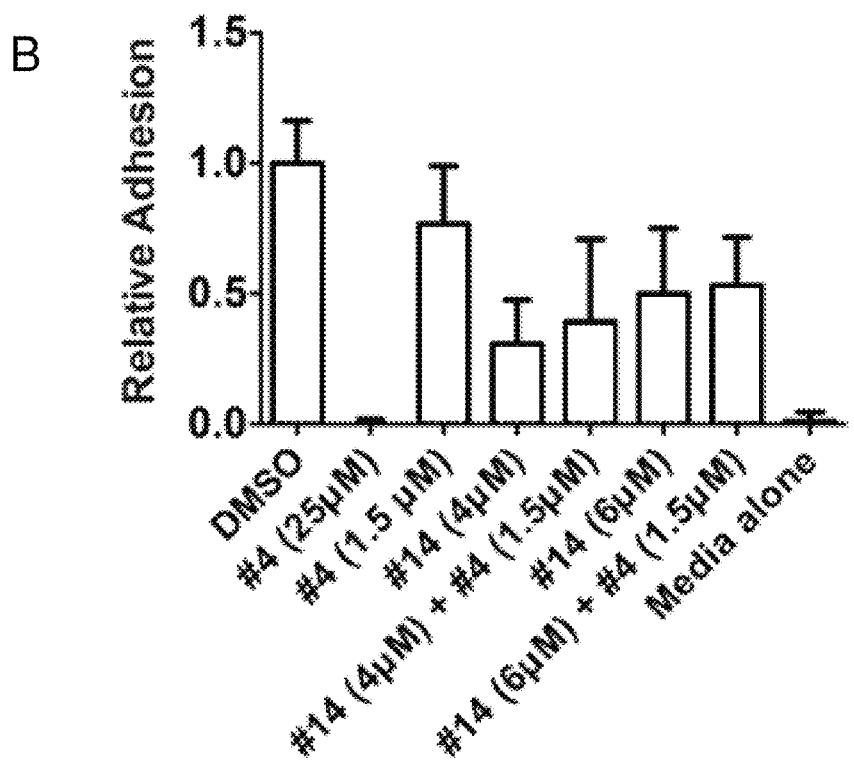

Compound #4 is Functionally Distinct from Previously Described Compounds that Affect *Candida* Drug Resistance Many of our initial set of candidate compounds had one of two distinct chemical scaffolds (Tables 1 and 2; FIG. 9A). We tested whether we could detect any synergistic effects upon combining members of these two classes. Specifically, we combined doses of compounds that alone had partial effects on adhesion: compound #4 (Scaffold 1, 1.5 µM), and compound #12 (Scaffold 2, 4 and 6 µM). Combining these compounds at these concentrations did not further reduce adhesion (FIG. 9B). Therefore, we focused subsequent experiments on single compounds alone.

During the course of our studies, results were published from a high-throughput screen for compounds that do not impair growth of wild-type *C. albicans*, but cause synergistic reductions in viability of fluconazole-resistant strains in the presence of low concentrations of fluconazole (Youngsaye supra). Notably, that screen's best candidate compound ("Q1"; Chembridge #7959790; FIG. 3A) has a backbone similar to our compound #4. However, compound Q1 includes a quinoline group distal to the piperazinyl linker, rather than the single-ring nitrophenyl group present in compound #4 (FIG. 3A). We therefore tested whether the presence of the quinoline group affected the activities of the candidate compounds in a variety of assays. We also tested whether different substitutions on the aryl group adjacent to the carbonyl at the other end of the molecules would correlate with activities, comparing compound #9 with #4 and a compound we termed "Q2" (Chembridge #9009034) with Q1 (FIG. 3A).

First, we tested this set of compounds for effects on *C. albicans* adhesion to polystyrene, using Alamar Blue as a detection reagent. Both compounds #4 and #9 were effective adhesion inhibitors in this assay. In contrast, neither compound Q1 nor Q2 were inhibitory (FIG. 3B). Therefore, the presence of the quinoline group on compounds Q1 and Q2 correlated with a lack of activity, and the substitutions on the other end of the compounds were less important. Thus, compounds #4 and Q1 are functionally distinct.

We also compared these compounds in the human cell-binding assay. In this case, only compound #4 strongly inhibited *C. albicans* to human A549 cells (FIG. 3C). Therefore, perturbation of either of the aryl side groups on both sides of the molecule can impair the human cell adhesion inhibition activity of compound #4, further illustrating the distinct properties of this compound.

Figure 10:
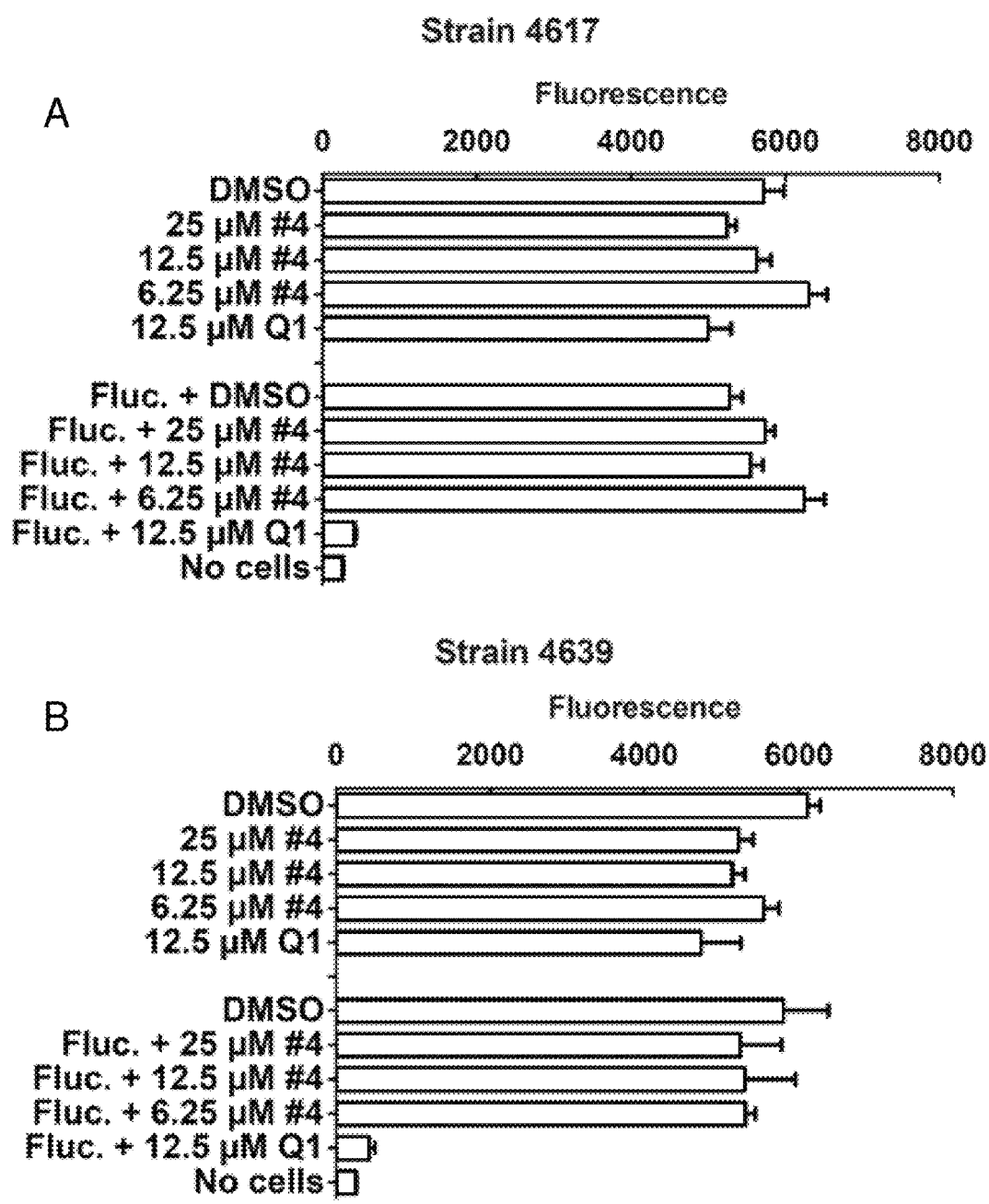
FIG. 10 is a graph showing titration of Asf1/H3/H4 in ELISA assays. Data from triplicate assays are shown.

Finally, we tested whether compound #4 would inhibit growth of fluconazole-resistant *C. albicans* strains in the presence of low levels of fluconazole, because that is the activity described for compound Q1 (Youngsaye supra). To measure cell viability rather than adhesion, we performed alamarBlue-based viability measurements without wash steps, using fluconazole-resistant *C. albicans* strains obtained from an AIDS patient who had been treated with fluconazole for oral candidaisis (Bachmann, 2002). We confirmed that compound Q1 does indeed synergize with fluconazole to inhibit growth of these strains (FIG. 10). In contrast, compound #4 alone did not affect fluconazole-resistant *C. albicans* viability, whether alone or in the presence of fluconazole.

Example 4

Several Candidate Compounds Inhibit *Candida* Hyphal Morphogenesis

Figure 2:
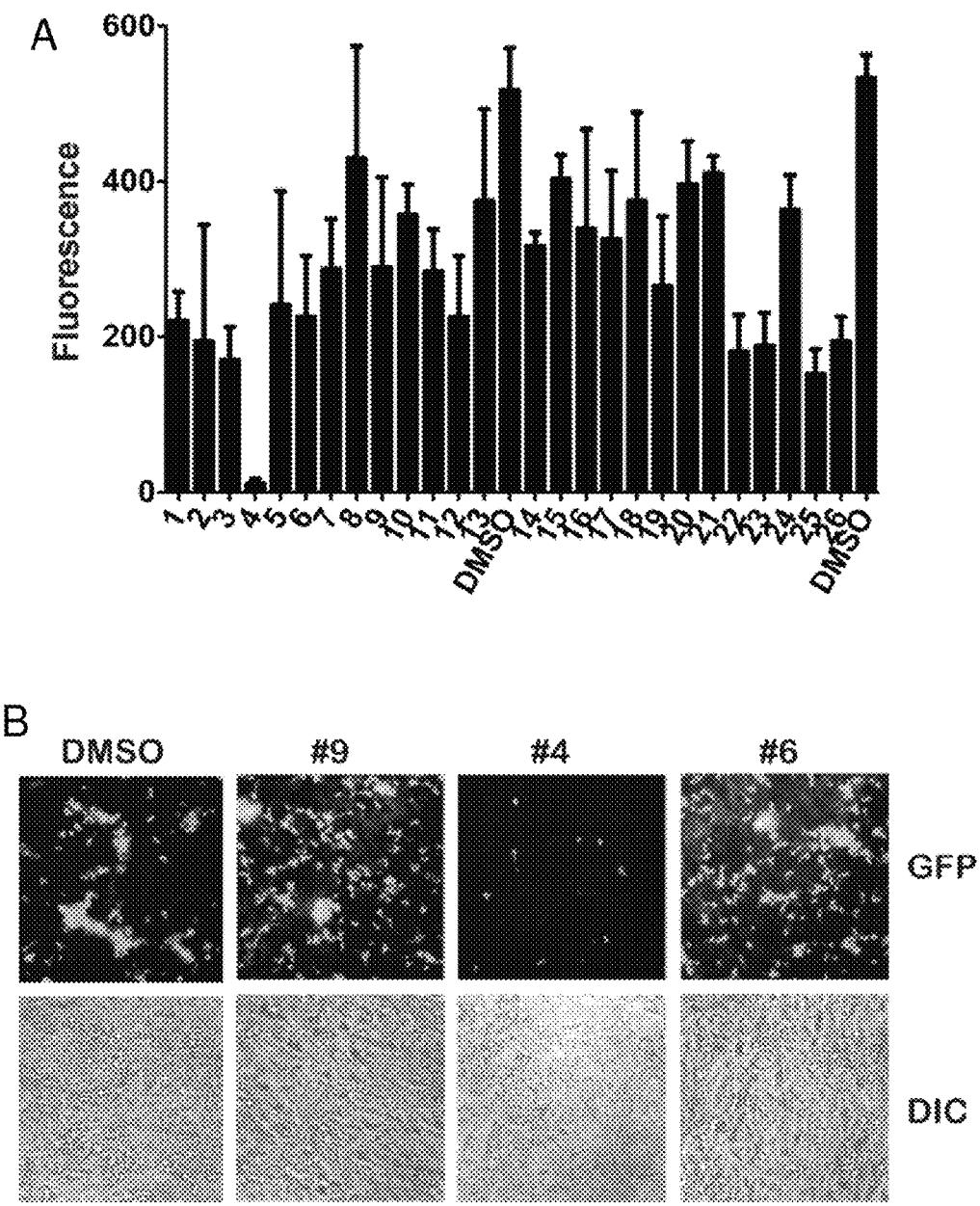
FIGS. 2A-2D. Compound #4 is a non-toxic inhibitor of adhesion by multiple Candida species and reduces fungal binding to human A549 cell monolayers.
Figure 3:
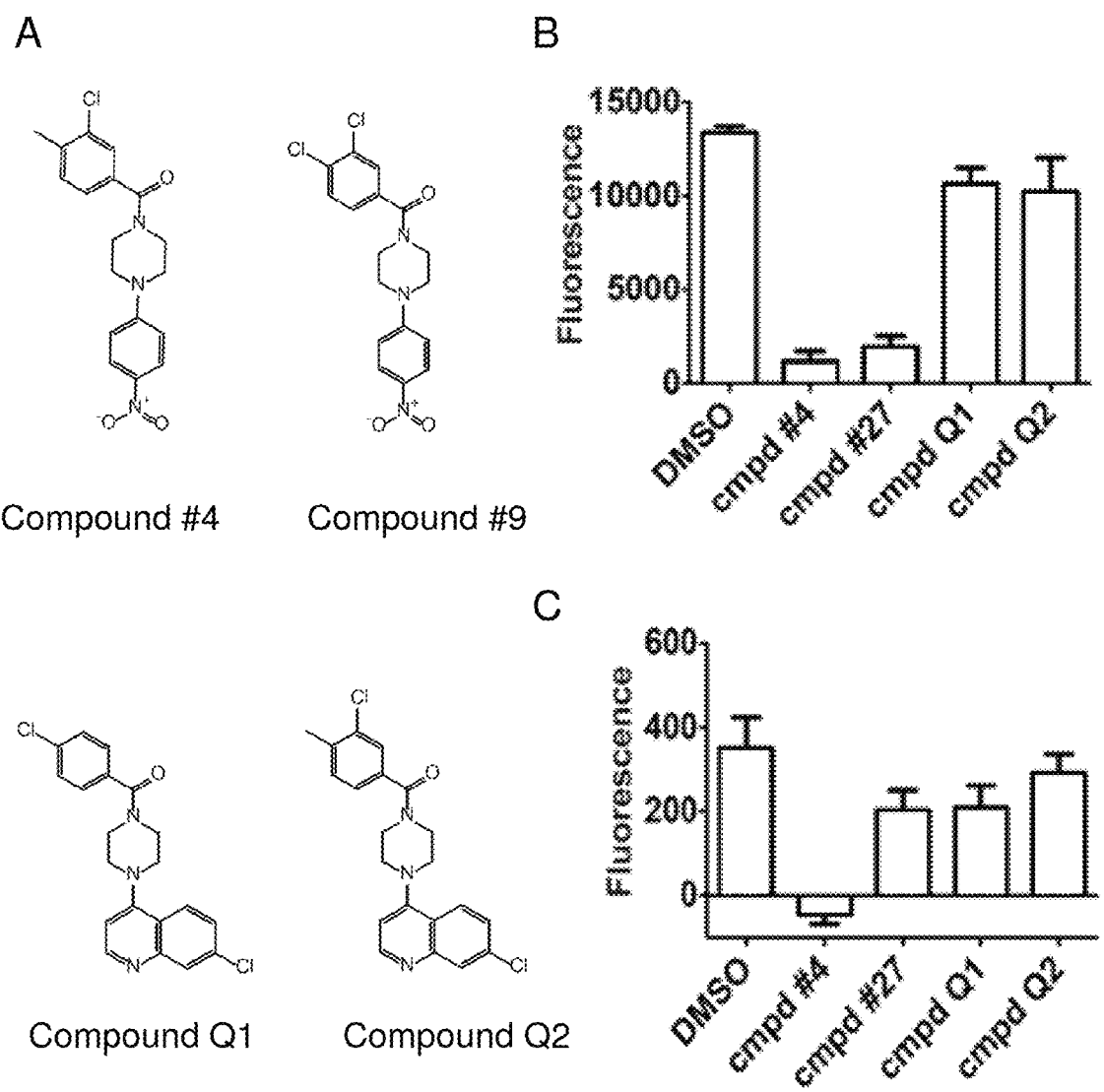
FIGS. 3A-3C. Compound #4 has distinct activities from structurally related piperazinyl quinolones.
Figure 4A:
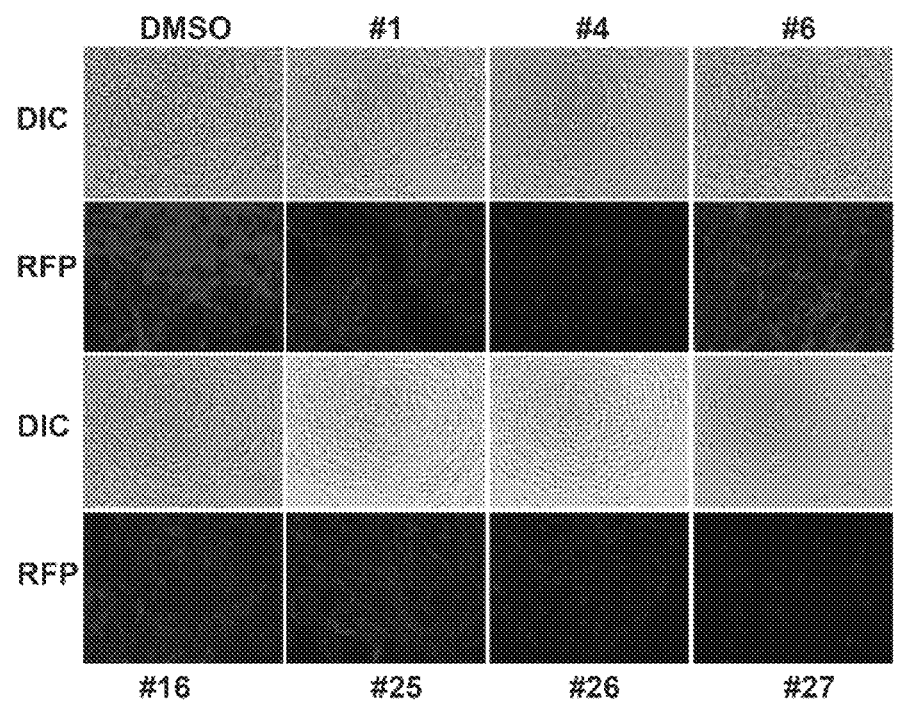
FIGS. 4A-4B. Chemical modulation of Candida albicans morphogenesis.

Visual inspection of cells remaining at the end of adhesion assays suggested that some of the candidate compounds inhibit germ tube formation and generation of hyphae. Because the ability to interconvert between yeast and hyphal morphologies is usually correlated with pathogenicity (Finkel, 2010), we explored this observation in more detail. First, we assessed the effect of our compounds on the induction of hyphae by "Spider" media (Chauhan, 2009). For this experiment, we used a strain that contains the hyphal-specific HWP1 promoter to the Red Fluorescent Protein (RFP) open reading frame (Ganguly, 2011), which provides a molecular reporter for hyphae formation that we used in addition to visual examination of cell morphology. We initially tested each of the compounds that inhibit adhesion to polystyrene (FIG. 1B), as well as compounds #9, Q1 and Q2 (FIG. 3A), at concentration of 12.5 µM. We observed that compounds #4, 9, 12, Q1, and Q2 most potently inhibited hyphal formation and induction of RFP (FIG. 4A). Compounds Q1 and Q2 share a "Scaffold 1" backbone with compounds #4 and #9, but contain a quinoline group (FIG. 3A). Therefore, the compounds with a quinoline group can inhibit hyphae formation, but not adhesion to polystyrene or human cells (FIG. 3). In contrast, other "Scaffold 1" compounds, e.g., #1, 3, 7, and 8 did not block hyphal formation as efficiently as did #4, 9, Q1, Q2. Additionally, multiple chemical backbones are able to inhibit hyphae formation, because compound #12 has a "Scaffold 2" backbone (Table 2). To better discriminate the inhibitory compounds, we tested #4, 12 and Q1 at lower concentrations. At 10 µM, all three of these completely blocked the hyphae formation induced by Spider media (FIG. 4B). A few hyphae were observed at 5 µM in the presence of compound #12, and hyphae were detectable in the presence of any of the three compounds at 2.5 µM. We conclude that compounds #4, 12 and Q1 all potently inhibit hyphal formation, although these compounds behave differently in adhesion assays (FIGS. 1 and 2). Furthermore, as in the polystyrene adhesion assay (FIG. 8), compound #4 is effective at inhibiting hyphae formation at concentrations >2.5 µM.

Example 5

Several Compounds Inhibit *Candida* Biofilm Formation on Silicone Mesh

Fungal biofilm formation on implanted medical devices is a serious medical problem because these biofilms can lead to life-threatening systemic infections. An established in vitro assay to study device colonization makes use of silicone mesh as a surrogate surface (Nobile, 2006). We tested how the compounds that affected polystyrene adhesion (FIG. 1) would affect biofilm formation by visual inspection of the biofilms formed, by measuring the optical density of the supernatant liquid cultures, and by measuring their dry weights. In the presence of DMSO vehicle, we confirmed that wild-type *C. albicans* cells efficiently formed biofilms on the silicone mesh; in contrast, edt1$^{-/-}$ mutant cells did not, resulting in the majority of the cells dispersed throughout the media rather than adhered to the mesh (FIG. 5). Visual inspection suggested that compounds #1, 4, 6, 7, 9, 12, 21, Q1, and Q2 most effectively kept the cells dispersed in the media rather than on the mesh (FIG. 5A). Measurements of the media density (FIG. 5B) generally confirmed these assessments, although the density observed for compound #21 was more modest than for the other compounds tested, perhaps reflecting effects on cell growth. The dry weight measurements (FIG. 5C) indicated that compounds #4 and 9 were most effective at reducing biofilm formation, closely followed by compounds Q1 and Q2. Therefore, compounds #4 and Q1 were effective inhibitors of both hyphal morphogenesis (FIG. 4) and biofilm formation on silicone mesh (FIG. 5).

Example 6

Compound 4 Extends the Lifespan of Nematodes Infected with *C. albicans*

In our in vitro assays, compound #4 displayed the widest range of activities that might impair fungal pathogenesis (FIGS. 1, 2, 4, 5), and was non-toxic to mammalian cells (FIG. 2C). We therefore tested whether compound #4 can alter fungal infections in two in vivo settings. First, we performed pathogenesis assays in which nematodes (*Caenorhabditis elegans*) are infected with *C. albicans*, resulting in killing of the nematode host (Jain, 2009; Okoli, 2009). We used this assay to test whether compound #4 might have a protective effect, exposing *C. elegans* to *Candida albicans* and either DMSO vehicle, the commonly used antifungal drug fluconazole at 12.5 µM, or compound #4 at the same concentration. We observed that both fluconazole and compound #4 increased the lifespan of the infected worms (FIG.

6A). Therefore, consistent with its in vitro activities, compound #4 functions as an antifungal agent in this model infection system.

Example 7

Compound #4 Alters Biofilm Morphology in a Mouse Model of Vulvovaginal Candidiasis As an initial test of compound #4 in a mammalian infection model, we examined a mouse model of vulvovaginal candidiasis (VVC). This system is ideal for evaluating our compounds because VVC infections depend on fungal morphogenesis and biofilm formation (Harriott, 2010). This is a medically important assay system, because VVC affects 75% of all women at least once in their lifetime, and *Candida albicans* is responsible for 85-95% of these infections (Sobel, 1998).

In this assay, excised murine vaginal mucosal tissue is tested as a substrate for infection by *Candida* cells, providing a rapid and simple method for optimizing treatment conditions prior to in vivo infection assays. The other readout in the assay is a measure of the number of viable fungal cells, expressed as colony forming units (CFU). We did not observe significant differences between the CFU recovered from untreated and compound #4-treated samples. Also, in the presence of compound #4, the *Candida* cells still formed a carbohydrate-rich extracellular matrix (ECM), as detected by Concavalin A staining, consistent with our findings with *Candida* cells grown in liquid culture. However, compound #4 modulates the morphology of the *C. albicans* biofilm during ex vivo VVC, as revealed by scanning electron microscopy (SEM; FIG. 6B), with a predominance of individual, yeast-form cells appearing. Therefore, although compound #4 only partially inhibits hyphae formation or ECM production in this system, ultrastructural aspects of the biofilms are altered.

Discussion

Rather than seeking compounds that interfere with the growth or metabolism of pathogenic yeast, or that inhibit an individual enzyme, we sought to isolate compounds that interfere with the initial adhesion events in fungal infections, without bias toward a particular target. To our knowledge, there has not to date been a published screen that directly targets the adhesion process. By targeting the adhesion step, our screen required removal of unbound cells. Although laborious in a high throughput setting, this extra effort allowed us to detect a class of compounds that have unique properties. Importantly, because the assays we describe here are based on altering the behavior of intact cells, we avoided the complication of compounds unable to cross the cell wall and/or membranes.

Here, we report a small molecule screen has lead to discovery of several compounds that display multiple activities related to fungal pathogenesis. In particular, compound #4 inhibits fungal adhesion to polystyrene and human cells (FIGS. 1 and 2), hyphal morphogenesis (FIG. 4), biofilm formation (FIG. 5), and pathogenesis in a worm infection model (FIG. 6). Notably, inhibition of hyphal morphogenesis occurs in liquid culture in the absence of adhesion, suggesting that compound #4 affects multiple cellular processes. The effects on morphology were not selected in our primary screen, demonstrating the need for multiple assays to characterize our candidate compounds fully.

Figure 4A:
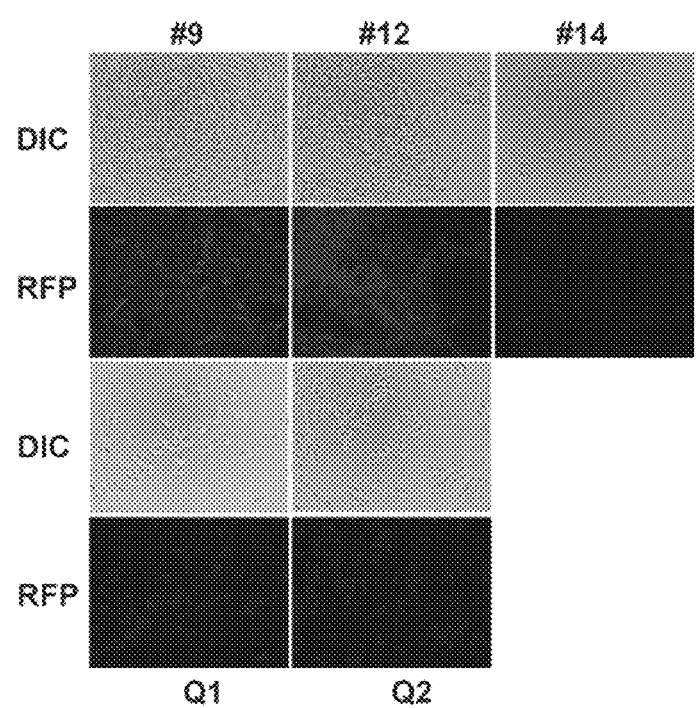
Figure 4B:
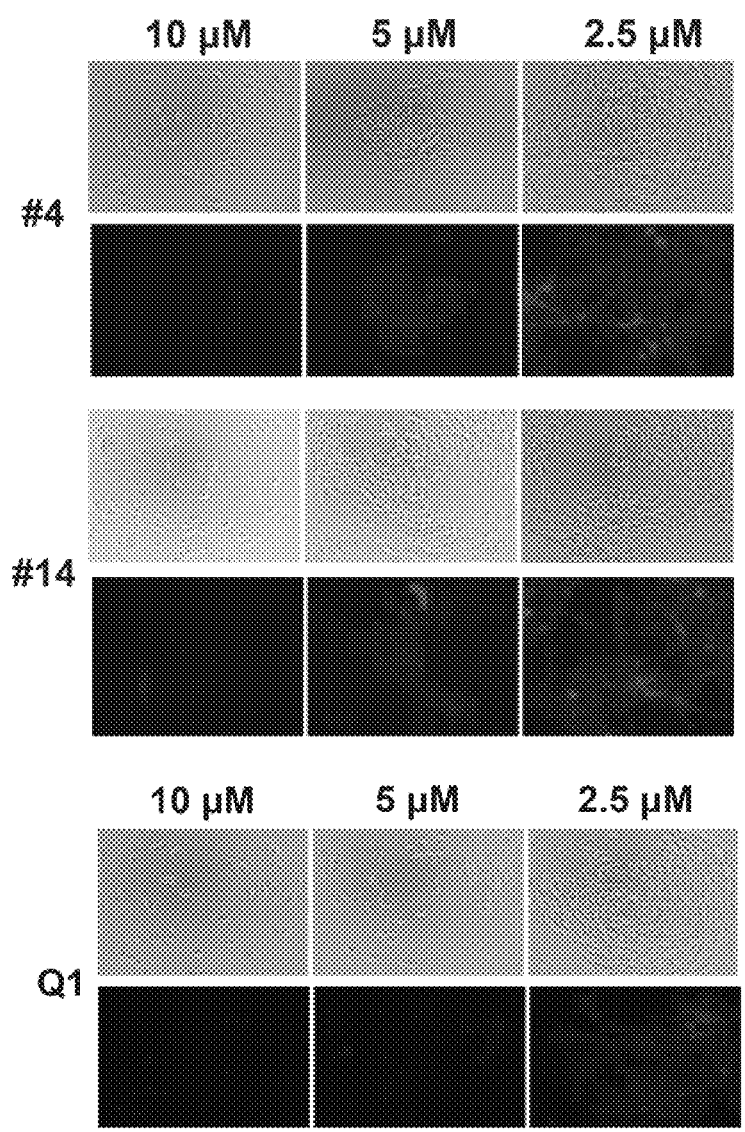
Figure 5:
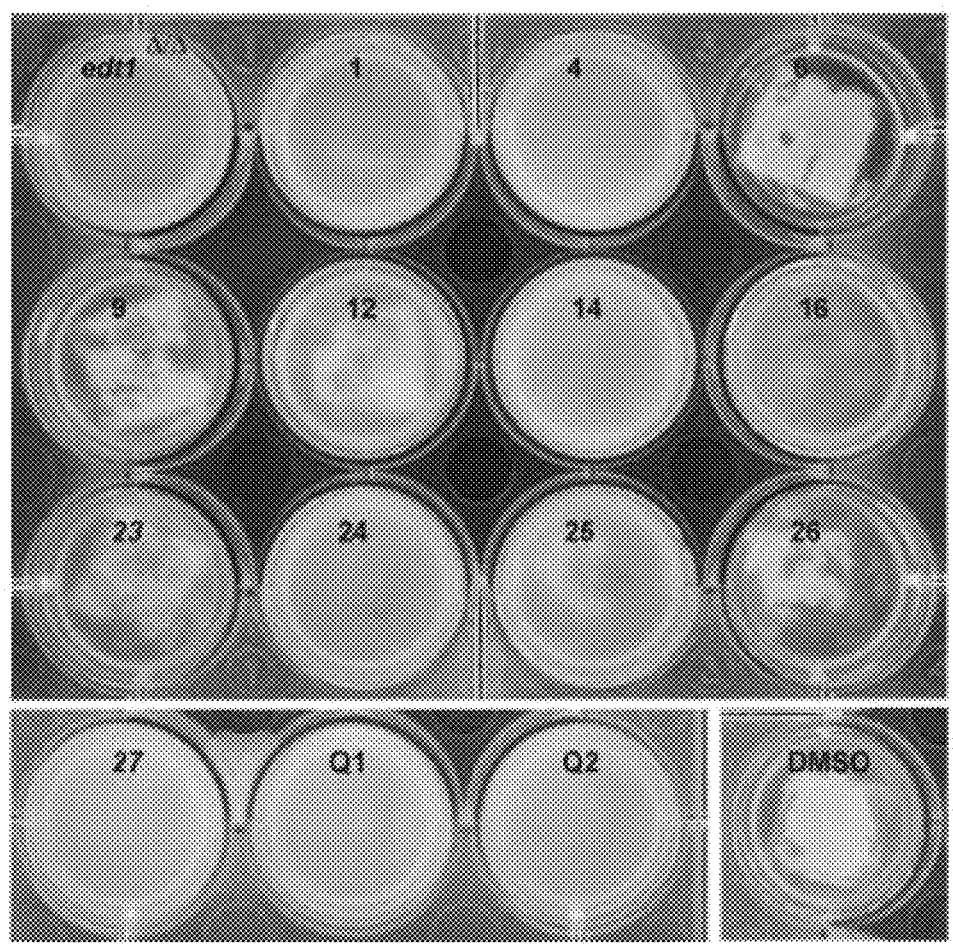
FIGS. 5A-5C. Effect of small molecules on biofilm formation in vitro.
Figure 6:
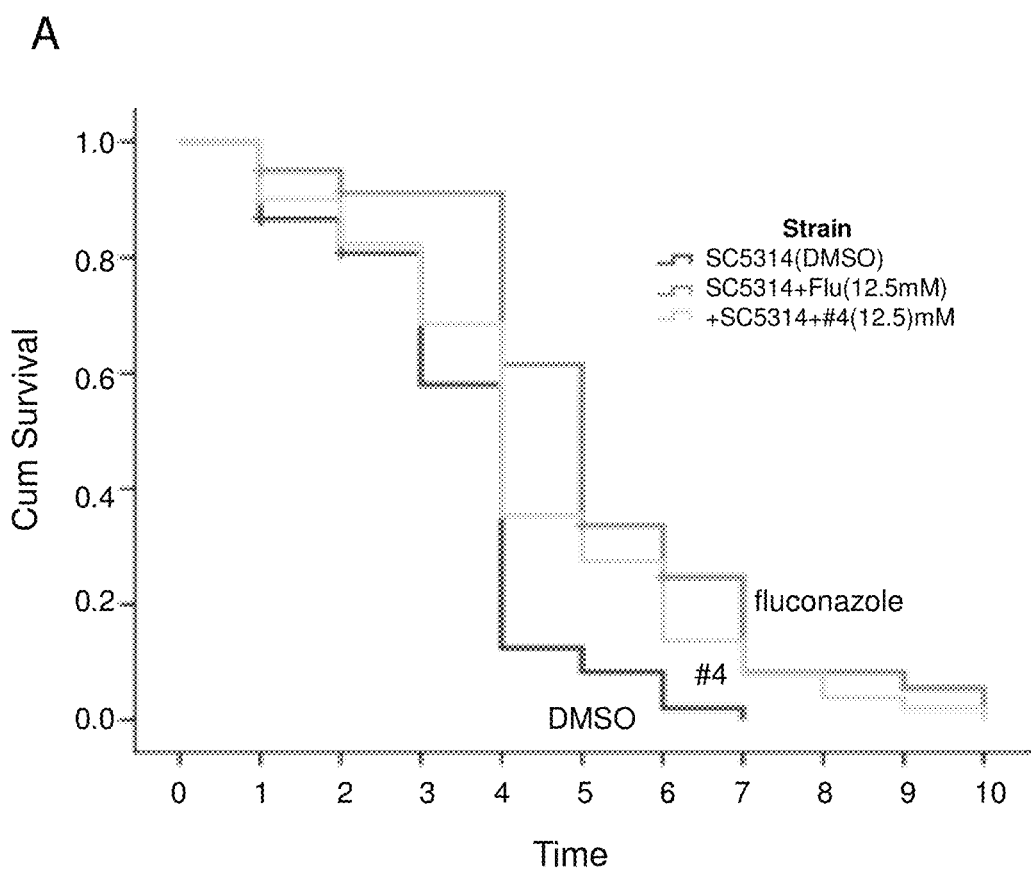
FIG. 6A-6B. Effects on metazoan hosts.
Figure 6:
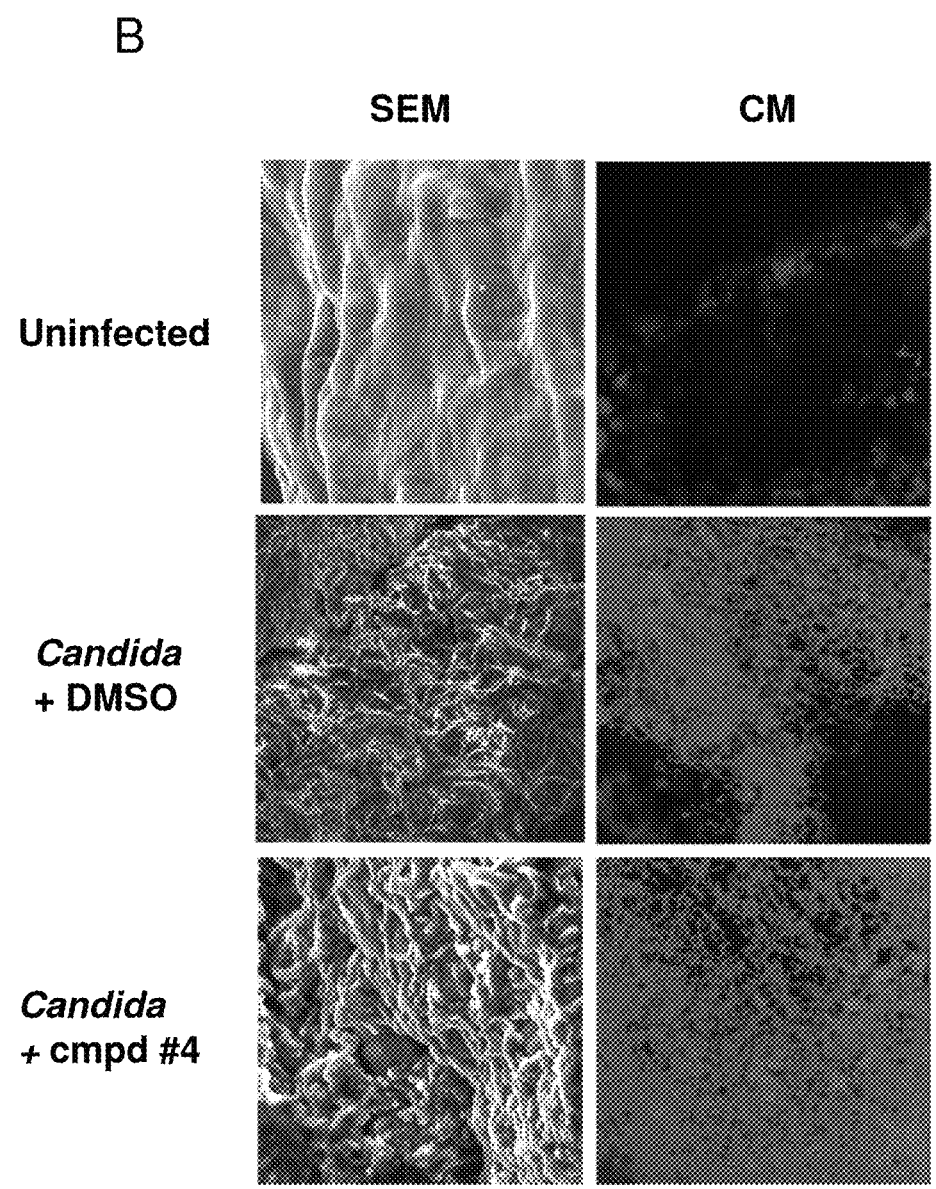

We find that small changes in the compounds can lead to different combinations of activities (FIGS. 3-5). This was most pronounced in the comparison of compounds #4 and 9, which differ by the substitution of a methyl group for a chlorine substitution on one aryl ring (FIG. 3; Table 1). Compound #4 but not #9 effectively inhibited human cell binding, but these two compounds shared the ability to inhibit polystyrene binding (FIG. 3), hyphae formation (FIG. 4), and biofilm formation (FIG. 5). As another example, the quinoline ring-containing compounds Q1 and Q2 do not inhibit polystyrene binding or human cell binding, but do inhibit hyphae formation or biofilm formation.

Several previous experiments suggest a strong link between hyphal morphogenesis and fungal pathogenesis. For example, experiments with a doxycycline-inducible transcription factor (NRG1) that governs hyphae formation have shown that the ability to form hyphae is continually required for the lethality associated with systemic candidaisis (Saville, 2003). Likewise, many mutants defective in hyphae formation are non-pathogenic (Lo, 1997), although this correlation is not absolute (Noble, 2010). We observed that compound #4 inhibits hyphae formation in liquid culture (FIG. 4), reduces fungal pathogenesis in a nematode model (FIG. 6A), and alters biofilm morphology in an ex vivo mammalian mucosal infection model (FIG. 6B).

Materials and Methods

Strains and Growth Conditions.

The *C. albicans* strains used were the wild-type clinical isolate SC5314 (Gillum, 1984), SC5314-derived edt1$^{-/-}$ cells that lack an adhesion protein (see Table 2 of Wheeler, 2008), or their respective GFP-expressing derivatives (Wheeler, supra). The SGH284 strain was used as a hyphal reporter strain; this contains the red fluorescent protein (RFP) gene under the control of the endogenous, hyphal-specific HWP1 promoter (Ganguly, 2011). Other fungi analyzed included *C. tropicalis*, *C. dubliniensis* (Moran, 1997), and fluconazole-resistant clinical isolates of *C. albicans* from AIDS patients (Bachmann, 2002). *Saccharomyces cerevsiae* W303 (Thomas, Rothstein) was used to measure the effects of compounds on liquid growth.

The *C. elegans* wild type strain N2 was grown at 20° C. on nematode growth agar medium (NGM) spotted with *Escherichia coli* OP50 and maintained as described previously (Brenner, 1974). *E. coli* OP50 was grown overnight in Luria broth at 37° C.

Screen for Small Molecule Adhesion Inhibitors.

Two days before each set of assays, one 5 ml culture of SC5314 cells and two 5 ml cultures of edt1$^{-/-}$ cells were inoculated with single colonies in SC+0.15% glucose media, and grown overnight with shaking at 200 rpm at 30° C. The next day, these starter cultures were used to inoculate 100 ml cultures for each strain, grown under the same conditions. The next day, OD at 600 nm was measured for both cultures. Cells were pelleted at 3000×g and resuspended in fresh SC+0.15% glucose media to a final concentration of 0.5 OD/ml. 200 μl/well of 0.5 OD/ml edt1$^{-/-}$ cells were added to the first column of each 96 well Immulon 2HB flat bottom microtiter plate (Part No. 3455, Thermo Scientific), and 200 μl/well of 0.5 OD/ml SC5314 cells were added to the remaining columns. This was followed by robotic addition of 2 μl of DMSO vehicle to columns 1 and 12; compounds from the UMASS Medical School Small Molecule Facility DIVERset library (Chembridge) at a stock concentration of 5 mM were added to columns 2-11 (FIG. 1A). The wells were mixed by robotic pipetting three times, yielding a final compound concentration of 50 μM. The plates were covered with foil and incubated at 37° C. for 4 hours. The contents of the wells were then decanted and 50 μl of 0.5% crystal violet (Sigma) in water were added to each well. The plates were covered again and incubated at room temperature for 45 minutes. The dye was removed by decanting, and the plates were gently rinsed by ten rounds of submersion in an ice bucket filled with distilled water, followed by decanting the water. The water in the bucket was changed after the fifth wash. The plates were then gently inverted onto a paper towel to remove excess water. 200 µl of 75% methanol were then added to each well. The plates were incubated for 30 minutes at room temperature and then absorbance at 590 nm was measured.

Chemical Screen Data Analysis.

Because of plate-to-plate variability in the magnitude of the signal for the DMSO control wells, we normalized the data. For each plate, the mean $A_{590}$ value from column 1 was set to 0, and the mean $A_{590}$ value from column 12 was set to 1.0, with each experimental well value normalized to these controls. Normalized values from the entire screen were then ranked. Forty compounds yielded a normalized value <0.25, that is, >75% inhibition of adhesion. Many of these compounds fell into two structural subclasses we termed "Scaffolds 1 and 2" (Tables 1 and 2). We reordered 26 of these compounds (Chembridge) for further characterization, omitting highly similar ones. Statistical analyses were carried out using Graphpad Prism5.

GFP-Based Adhesion Assay.

SC5314-GFP and edt1$^{-/-}$-GFP strains were pregrown overnight in SC+0.2% glucose media at 30° C., diluted into fresh SC+0.2% glucose media to a final concentration of $5\times10^6$ cells/ml (equivalent to 0.5 $OD_{600}$/ml) and plated onto Immulon 2HB 96-well plates, with each well receiving 0.1 OD of cells. DMSO or compounds resuspended in DMSO were added to the desired final concentration (1% vol/vol of DMSO was maintained). Plates were then incubated for 4 hours at 37° C. Media was the decanted and plates were washed 3 times with PBS using a MicroFill microplate dispenser (BioTek) with each well receiving 100 ml of PBS. Fluorescence was measured using a Synergy HT plate reader (BioTek) following addition of 100 ml of PBS/well. For each experiment, untagged SC5314 was analyzed simultaneously to determine background fluorescence that was subtracted from the signal from each well.

AlamarBlue-Based Adhesion Assay.

Overnight cultures of SC5314 and edt1$^{-/-}$ cells were grown and plated onto Immulon 2HB 96-well microtiter plates and treated with small molecules as described above. Following incubations, media was decanted and plates were washed twice with 100 µl/well PBS. alamarBlue (Life Technologies) was resuspended to a final concentration of 5% in RPMI buffered with 0.165 M MOPS and then 100 µl was added to each well, followed by further incubation for 2 hours at 37° C. Fluorescence signals at 555Ex/585Em were read using a SpectraMax M5 Plate reader (Molecular Devices).

Epithelial Cell Binding Assay.

Human lung epithelial A549 cells (Giard, 1973) were grown to confluence on Nunc 48 well plates in RPMI+10% FBS and Penicillin/Streptomycin. Media was decanted and plates were carefully washed 3 times with PBS to remove unbound cells. Pre-grown overnight cultures of SC5314-GFP and edt1$^{-/-}$-GFP C. albicans cells were resuspended in fresh SC+0.2% glucose at 0.5 OD/ml and 250 µl of yeast suspension were plated onto to each well. Following incubation at 37° C. for 1.5 hours, media was decanted, and the monolayers were washed carefully 3 times with 250 µl PBS. Fluorescence from bound yeast was measured (485 Ex/535 Em) using the Synergy HT plate reader (BioTek) after addition of 100 µl PBS/well.

Filamentation Assays.

Overnight cultures of SC5314 or SGH584 were pregrown in uridine-supplemented SC media at 30° C. to an OD600>13 and diluted 1:10 into prewarmed Spider medium (1% Peptone (Difco), 1% Mannitol (Sigma) and 0.2% $K_2HPO_4$ (Sigma) (Chauhan, 2009) in glass tubes and grown for 16 hrs at 37° C. shaking at 200 rpm in the presence or absence of drugs as indicated. DIC and fluorescence images were acquired using a Zeiss Axiovert 200 inverted microscope equipped with a Qicam 12-bit Fast 1394 digital CCD camera (Qimaging). Image acquisition was carried out using Openlab 5 software (Improvison).

Fluconazole Synergy Assays.

Assays to test for synergies between compound #4 and fluconazole were performed as described (Youngsaye, 2011, supra), except we used a 96-well rather than a 384-well format. Overnight cultures of fluconazole-resistant strains were resuspended in RPMI 1614 media buffered with 0.165 M MOPS supplemented with Pen/Strep (Gibco), amino acids (Leu, Trp, Arg, H is) and uridine. Cells were seeded into 96-well plates with each well receiving $6\times10^3$ cells and incubated for 48 hrs at 37° C. in humidified incubator. The media was removed and replaced with fresh medium containing drugs at the indicated concentrations. At the end of 24 hours of incubation, viability was evaluated without washing steps, using alamarBlue as previously described (Youngsaye, 2011, supra).

*Saccharomyces Cerevisiae* Growth Rate Analysis.

Overnight cultures of *S. cerevisiae* were diluted to 0.1 OD/ml in fresh YPD and grown in a 30° C. shaker at 200 RPM in the presence of 50 mM of compounds or 1% DMSO. OD 600 nm was measured during the time course to evaluate growth rate.

Measurement of Toxicity of Compound #4.

A549 cells in RPMI+10% FBS were seeded into 24-well plates at $1\times10^5$ cells/well and grown overnight at 37° C. Media was removed and replaced with fresh media containing indicated concentrations of compound #4 or 1% sodium azide, followed by incubation for 24 hrs. Viability was determined with 5% alamarBlue as above.

Biofilm Formation on Silicone Elastomers.

We adapted a published method (Nobile, 2006, supra). Autoclaved, pre-weighed silicone mesh squares (Bentec, Catalog Number PR72034-04N) were incubated overnight at 37° C. with undiluted bovine serum. Following washing with PBS, the squares were transferred to 12-well plates and incubated with 0.5 OD/ml SC5314-GFP cells in Spider medium (with or without drugs as indicated), for 90 min at 37° C., shaking at 200 rpm. Squares were washed in PBS and transferred to new 12-well plates containing fresh Spider medium with fresh drugs and incubated for 60 hrs in a 37° C. shaker at 200 rpm. The plates were then photographed, the liquid media were collected for $A_{600\ nm}$ measurements, and the dry weights of the bound biofilms were measured following drying of the silicone squares in a chemical hood.

*C. elegans* Egg Preparation.

Three worms in the L3/L4 stage were transferred to each of two NGM agar plates containing *E. coli* OP50 and grown at 20° C. for four days. On the day of the experiment, worms were washed off the plates with M9 buffer and centrifuged at 900×g for 2 min. The supernatant was removed, and the worms were then resuspended in a bleach solution (1:4 dilution of commercial bleach (5.25%) diluted in 0.25 M sodium hydroxide). The worm suspension was mixed gently by inversion for 3 min, and centrifuged for 2 min at 2,000×g. The pellet containing the eggs was washed with M9 buffer and centrifuged at 2,000×g for 2 min and then resuspended in 500 µl M9 buffer. The egg suspension was diluted or concentrated with M9 buffer as required to obtain approximately 30-40 eggs/5 µl.

C. elegans Pathogenesis Assay.

E. coli and Candida strains were grown overnight at 37° C. Culture aliquots were centrifuged at full speed for 1 minute in a table top microcentrifuge and the supernatant was removed. Pellets were washed twice in sterile deionized water, and finally resuspended to a final concentration of 200 mg/ml and 10 mg/ml, respectively. A mixture of 10 µl of a 50-mg/ml streptomycin sulfate stock, 7 µl of distilled water, 2.5 µl E. coli and 0.5 µl of Candida was spotted on to each NGM plate. Drugs in a final concentration of 12.5 µM were added to the mix. E. coli spotted plates were used as a control. Finally, 5 µl of C. elegans egg suspension was transferred to each plate. Plates were then kept in a 20° C. incubator and were observed over next 5 days. All the experiments were done in triplicate. Student t-test was used to check the statistical significance of the differences observed between wild type and other Candida strains.

Mouse Mucosal Infection Studies.

These ex vivo infections were performed as described (Harriott, 2010).

Example 8

By screening a chemical library, we have identified small molecules that inhibit adhesion of C. albicans to polystyrene surfaces. Notably, one of these compounds, which we term "compound #4" for brevity (Table 1), also inhibits binding of C. albicans to cultured human epithelial cells. Moreover, compound #4 also inhibits the C. albicans yeast-to-hyphal morphological transition, and biofilm formation on silicone mesh. Furthermore, this compound impairs C. albicans pathogenesis in a nematode infection model system, and alters fungal biofilm morphology in a mouse mucosal infection assay. Therefore, this compound has multiple activities as a novel antifungal therapeutic.

Compound #4, and a related compound termed "compound #9" (Table 1), is also able to coat plastic surfaces, making the surfaces more resistant to subsequent fungal colonization. Furthermore, compound #4 can pretreat Candida cells to make them less adhesive. These data show that compound #4 and related compounds can be used as therapeutics to treat candidiasis and in antifungal coatings for implanted medical devices.

Figure 11:
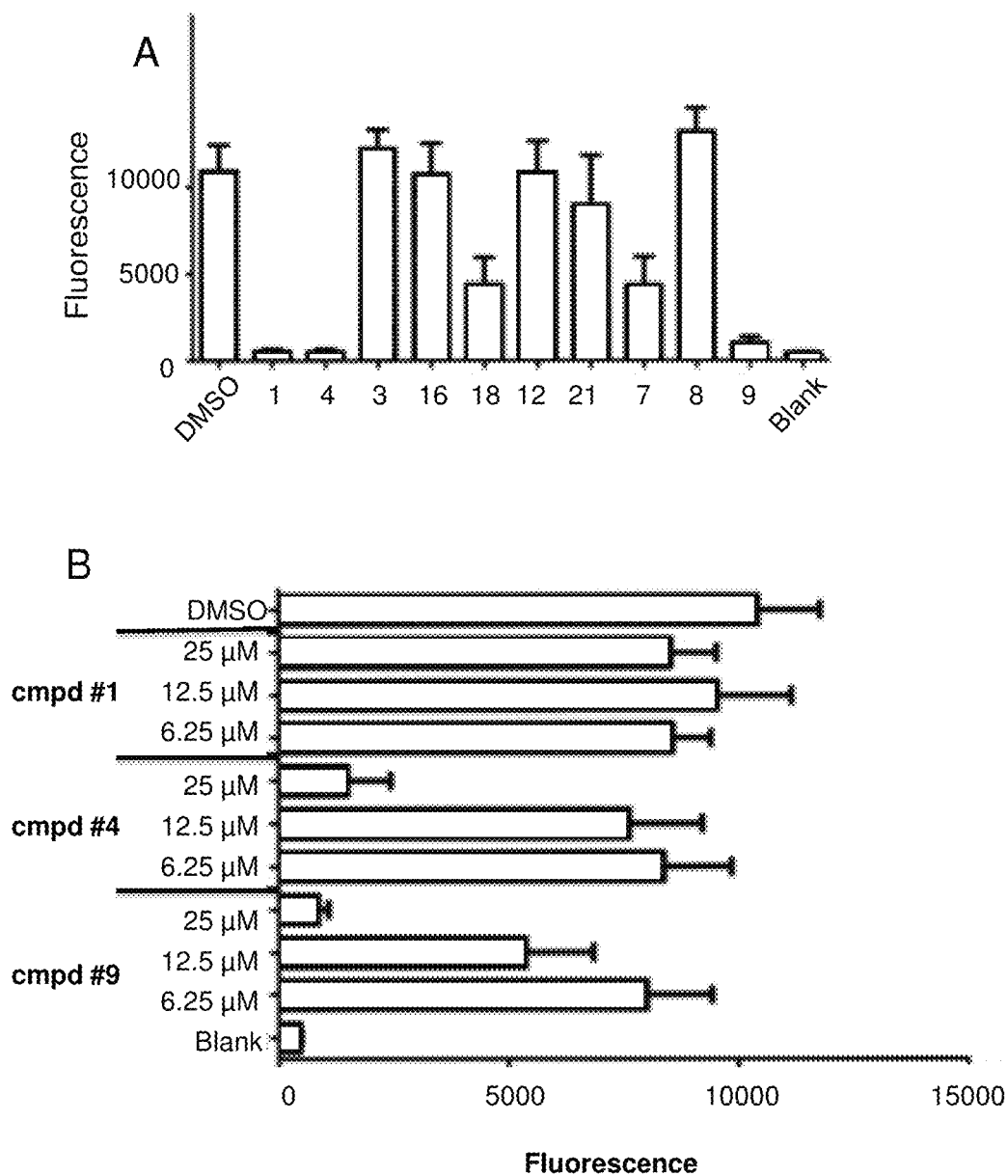
FIGS. 11A-11D. Compound #4 can coat surfaces and reduce subsequent fungal adhesion.

Because compounds #4 and #9 contain a nitrophenyl group (FIG. 3A), solutions containing these appear yellow. We noticed that solutions containing these compounds leave a yellow coating on polystyrene surfaces, suggesting that these compounds may inhibit fungal adhesion at least in part via surface interactions. To test this idea, we preincubated polystyrene plates with each of the compounds that affect adhesion to polystyrene, washed to remove unbound compound molecules, and then added C. albicans cells to measure adhesion without further addition of compound. At a concentration of 50 µM, we observed that compounds #1, 4, and 9 (Table 1) efficiently inhibited subsequent adhesion of C. albicans (FIGS. 3B and 3C and FIG. 11A). Notably, these three compounds all share a similar chemical scaffold and contain a nitrophenyl group, which is absent in all compounds tested here that lack pre-coating ability (FIG. 3A). This suggests that the nitrophenyl group is critical for this activity.

To distinguish the three pre-coating compounds, we then titrated them in this pre-coating assay (FIG. 11B). We observed that compound #1 was ineffective at concentrations of 25 µM or below; in contrast, compounds #4 and 9 displayed similar dose response curves, being strongly inhibitory at 25 µM but much less so at 12.5 µM or below. We also tested whether compound #4 could affect fungal adhesion when it was used to pre-coat C. albicans cells rather than the polystyrene surface. Using either alamarBlue or encoded GFP to detect adhesion (FIGS. 11C and 11D), we observed that compound #4 could reduce adhesion of pre-treated cells, although this effect was less effective than co-incubation of the compound with the cells and the substrate surface. We conclude that compound #4 has the ability to make polystyrene and the C. albicans cell surface less amenable to subsequent adhesion.

Rather than seeking compounds that interfere with the growth or metabolism of pathogenic yeast, or that inhibit an individual enzyme, we isolated compounds that interfere with the initial adhesion events in fungal infections, without bias toward a particular target. To our knowledge, there has not to date been a published screen that directly targets the adhesion process. Because biofilms formed by pathogenic yeasts are intrinsically more resistant to many of the available antifungal agents (Finkel, Nat. Rev. Microbiol. 9:109-118, 2011), reduction of biofilm formation via adhesion inhibition is an attractive and previously unexplored route towards novel therapeutics and/or medical device coatings.

Efficient adhesion is required for formation of aggressive biofilms, which in turn make Candida a successful pathogen (Finkel, supra). Therefore, adhesion is a pivotal step in fungal pathogenesis, but one that has not to our knowledge been targeted in previous small molecule screens. We have shown in preliminary studies that detection of compounds that prevent adhesion of Candida albicans to polystyrene surfaces can be done in a high throughput manner. By targeting the adhesion step, our screen (described below) requires removal of unbound cells. Although this is more complex than previous screens that only measure metabolism, this extra effort allowed us to detect a class of compounds that have unique properties. Importantly, because the assays in this proposal are based on altering the behavior of intact cells, we avoid the complication of compounds unable to cross the cell wall and membranes.

Although our primary screen did not require this property, we have isolated compounds that not only interfere with fungal adhesion but also cause pretreated surfaces to be less easily colonized by fungal cells. This property has important possibilities for effectiveness on the surface of implanted medical devices, which is a major site of infection that can lead to dangerous systemic candidaisis. To our knowledge, this is a novel combination of functions for small molecule antifungal compounds.

Example 9

Methodology for High-Throughput Screening for Compounds that Affects Fungal Adhesion and Identification of Primary Candidates The following assay provides, as a primary compound screen, a high throughput assay to identify chemicals that inhibit fungal adhesion, a necessary first step to infection. Furthermore, efficient adhesion is required for formation of aggressive biofilms (Blankenship et al., Curr. Opin. Microbiol. 9:588-594, 2006), which in turn make Candida a successful pathogen (d'Enfert, Curr. Opin. Microbiol. 12:358-364, 2009). Therefore, chemicals that attenuate adhesion have the potential of being good antifungal agents. The assays described herein is based on altering the behavior of intact cells and avoid the complication of compounds unable to cross the cell wall and membranes.

The multi-well plate reader and a robotic liquid handling system used for these studies was provided by The Small Molecule Screening Facility at UMMS. This Facility has a chemical library (DIVERSet) with 30,000 compounds that was purchased from ChemBridge Corporation. This is a diverse collection of drug-like small molecules from a company that supports prompt "hit" re-supply with 99.8% availability. The set is rationally selected to cover the broadest part of biologically relevant pharmacophore diversity space. It is available in a 96-well pre-plated DMSO format.

Figure 12:
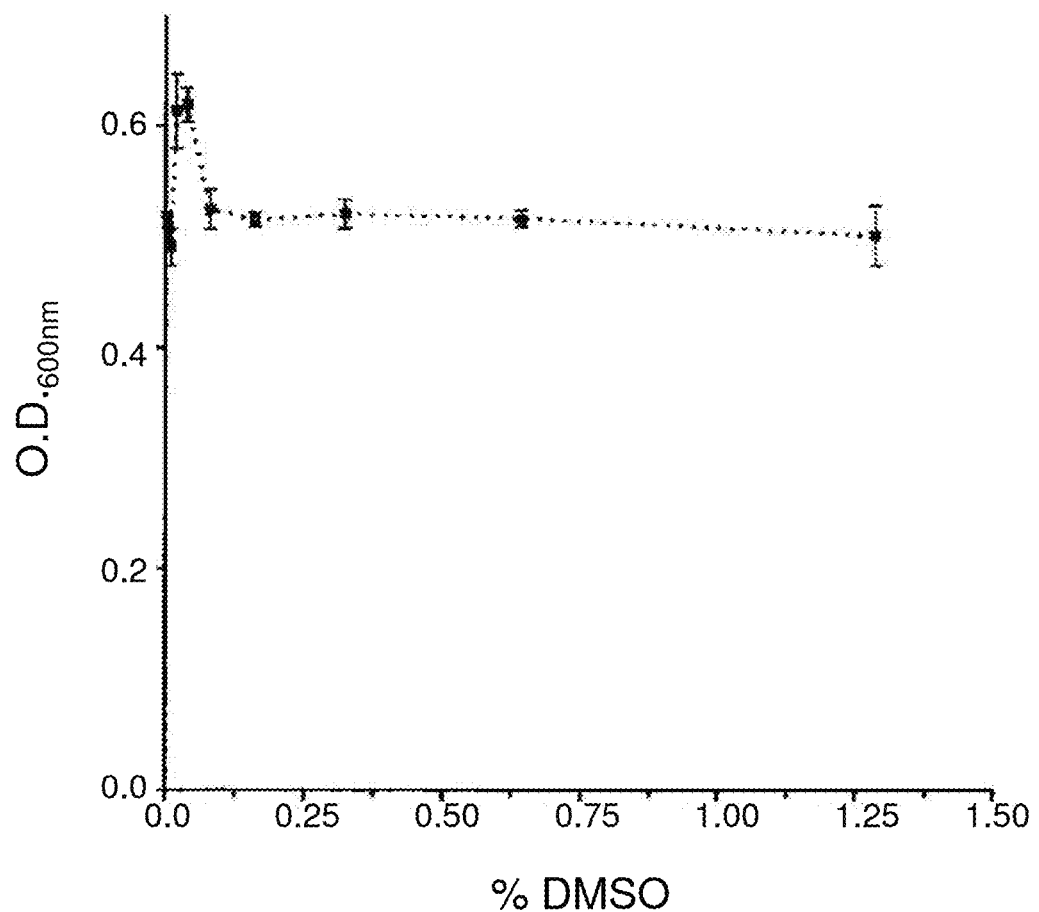
FIG. 12. Growth of Candida albicans in 96-well plates in presence of DMSO. $5\times10^3$ cells were inoculated into 0.1 ml rich (YPD) media in the presence of the indicated concentration of DMSO and grown at 25° C. for 16 hours. Triplicate cultures were analyzed via a microplate reader.

The compounds in this library are at 5 mM concentration in DMSO, and the minimal accurate pipetting volume of the robot in the facility is 1 µl. Therefore, in 200 µl cultures pipetted into 96-well plates, addition of 2 µl from the library results in an initial compound concentration of 50 µM, and a final DMSO concentration of 1%. Importantly, we have established that this concentration of DMSO is tolerated by Candida (FIG. 12).

Our criterion for optimization of the screen will be the Z-Factor (Zhang et al., *J. Biomol. Screen* 4:67-73, 1999), a statistical assessment of the quality of the assay based on the standard deviations of the measured signal from the positive and negative controls. Z gives a quantitative assessment of how well distributed and reproducible the data are. A Z-factor value between 0.5 and 1.0 is considered a robust assay.

Adhesion Assay: Crystal Violet Detection.

Yeast cells grown in low glucose culture are known to efficiently bind to polystyrene surfaces via adhesive cell surface proteins that are required for mammalian host cell infection (Reynolds and Fink, *Science* 291:878-881, 2001; and Cormack et al., *Science* 285:578-582, 1999). The protocol for our adhesion assay has been expanded to high throughput applications using liquid handling robots from known assays (Reynolds, supra; and US 2002/0160444). The reagents are safe, inexpensive and readily available. We have titered the following volumes, concentrations and incubation times to get the most reliably high Z factor:

Candida Cell Culture:

Overnight cultures of *Candida* strains are grown in synthetic complete media (SC)+0.9% glucose at 30° C. Absorbance will be measured at 600 nm to monitor growth. In the morning, a cell suspension ($A_{600}$ of 0.5/ml) is prepared in fresh SC+0.9% glucose.

In Vitro Robotic Screen:

We dispense 200 µl of the *Candida* cell suspension into the wells of flat-bottom polystyrene 96-well plates. Compounds from the UMMS library (or DMSO in negative control wells) are added at 2 µl/well, followed by thorough mixing via robotic pipetting. Plates are then incubated at 37° C. for four hours, and then the liquid is decanted into a waste container. 50 µl of 0.5% crystal violet dye is added to wells and incubated at room temperature for 45 minutes. Plates are then washed by repeated (10 times) submerging into a water bucket. 200 µl of 75% methanol is added, and $A_{590}$ is measured using a multiwell spectrophotometer after 30 minutes.

Figure 13:
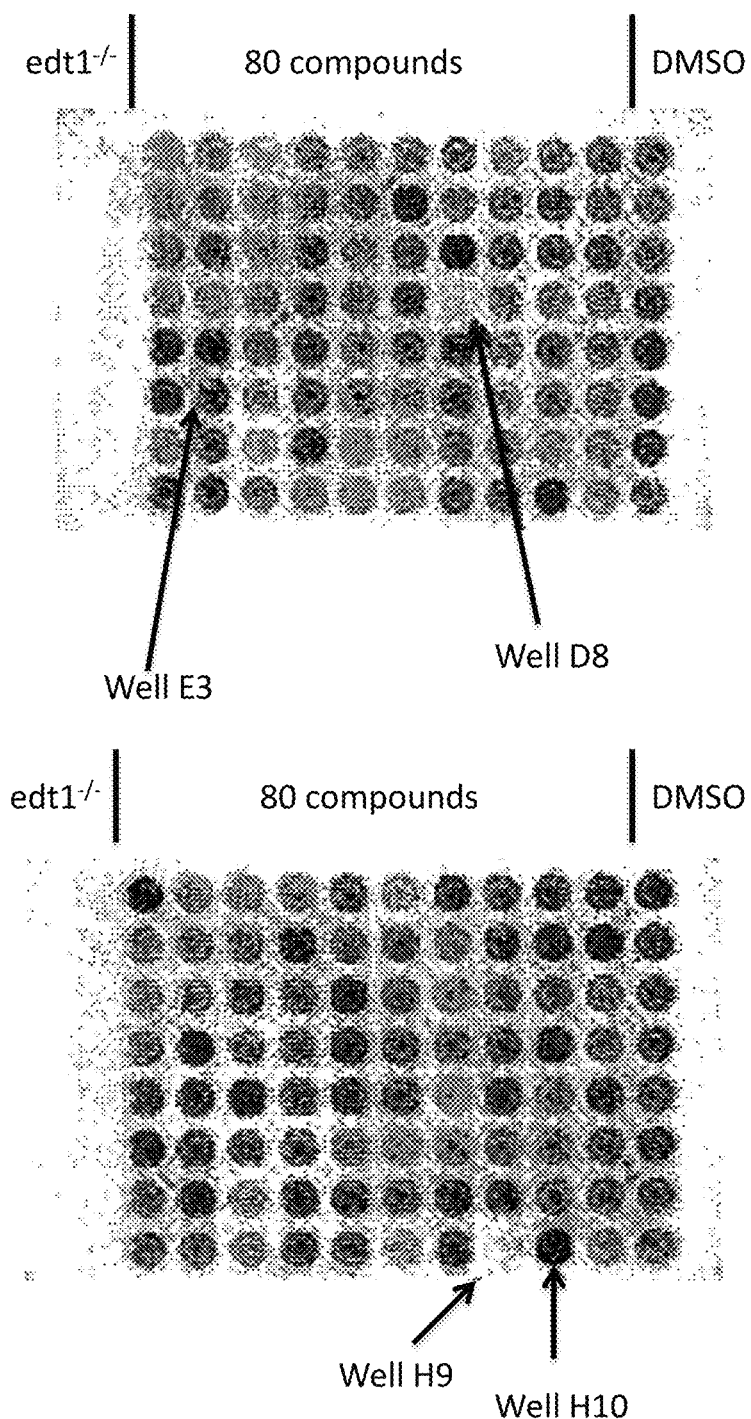
FIG. 13. A high-throughput dye-binding assay for Candida adhesion.

Hit Identification:

Each plate has control wells (FIG. 13). The 96-well plates that house the library of compounds at UMMS are formatted such that the first column and last column contain only DMSO. We used the last column of each plate as a set of positive controls (DMSO only, so 100% adhesion signal will be defined) and first column as negative controls (non-adhesive mutant *Candida* cells added). Each 96-well library plate contains therefore 80 compounds, and a total of 375 plates carry 30,000 compounds.

Results:

We have developed and executed a pilot high-throughput screen for compounds that prevent adhesion of *Candida albicans* to polystyrene surfaces, as a model for the first step in the process of biofilm formation on implanted medical devices. We have made substantial progress toward this goal. First, we systematically tested several variables to optimize the signal-to-noise ratio in the adhesion assay. Briefly, we varied the concentration and number of cells added per well, the duration of the incubation of cells in the 96-well plates, the concentration of detection reagent (crystal violet dye), and washing and development protocols. The most important improvement proved to be the addition of 75% methanol prior to spectrophotometric reading of the plates, which greatly increased the speed and reproducibility of color development. Together, our alterations produced assays that can be completed within a single workday with Z'-factor statistics of ~0.6. These results encouraged us to begin screening the 30,000 compounds in the Small Molecule Screening facility at UMass. Examples of our initial results are illustrated in FIG. 13.

As the crystal violet-based assay became more familiar, we were able to scale up production to forty 96-well plates per day, so that we were able to screen the entire library in under a month. We have identified ~300 wells that displayed absorbance readings <50% of the DMSO-alone vehicle controls. This represents a preliminary hit rate of ~1%, a workable number than can be handled manually in a small number of 96-well plates. Further, many of our hits have structurally similar chemical backbones, defining a small number of subfamilies. These data show that our screen can reproducibly detect specific classes of inhibitor compounds.

Example 10

A *Candida albicans* Mutant Strain and an Enzymatic Assay and for the Development of Antifungal Drugs Posttranslational modifications on histones have important consequences for genome stability and function (reviewed in Rando, 2012, and Bannister, 2011). One prominent class of histone modifying enzymes are histone acetyltransferases (HATs), which transfer the acetyl group from acetyl-coenzyme A (Ac-CoA) to the ε-amino group of a histone lysine residue. Depending on context, histone acetylations can promote appropriate gene expression (Brownell, 1996), chromatin conformation (Shogren-Knaak, 2006), DNA replication (Unnikrishnan, 2010) and DNA repair (Lukas, 2011).

Most histone acetylations occur on the unstructured termini of the core histone proteins. A notable counterexample is acetylation of histone H3 lysine 56 (H3K56), a residue located on the α-helix between the N-terminal tail and the histone fold domain of histone H3. In fungi, H3K56 acetylation (H3K56ac) quantitatively marks newly synthesized, soluble histones, stimulating their association with assembly proteins that deposit them onto DNA (Celic, 2006; Li, 2008; Chen, 2008; Kaplan, 2008; Erkmann, 2009; Zunder, 2012; Su, 2012). Although H3K56ac has been detected in metazoan organisms, it is far less abundant (Yu, 2012; Drogaris, 2012), and therefore does not appear to serve as a quantitative marking system for nascent histones. Indeed, the more important modification of H3K56 in metazoans appears to be methylation, not acetylation (Yu, 2012).

Not only is the function of H3K56ac specific to the fungal Kingdom, but so is the enzyme that creates it. In all fungi studied to date, acetylation of H3K56 is catalyzed solely by the histone acetyltransferase Rtt109 (Schneider, 2006; Han, 2007; Driscoll, 2007; Collins, 2007; Tsubota, 2007; Xhemalce, 2007; Lopes da Rosa, 2010). Notably, H3K56 acetylation is either entirely absent or barely detectable in mammalian cells. Furthermore, despite three-dimensional similarity of Rtt109 to its closest mammalian homologs, the HATs p300/CBP, there is minimal primary sequence similarity, even in the catalytic pockets. Notably, compounds that inhibit p300/CBP do not inhibit Rtt109.

Rtt109 has very limited primary sequence homology to the three well-characterized HAT families: p300/CBP, GNAT (Gcn5-related N-acetyltransferase) and MYST (MOZ, Ybf2/Sas3, Sas2, Tip60). Rtt109 shares the greatest similarity to the mammalian acetyltransferase p300 (Bazan, 2008; Wang, 2008), which is important for N-terminal histone tail acetylations related to transcriptional activation (Chen, 2011). Notably, both Rtt109 and p300 are regulated by stimulatory autoacetylation events (Thompson, 2004; Collins, 2007; Lin, 2008; Stavropoulos, 2008; Albaugh, 2011), and Rtt109 has a similar tertiary fold structure as p300 (Tang, 2008; Stavropoulos, 2008; Lin, 2008). However, the reaction mechanisms of Rtt109 and p300 differ. Rtt109 use a sequential catalytic mechanism (Albaugh, 2010), as observed for other HATs that require formation of a ternary intermediate complex with both histone and AcCoA substrates before catalytic steps can occur (Tanner, 1999; Berndsen, 2007). In contrast, p300 operates a Theorell-Chance ("hit-and-run") mechanism that involves association of the enzyme with acetyl-coA first, followed by transient association with the protein substrate (Liu, 2008). Additionally, previously described HAT inhibitors, including those specific for p300 such as the bisubstrate mimic Lys-CoA, do not affect Rtt109 catalysis (Tang, 2008; Bowers, 2010), and the active sites of these two enzymes display dramatically different electrostatic characteristics (Wang, 2008). Therefore, Rtt109 displays significant differences from its closest mammalian homolog, p300, in terms of both its structure and its biological function.

Rtt109 by itself is a poor enzyme, but can be activated by either of two different histone chaperone proteins, Asf1 and Vps75 (Tsubota, 2007). These cofactors stimulate modification of distinct substrate lysines. For example, Asf1 is required for acetylation of H3K56 by Rtt109 in vivo (Recht, 2006; Schneider, 2006). In contrast, Vps75 stimulates Rtt109 to acetylate H3K9, H3K23 and H3K27 but is not required for H3K56 acetylation in vivo (Berndsen, 2008; Fillingham, 2008; Burgess, 2010), despite its ability to stimulate H3K56 acetylation in vitro (Tsubota, 2007).

Cells of any fungal species that are incapable of acetylating H3K56 are extremely sensitive to DNA damage (Masumoto, 2005; Hyland, 2005; Driscoll, 2007; Xhemalce, 2007; Lopes da Rosa, 2010). We previously demonstrated that deletion of RTT109 in the pathogen Candida albicans dramatically reduces mortality of mice subjected to systemic candidiasis (Lopes da Rosa, 2010). Subsequent studies confirmed that H3K56 acetylation is the crucial function of Rtt109 in C. albicans, because the HST3 gene encoding the deacetylase that removes H3K56ac groups is essential for C. albicans viability, but only if Rtt109 is present (Wurtele, 2010). Notably, the poor pathogenicity of rtt109$^{-/-}$ cells correlates with an inability to withstand phagocyte-generated reactive oxygen species (Lopes da Rosa, 2010), suggesting a mechanistic explanation for the defect in pathogenesis.

In humans, systemic candidiasis results in approximately 40% mortality, despite currently available anti-fungal medications (Gudlaugsson, 2003). C. albicans infections are common in hospital settings, especially on implanted surgical devices and in immune-compromised patients (Pfaller, 2007; Neofytos, 2010). Most clinical drugs used against C. albicans intervene with cellular membrane or wall integrity. Unfortunately, anti-fungal drug resistance is common in this organism, involving changes in membrane synthesizing pathways and rapid efflux of the drugs through cellular membrane pumps (Cowen, 2002; Cannon, 2007). Therefore, discovery of antifungal therapeutics with novel targets is a high medical priority. Because Rtt109 is required for C. albicans pathogenesis and is conserved structurally and functionally only within the fungal kingdom, we reasoned that a specific inhibitor of Rtt109 could provide a novel path to a new class of antifungal therapeutics that would not impair HATs found in mammalian hosts (Lopes da Rosa, 2012).

Small molecules that target the fungal HAT enzyme, Rtt109, but not other HAT enzymes, such as mammalian (e.g., human) HAT enzymes, can be identified using Rtt109 in a screening assay, which is described below. Hence, Rtt109 is a promising novel target for small molecule therapeutic intervention with minimal toxicity to mammalian hosts.

Rtt109 enzymatic activity can be measured in a sensitive microplate assay of defined composition (FIGS. 14A-14F). Thus, a direct inhibitor screen can be conducted using this format.

Biological Demonstration of the Relevance of Rtt109 for Pathogenicity

Figure 15:
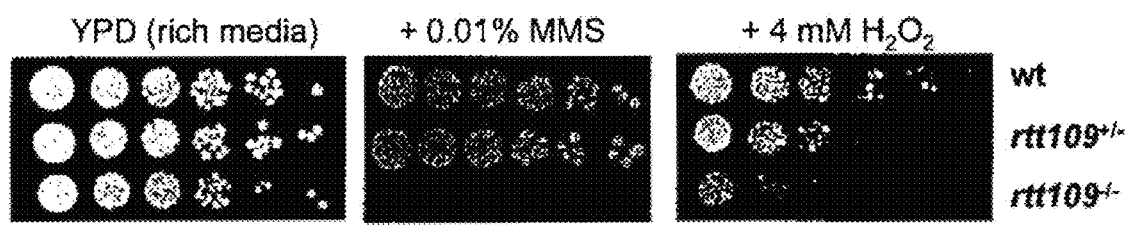
FIG. 15 is a series of photographs showing that Rtt109 is required for C. albicans resistance to genotoxic agents. Five-fold serial dilutions of wild-type, heterozygous (rtt109$^{+/-}$) and homozygous (rtt109$^{-/-}$) deletion strains were plated on rich YPD media, either lacking or containing the DNA alkylating agent MMS, or the oxidant hydrogen peroxide.
Figure 16:
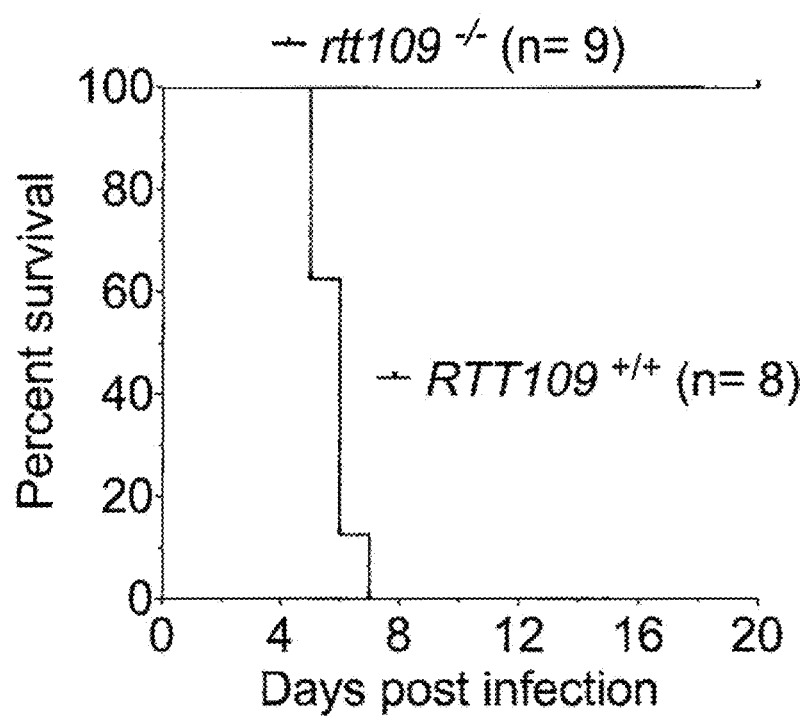
FIG. 16 is a graph showing that rtt109$^{-/-}$ mutants are deficient in causing pathogenicity in the murine candidiasis model. Balb/c female mice were infected with $1.5\times10^5$ yeast cells via venous tail injection.

We have found that homozygous rtt109-1 mutant C. albicans lack H3K56 acetylation and are highly sensitive to genotoxic agents, including methyl methanesulfonate (MMS), camptothecin, and the reactive oxygen species (ROS) hydrogen peroxide (FIG. 15). Notably, ROS-induced stress is part of an antifungal defense mechanism used by phagocytic cells of the immune system. We observe that rtt109$^{-/-}$ mutant cells are less pathogenic in a mouse model of systemic candidaisis induced by tail vein injection (FIG. 16). Together, these data demonstrate that Rtt109 is an important novel target for antifungal therapy.

Development of Rtt109 Histone Acetyltransferase Assays in Multi-Well Plates

Figure 14:
FIGS. 14A-14F. Characterization of a multiwell acetyltransferase assay for Rtt109.

We have purified milligrams of recombinant S. cerevisiae Rtt109 enzyme and its histone-binding co-factor Vps75 from a bacterial expression system; these can be purified separately or as a complex (FIG. 14A). We previously established protocols for purification of milligram quantities of the alternative Rtt109-activating protein, Asf1, and we have purified milligram quantities of recombinant histones H3/H4 in bacteria via an established protocol for use as substrates (Luger et al., Methods Enzymol. 304:3-19, 1999).

We previously characterized histone acetylation by Rtt109 (see Lopes da Rosa et al., Proc. Nat'l. Acad. Sci. USA 107:1594-1599, 2010; incorporated by reference in its entirety). Our published data show that the reaction can proceed efficiently at room temperature, and we have also determined the enzymatic properties and optimal conditions for this reaction, finding that the enzyme has a Km for both its substrates (histones and acetyl-Coenzyme A) in the 1 µM range, similar to other known HAT enzymes. Although we can detect activity by measuring incorporation of radiolabeled acetyl Co-A into the substrate histone, non-radioactive assays are preferred for high-throughput screening. Therefore, we have also developed a quantitative antibody-based assay in which a rabbit polyclonal antisera specific for acetylated H3-K56 is used for detection. Using a commercial vendor, we generated this sera against a synthetic peptide containing an acetylated H3-K56 residue. This antisera displays significant specificity for histone H3 acetylated on K56 as seen in immunoblotting experiments, where the anti-histone H3 reactivity is lost in asf1 mutants that lack H3-K56 acetylation (FIG. 14B). The sera provide sensitive detection at a 1:10,000 dilution, and thus can be used in a 96-well, 100 µl/well format.

We developed a quantitative assay using this sera in an ELISA format, as follows. Reagents for the enzymatic reactions are assembled in a cocktail containing buffer optimal for the reaction (final concentration: 50 mM Tris-Cl, pH 8.0, 1 mM DTT, and 0.1 mg/ml bovine serum albumin (BSA)). Recombinant Rtt109/Vps75 complex, recombinant histones H3/H4 and Ac-CoA are titrated into this mix. Reactions are incubated at 30° C. for 30 minutes, stopped by placing on ice, and distributed to protein-binding 96-well plates for overnight incubation at 4° C. At this point, the protocol is based on standard ELISA protocols. The wells are washed with Tris-Buffered Saline+0.1% Tween 20 (TBST), and blocked with 1% BSA/TBST for 1 hour at 4° C. Wells are then washed three times, and the secondary antibody, commercial horseradish peroxidase (HRP)-conjugated goat anti-rabbit antibodies (GE Healthcare) diluted 1:5,000 in TBST, is added and incubated for 1 hour at 4° C. Development is with standard o-phenylenediamine (OPD) chemistry (Pierce Chemical) with absorbance monitored at 490 nm. Blank wells with no proteins added serve as blanks for subtraction of machine background absorbance.

We observe robust acetylation reactions with nanomolar/nanogram amounts of the Rtt109-Vps75 enzyme/chaperone complex (e.g., 40 ng corresponds to 49.6 nM; FIG. 14C). Notably, the absorbance signal for reactions performed in the presence of acetyl-CoA greatly exceeds the background observed with no Ac-CoA (FIG. 14D; by over 100-fold in FIG. 14F). Similar results are observed with recombinant *Xenopus* histones and histones purified from chicken cells, indicating that N-terminal tail acetylations on natural histones do not affect the assay. Importantly, addition of dimethylsulfoxide (DMSO) does not inhibit the ability of Rtt109 to acetylate H3-K56 until the final concentration reaches 5% (FIG. 14E). Finally, we have calculated a preliminary Z-factor score in our 96-well assay, a statistical measure of assay quality. We compared reactions with all components (positive controls) and those that contain all proteins but lack acetyl-CoA (negative controls, FIG. 14F). We observed a Z-factor value of 0.75, well above the cutoff of 0.5.

In sum, H3-K56 acetylation by Rtt109 is robustly and sensitively detected in this assay in a DMSO-insensitive manner. Therefore, we adapted our protocol for high-throughput screens (HTS).

Z-Factor for Our Histone H3K56 Acetylation Assay in a 384-Well Format

Figure 17:
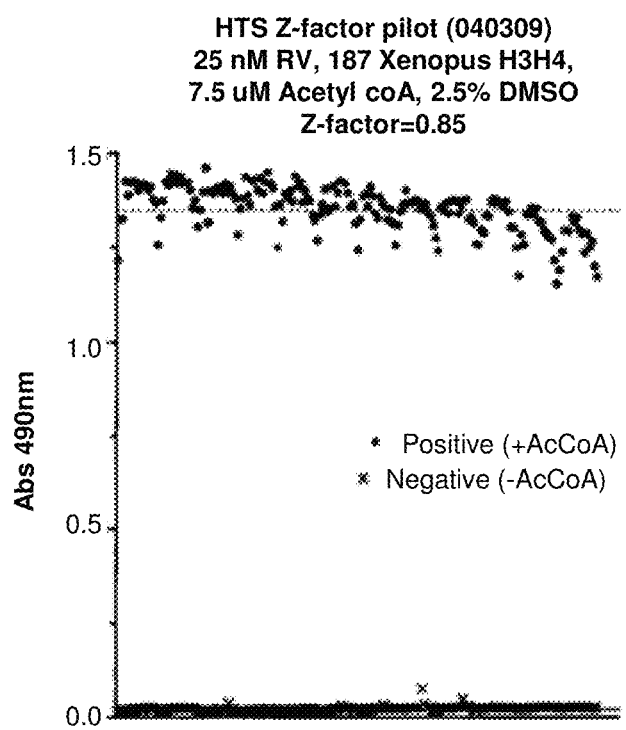
FIG. 17.
Figure 18:
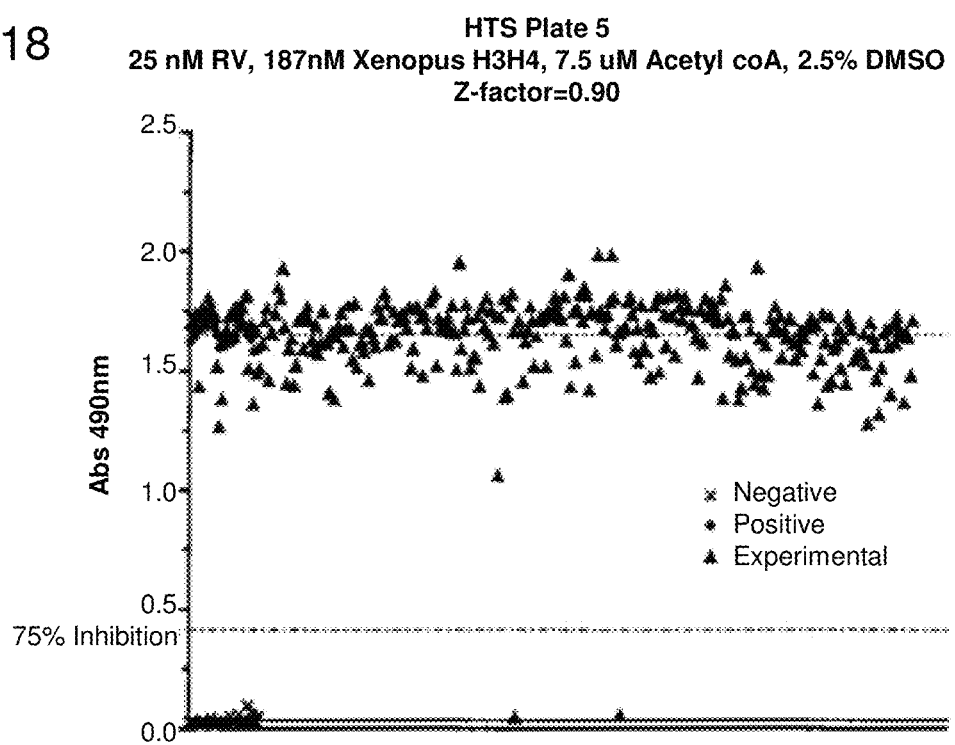
FIG. 18.

We performed 40 µl histone acetylation reactions containing 25 nM Rtt109-Vps75 enzyme complex, 187 nM histones H3/H4, 7.5 µM acetyl-CoA. We used these multiple turnover conditions to allow detection of inhibition at any stage in the catalytic cycle. The final DMSO concentration was 2.5%, which is well-tolerated by Rtt109. Histone acetylation was measured via an ELISA assay. We routinely observed Z-factors of 0.85-0.90 (FIGS. 17 and 18).

Screen of 30,000 Compounds

We have completed a pilot screen of 30,000 compounds at the UMass Small Molecule Facility. The compounds were added to a final concentration of 125 µM. Our preliminary data encouraged us to set a stringent cutoff of 75% inhibition for compounds to be considered primary candidates. We detected 160 compounds that caused ≥75% inhibition (0.52% initial hit rate; see FIG. 18 for an example). Notably, the majority of these compounds fell into 8 structural subclasses. Therefore, in consultation with the chemist at the UMASS Small Molecule facility, we reordered from ChemBridge 93 compounds for secondary testing, omitting some compounds that were extremely similar, as well as those unavailable for reorder.

Figure 19:
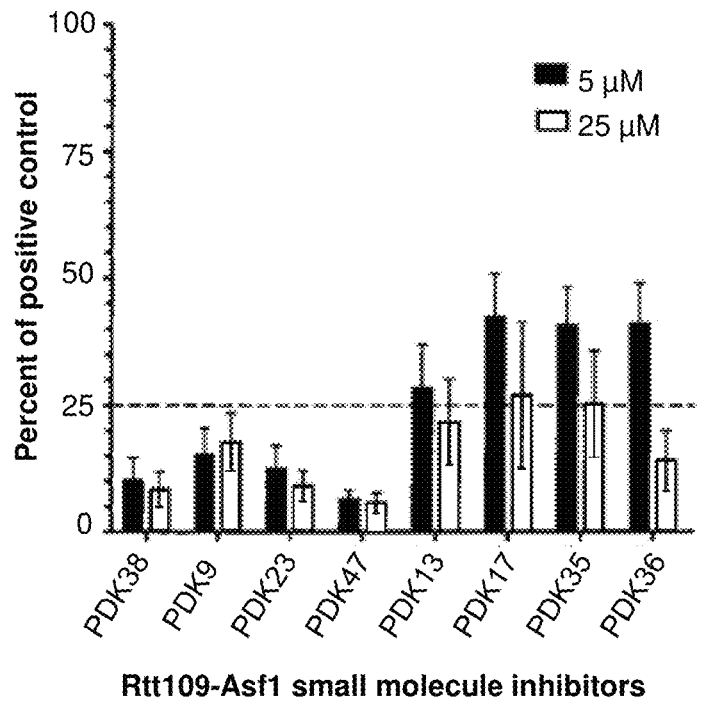
FIG. 19.

We retested all 93 reordered compounds under the initial assay conditions (compounds at 125 µM), and observed >75% inhibition by 37 compounds (0.12% corrected hit rate). These 37 compounds were then tested in manually-assembled assays in a 96-well format. Eight compounds inhibited the Rtt109-Vps75 enzyme at a final concentration of 25 µM, and four of these were still >75% inhibitory at 5 µM (FIG. 19).

Secondary Criteria

In addition to inhibition of the Rtt109-Vps75 complex, we have developed both positive and negative secondary tests. As a positive criterion, candidate compounds should also inhibit histone acetylation by Rtt109 stimulated by Asf1 instead of Vps75. As a negative criterion, compounds should not inhibit the distantly related human p300 enzyme.

Figure 20:
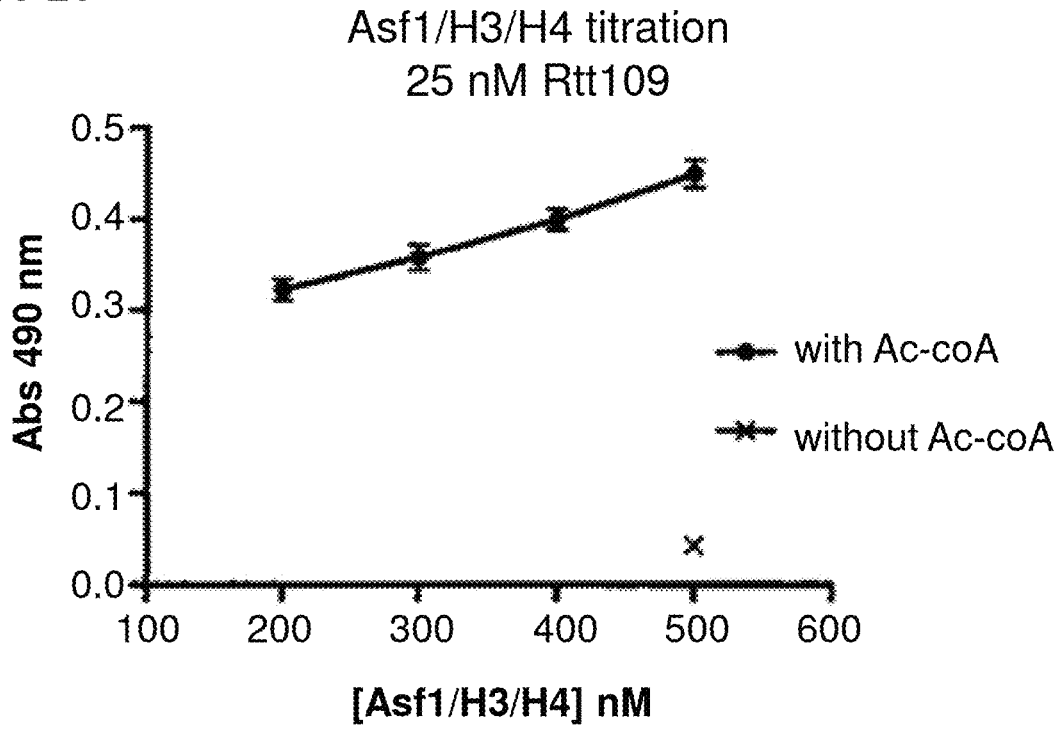
FIG. 20.

We have completed the positive tests. We first established conditions for the ELISA-based detection of histone acetylation by Rtt109+Asf1 (FIG. 20). Although the signal strength in these assays is not as strong as observed with the Rtt109/Vps75 complex (compare Y-axes of FIGS. 20 and 18), we found that 25 nM Rtt109 plus 300 nM of a preformed Asf1-H3/H4 complex provided suitable signal strength.

Figure 21:
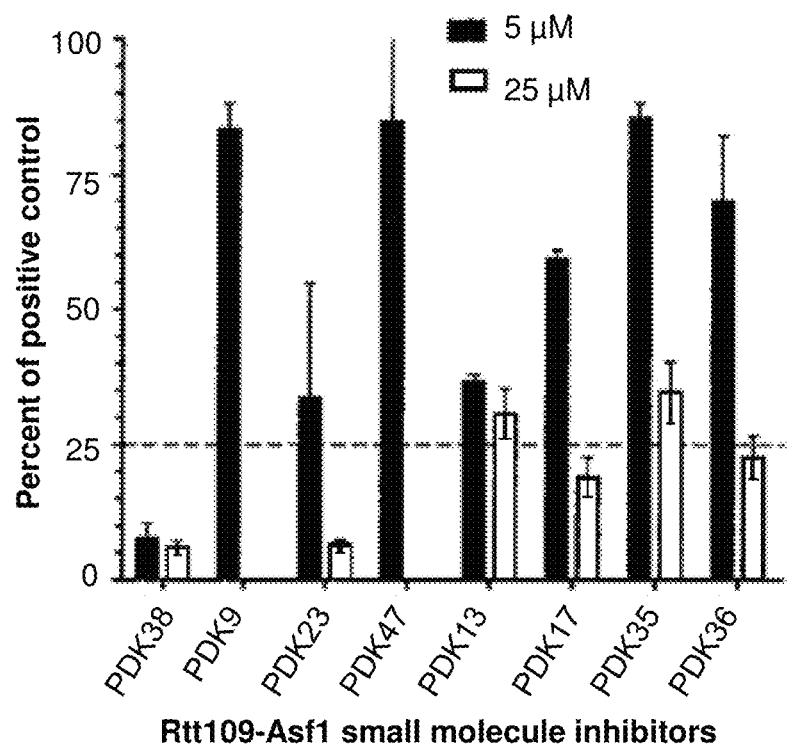
FIG. 21.
Figure 22:
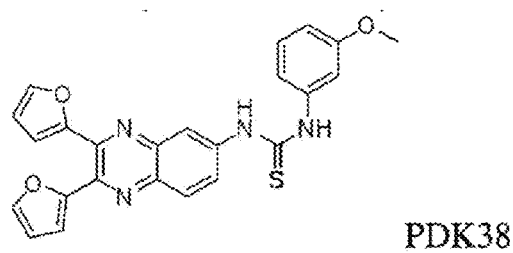
FIG. 22.
Figure 22:
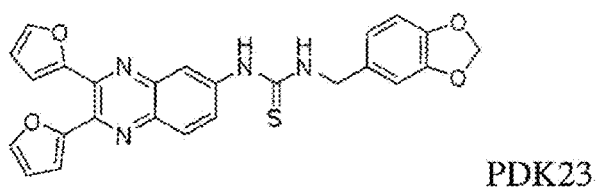
Figure 22:
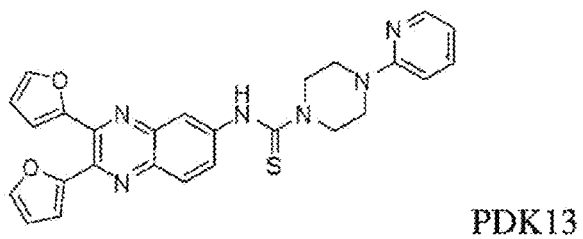

We have performed an initial set of reactions to test the eight best candidates under these conditions (FIG. 21). All eight compounds were more than or nearly 75% inhibitory at 25 µM. However, only one compound, termed PDK38, was highly inhibitory at 5 µM, with two others, PDK23 and PDK13, displaying some activity at this concentration in the Asf1-based assay. Notably, these three compounds display significant regions of similarity (FIG. 22). In preliminary assays, these compounds appear to be promiscuous protein inactivators.

Figure 23:
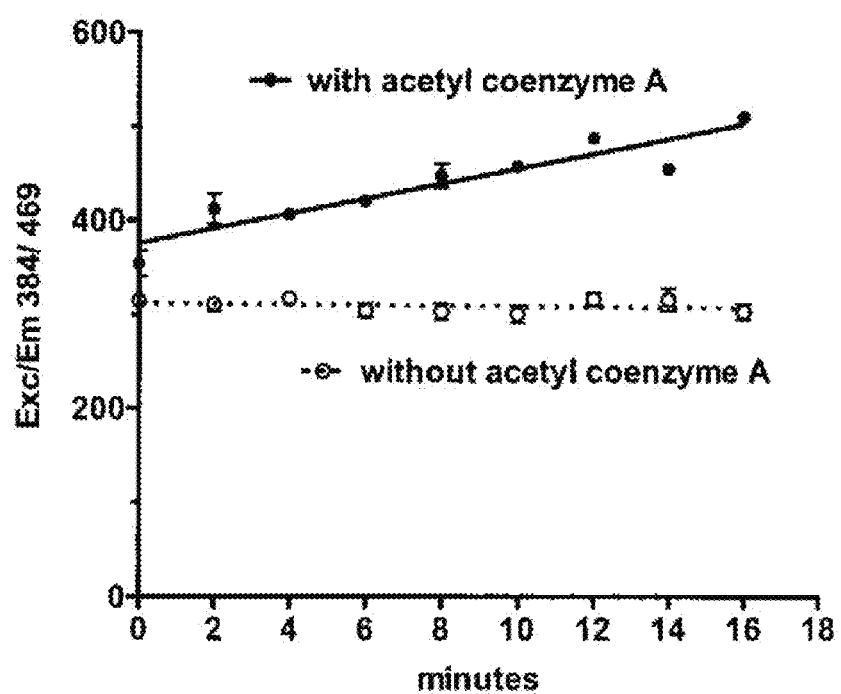
FIG. 23.

To perform the detailed kinetic analyses, assays that are more amenable to rapid time points than the ELISA assay are preferred. We have found that continuous, coupled systems that can monitor histone peptide acetylation (Berndsen et al., *Methods* 36: 321-331, (2005) are not useful using full-length H3/H4 tetramers because these inhibit the dehydrogenase enzyme required for NADH metabolism. In contrast, fluorescence-based detection of liberated CoA (Trievel et al., *Anal. Biochem.* 287:319-328, 2000) does work in our system, but the signal-to-noise ratio is not as high as our ELISA assay, unless very high substrate concentrations are used (FIG. 23). These data suggest that the ELISA assay could be suited for high-throughput screening.

Example 11

Identification of an Antifungal Compound that is a Specific Rtt109 Inhibitor

Here, we present the discovery of the first compound that specifically inhibits Rtt109 HAT activity, but not those of p300 or Gcn5. This compound inhibits Rtt109 in the presence of either Vps75 or Asf1, and inhibits HAT reactions using either N-terminal histone peptide or histone tetramer substrates.

Results

High-Throughput Screen for Rtt109 Inhibitors

The Rtt109-Vps75 complex displays a catalytic efficiency ($k_{cat}/K_m$) 20-fold greater than Rtt109/Asf1-mediated catalysis, and Rtt109 tightly binds to Vps75 ($K_d$=~10-23 nM; (Tsubota, 2007; Albaugh, 2010; Berndsen, 2008), allowing easy co-expression and purification from bacteria. Therefore, we developed a high throughput screen (HTS) for small molecule inhibitors of the HAT activity of recombinant Rtt109-Vps75 complexes, and planned to test for inhibition of Rtt109/Asf1 as a secondary criterion.

In the primary HTS, we used a fluorescent maleimide (ThioGlo1) for detection of the free sulfhydryl group on coenzyme A (CoA) molecules produced during the reaction ((Trievel, 2000), see Materials and Methods). We screened 363,843 small molecules in a 1536-well plate format at a compound concentration of 25 µM in single-point HAT assays. Each compound was assayed twice, and 224 out of 333,734 compounds that generated two data points yielded >50% inhibition (0.07% hit rate). For those compounds where only a single measurement was obtained, 313 out of 30,109 yielded >50% inhibition (1% hit rate).

Of these initial 539 hits, 449 compounds were readily available for re-testing in an 8-point, 2-fold dose titration. During these retests, the free sulfhydryl groups of released CoA were detected using Ellman's reagent (DTNB) via optical absorbance rather than via fluorescence using Thio-Glo1. This alternate detection strategy was designed to eliminate non-specific fluorescence quenchers obtained in the initial screen. In the retests, we observed that 83 compounds produced a dose-dependent response with an estimated IC50≤20 µM. Thirty-two of these compounds were chosen to retest as freshly ordered powders based on their medicinal chemistry potential. Again, these compounds were tested in 8-point 2-fold dose response curves. Nine of these compounds exhibited IC50 values below 10 µM. These nine compounds were then further characterized for their specificity.

A Specific Inhibitor of Rtt109

Figure 24:
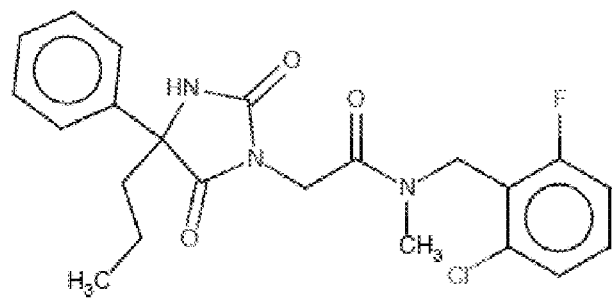
FIGS. 24A-24C. KB7 is a specific inhibitor of Rtt109 HAT catalysis.
Figure 24:
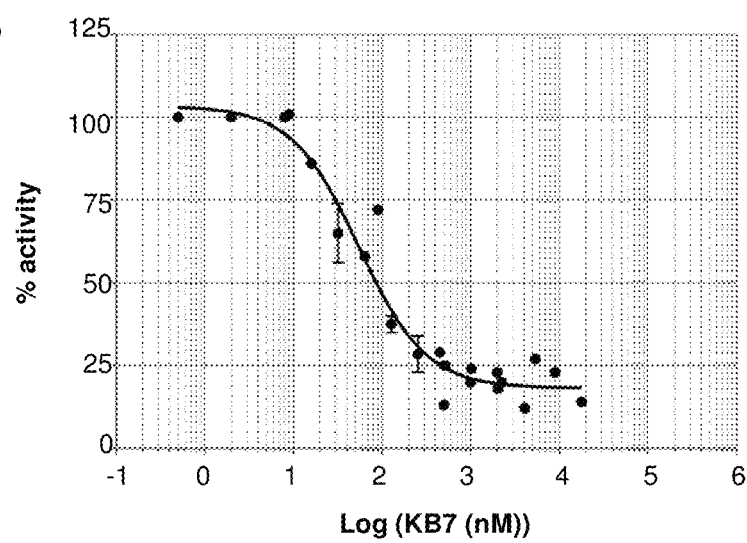
Figure 24:
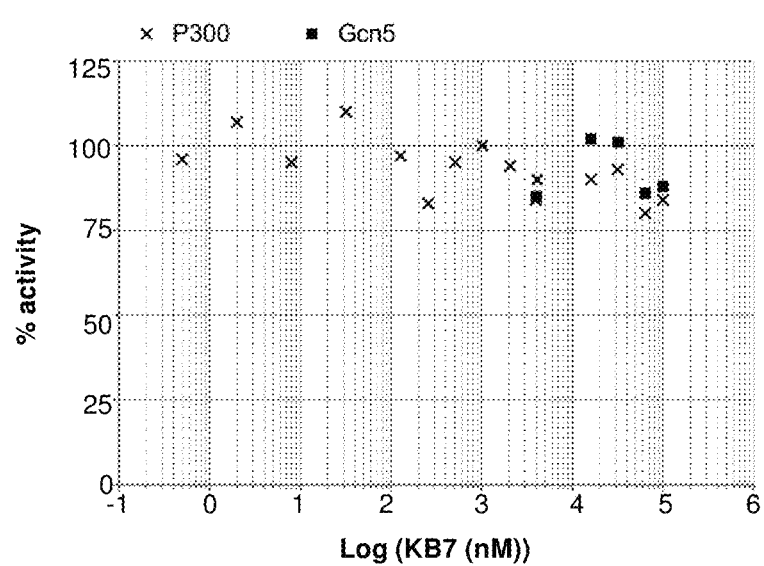

A critical criterion for our compounds was that they should inhibit Rtt109 but not the HAT activity of mammalian p300. We therefore performed single point enzyme assays comparing Rtt109-Vps75 and p300 in the presence of 0.5-2 µM of each of the nine remaining candidate compounds. Only a single compound, termed compound "KB7," inhibited Rtt109 without inhibiting p300 (FIG. 24A). Compound KB7 has the chemical formula $C_{22}H_{23}ClFN_3O_3$ (IUPAC name N-[(2-chloro-6-fluorophenyl)methyl]-2-(2,5-dioxo-4-phenyl-4-propylimidazolidin-1-yl)-N-methylacetamide), and is listed as PubChem Compound CID 4785700, Substance SID 49676148. Notably, current listings for PubChem Bioactivity assays show it has been tested in 368 assays, but was active in only two. One was our screen (PubChem BioAssay AID 588764), and the other assay was for small molecule inhibitors of the interaction between the tudor domain of histone methyltransferase JMJD2A an histone H4 peptide trimethylated on lysine 20 (PubChem BioAssay AID 504339). However, in the latter case, the IC50 value was reported to be 25 mM. Therefore, the present results are the most potent effects reported for this compound to date.

To assess IC50 values for Rtt109-Vps75 inhibition, we performed HAT reactions with varying concentrations of Compound KB7 and determined rates during the initial linear phase of the reaction. Each reaction rate was calculated via linear regression of product formed versus time (mean $R^2$=0.91, ranging from 0.77-0.99). Reaction velocities were plotted against Compound KB7 concentration on a semi-log scale (FIG. 24B), revealing a dose response over approximately two orders of magnitude, from 10 nM-1 mM. For inhibition of Rtt109-Vps75, a non-linear fit of the data (GraphPad Prism) indicates an IC50+/−SEM of 56+/−1.3 nM and Hill slope coefficient of −1.09+/−0.28 SEM ($R^2$=0.9397) (FIG. 24B). We conclude that Compound KB7 is a potent inhibitor of Rtt109-Vps75. However, Compound KB7 does not appear to have a cooperative effect on the enzyme, because the Hill coefficient is not statistically distinguishable from −1.

In contrast to Compound KB7's potent effects on Rtt109-Vps75, it did not significantly inhibit the HAT activity of either p300 or Gcn5. As above, each reaction rate was determined via linear regression of product formed versus time (for p300, mean $R^2$=0.98, ranging from 0.97-0.99; for Gcn5 mean $R^2$=0.97, ranging from 0.94-0.99). High concentrations of Compound KB7 (up to 100 µM) did not reduce enzyme reaction rates below 80% activity, with no apparent trend as KB7 concentration was increased (FIG. 24C). Due to solubility limitations, Compound KB7 was not tested above 100 µM. We conclude that Compound KB7 has a greater than two order of magnitude preference for inhibition of Rtt109.

Compound KB7 Inhibits H3K56 Acetylation on (H3-H4)$_2$ Tetramers when Rtt109 is Stimulated by Either Vps75 or Asf1

Figure 25A:
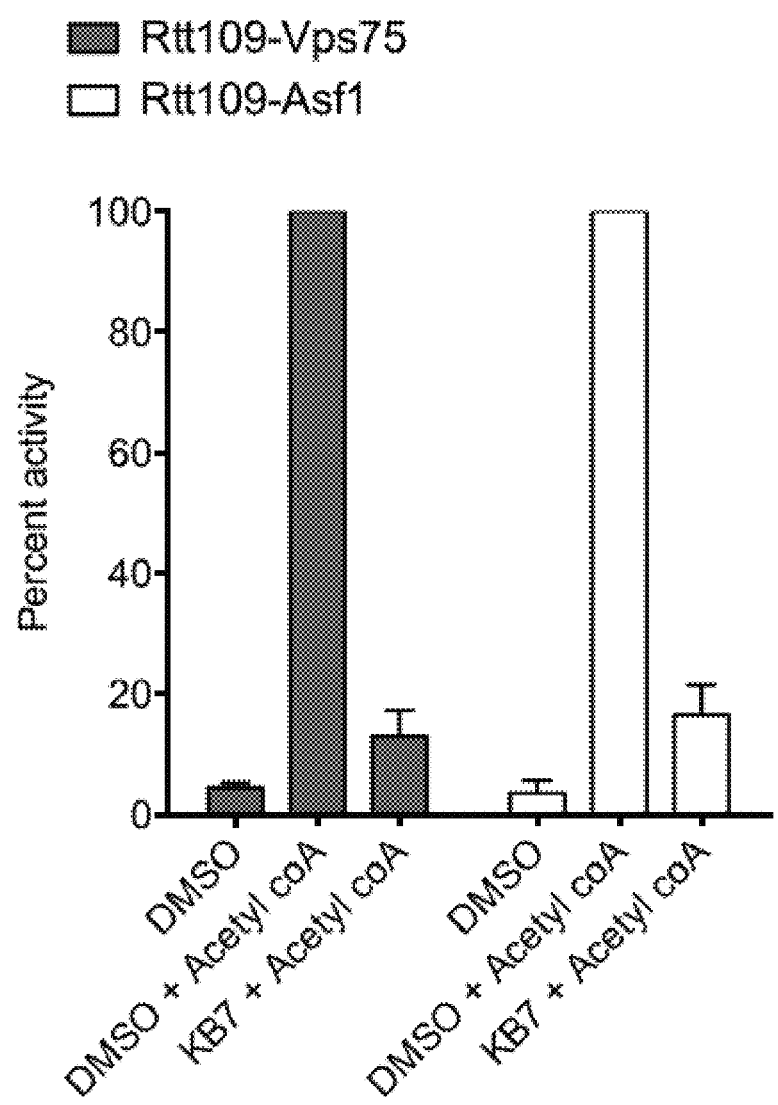
FIGS. 25A and 25B. KB7 specifically inhibits H3K56 acetylation by both Rtt109-Vps75 and Rtt109-Asf1 complexes.
Figure 25B:
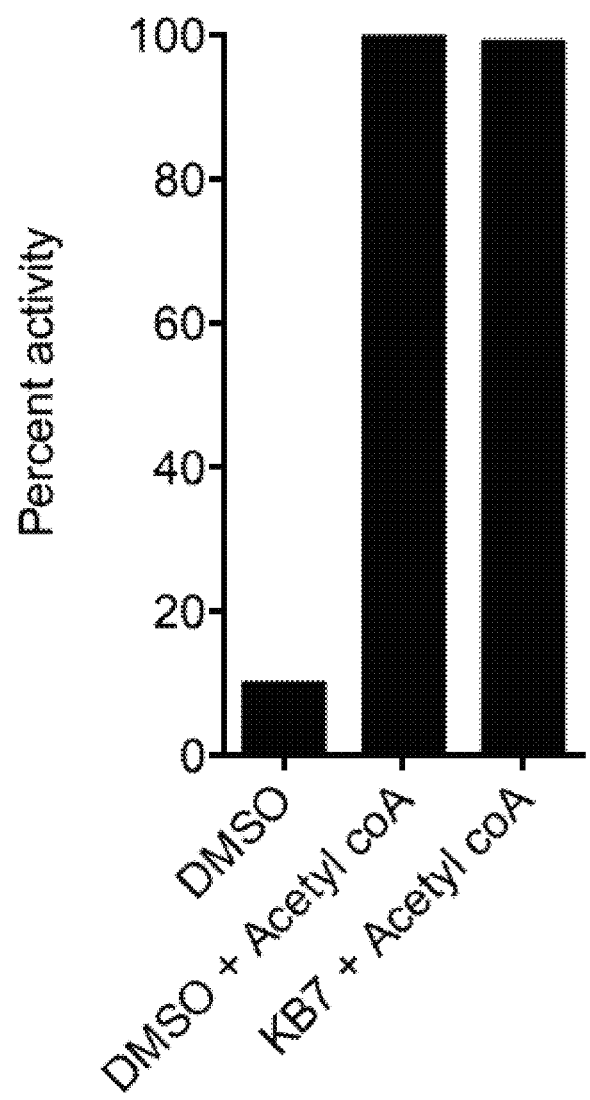

Point mutation data from structural studies suggested that some Rtt109 amino acids important for catalysis by Rtt109-Vps75 complexes are not required for acetylation by Rtt109/Asf1 (Tang, 2011). Therefore, it was conceivable that an Rtt109 inhibitor could affect catalysis stimulated by either Vps75 or Asf1, but not necessarily both. To compare inhibition of acetylation by Rtt109-Vps and Rtt109/Asf1, we performed single-point HAT assays using (H3-H4)$_2$ tetramers as the substrates, detecting H3K56ac by ELISA using a modification-specific anti-H3K56ac antibody. Histone tetramer substrates rather than H3 N-terminal peptides were required for these experiments because Asf1 stimulates H3K56 acetylation but not N-terminal acetylation (Berndsen, 2008; Fillingham, 2008). In these assays, we observed that Compound KB7 inhibited acetylation by both Rtt109-Vps75 and Rtt109/Asf1 comparably (FIG. 25A). Importantly, these data also confirm that acetylation of H3K56 is inhibited by Compound KB7, which had not been examined in the ThioGlo1-based assays that used the N-terminal histone H3n21 peptide substrate. Additionally, we also tested whether Compound KB7 would affect p300 HAT activity on (H3-H4)$_2$ tetramers, using the same HAT-ELISA methodology with antibodies that detect acetylation of H4 N-terminal residues. Consistent with the previous data, we observed that Compound KB7 had no inhibitory effect on p300 (FIG. 25B). We conclude that Compound KB7 is a specific inhibitor of Rtt109 but not p300, and can inhibit Rtt109 activity regardless of cofactor protein or substrate lysine.

Discussion

Through a high-throughput screen we have identified a specific Rtt109 inhibitor, termed Compound KB7. Compound KB7 inhibits Rtt109 with an apparent IC50 of ~56 nM and but does not significantly inhibit the other HATs tested, p300 and Gcn5, even at concentrations up to 100 uM, suggesting that there is at least two orders of magnitude of specificity for Rtt109. Importantly, KB7 inhibits H3K56 acetylation by Rtt109 activated by either Vps75 or Asf1. H3K56ac is the physiologically relevant PTM for genome stability and efficient pathogenicity of yeast in the face of DNA damage. Because structural and mutational studies suggest that Vps75 and Asf1 interact with distinct regions of Rtt109 (Tang, 2011), these data suggest that KB7 does not simply block interaction between Rtt109 and the histone chaperones, but in fact prevents catalysis. Furthermore, the ability of KB7 to inhibit R-V mediated catalysis on H3n21 peptides, representing the N-terminal tail residue H3K9, and H3K56 on full-length histone H3 indicates that it inhibits catalysis on multiple substrate lysine.

In our case, KB7 is efficient at nanomolar range, equivalent to Rtt109 concentration, when the substrates are at micromolar range. It is unlikely that sequestration of substrates is occurring.

The inhibition mechanism of KB7 is complex. KB7 decreases the Vmax with respect to both Ac-CoA and H3n21 substrates, indicating that the substrates do not compete with the inhibitor to prevent inhibition (FIGS. 3.3 and 3.4). The inhibitor is therefore noncompetitive with respect to both substrates and most likely binds allosterically on Rtt109 to prevent catalysis without affecting either substrate (or chaperone) interaction.

Thus, KB7 exhibits properties consistent with its use as an antifungal agent.

Materials and Methods

Protein Expression and Purification

Recombinant *S. cerevisiae* 6×His-Rtt109, 6×His-Vps75 and co-expressed Rtt109-Vps75 complexes with a 6×His tag on either protein were purified as previously described (Tsubota, 2007). Recombinant *S. cerevisiae* FLAG-epitope-tagged Asf1N(N-terminal amino acids 1-155) was purified as previously described (Daganzo, 2003). Recombinant *Xenopus laevis* histone H3 and histone (H3-H4)$_2$ tetramers were purified as previously described (Luger, 1999). All proteins were dialyzed into 20 mM Hepes-NaOH, pH 7.5, 25 mM NaCl, 1 mM EDTA, 5% glycerol, ultracentrifuged at 100,000×g for 45 minutes and stored in small aliquots at −80° C.

Recombinant 6×His-FLAG-p300 catalytic domain (p300 amino acids 1195-1810; Fan, 2010) was expressed in BL21 *E. coli* cells and purified on Ni-NTA resin (Qiagen) using the manufacturer's instructions. The peak elutions were pooled and dialyzed in 20 mM Hepes, 7.5, 25 mM NaCl, 1 mM EDTA, 5% glycerol and 1 mM PMSF (phenylmethylsulfonyl fluoride) and stored in small aliquots at −80° C.

BL21 *E. coli* cells transformed with a construct encoding recombinant *S. cerevisiae* 6×His-Gcn5 (CP921) were cultured at 37° C. and diluted back to O.D.$_{600\ nm}$=0.01 in 4×1 L at 18° C. overnight. Cells were induced with 0.2 M IPTG between O.D.$_{600\ nm}$=0.38-0.5 for 4 hours at 28° C. Four cell pellets were collected and washed with 25 mL 50 mM NaPO$_4$ pH 7.0, 100 mM NaCl, 1 mM benzamidine, 5 mM beta-mercaptoethanol. Gcn5 was precipitated with 70% NH$_4$SO$_4$ by slowly adding finely ground NH$_4$SO$_4$ crystals at 4° C. while stirring. The solution was centrifuged at 20,000×g and the pellet was resuspended in 20 mM Hepes pH 7.5, 1 mM EDTA, 10% glycerol, 0.01% NP40. Gcn5 was dialyzed into 20 mM Hepes, 7.5, 1 mM EDTA, 5% glycerol (no salt), ultracentrifuged at 100,000×g for 45 minutes and stored in small aliquots at −80° C.

High Throughput Screen

Primary Screen:

Using a BioRaptr robot (Beckman), 80 nM Rtt109-Vps75 (or just reaction buffer) and 50 µM screening compound were joined in 1 µl. Reactions were initiated with the addition of 1 µl 120 µM H3n21 peptide (21$^{st}$ Century Biochemicals, Marlboro, Mass. Cat# H3 1-21NT), 150 µM Ac-CoA in reaction buffer. The final composition of the HAT reaction is 40 nM Rtt09-Vps75, 60 µM H3n21 peptide, 75 µM Ac-CoA and 25 µM screening compound in 50 mM Hepes, 0.0005% Pluronic F-68, pH8.0. The reaction proceeded for 4 hours at RT in a humid chamber. Released coenzyme A was detected by the addition of 0.5 µl 370 µM ThioGlo1 in PBS, 0.0005% Pluronic pH 7.4, for a final volume of 2.5 µl at 74 µM. After 10 minutes at RT, plates were read at ex380/em510 on an Envision (Perkin Elmer) plate reader. Each compound was tested twice. Hits were determined as causing >50% inhibition in duplicate. For data points were only a single reading was available, hits were also determined if >50% inhibition was observed.

Cherry Picks

From the HTS, 537 hits were cherry picked for retesting. Only 449 compounds were available. These compounds were tested 2-3 times in 8-point, 2-fold dose titrations ranging from 20-0.156 µM in 384-well clear-bottom black plates. The reactions were prepared by adding 0.1 µl compound to 25 µl 200 nM Rtt109-Vps75 (or just reaction buffer). The enzyme complex and compound were incubated at RT for 10 minutes. Reactions were initiated with the addition of 25 µl 120 µM H3n21 peptide, 150 µM Ac-CoA in reaction buffer. The final composition of the HAT reaction was 100 nM Rtt09-Vps75, 60 µM H3n21 peptide and 75 µM Ac-CoA in 50 mM Hepes 0.0005% Pluronic F-68, pH 8.0. The reaction proceeded for 2 hours at RT°. Released coenzyme A was detected by the addition of 10 µl 4 mM Ellman's Reagent (DTNB) in PBS, 0.0005% Pluronic pH 7.4, for a final volume of 60 µl at 0.66 µM. After 10 minutes at RT°, plates were read at absorbance 405 nm on an Envision (Perkin Elmer) plate reader.

Powders:

Thirty-two compounds were chosen from the cherry pick data to retest as freshly ordered powders. Twenty-eight of these were chosen based on yielding an IC50≤20 µM and having medicinal chemistry potential. Four additional compounds were chosen based on chemical expertise. The powder retest was performed similarly to the cherry picks done in duplicate 8-point dose responses. The criterion for powder re-test was IC50<10 µM.

HAT-ELISA Assay

Single-point enzyme assays analyzed by ELISA were performed with 50 nM Rtt109 and 50 nM Vps75 or 400 nM Asf1-N terminus (amino acids 1-155) or 15 µg/mL p300. 300 nM (H3-H4)$_2$ tetramer substrate was provided. Reactions were initiated with 30 µM Ac-CoA (Sigma Aldrich, catalogue #A2056). Briefly, the protein mix was assembled on ice in 50 mM Tris, pH 8.0, 0.1 mg/ml BSA, 1 mM DTT to a volume of 323.4 µl. 3.3 µL of Dimethylsulfonate (DMSO) or a 100× stock of inhibitor was added, generating a final concentration of 1% DMSO in the reactions. The reaction was placed at 30° C. for 5 minutes to allow temperature equilibration before initiating with 3.3 µL of 100× (=3 mM) Ac-CoA. After 30 minutes, the reactions were stopped by placing on ice, and 100 µL were plated in triplicate on Immulon B 96-well ELISA plates. The plates were stored overnight at 4° C. to allow proteins to bind to the plastic.

Reactions were decanted and non-specific binding by the antibodies was prevented by incubating the wells with 200 µL 1% BSA, 0.05% Tween-20, TBS for 1-2 hrs at 4° C. ELISA detection was performed with 100 µL per well of rabbit anti-serum raised against an H3K56ac peptide (21$^{st}$ Century Biochemicals, Marlboro, Mass.) diluted at 1:5000 in ELISA buffer (0.05% tween-20, TBS) for 1-2 hrs at 4° C. Anti-rabbit HRP-conjugated IgG was used at 1:2500 in ELISA buffer for 100 µL per well for 1 hr at 4° C. Washes before and after antibody incubations were performed 3×200 µL per well with ELISA buffer.

HAT-ThioGlo1 Time Course Assay

Kinetic measurements of HAT reactions were performed using 50 nM co-expressed Rtt109-Vps75, 15 µM Histone H3 N-terminal peptide residues 1-21 (H3n21) and 30 µM Ac-CoA (Sigma Aldrich), unless otherwise indicated. In reactions with other HATs, 15 µg/mL p300 or 3.07 µg/mL Gcn5 was used. Reactions were assembled on ice in 20 mM Hepes-NaOH, pH 7.5, 0.01% NEM-treated BSA (Trievel, 2000), 0.01% Triton X-100 to a volume of 646.8 µL in glass tubes. 6.6 µL of Dimethylsulfonate (DMSO) or 100× inhibitor was added for a final concentration of 1% DMSO. Unless otherwise indicated, the reaction was place at 30° C. for 5 minutes to allow temperature equilibration before initiating with 3.3 µL of 100× (=3 mM) Ac-CoA. 120 µL samples were collected at 2, 4, 6, 8 and 10 minutes after initiation, directly added to 120 µL ice cold isopropanol and vortexed. Stopped reaction time-points were stored at −20° C. until further use.

The amount of coenzyme A released upon acetylation was quantified at each collected time point as previously described (Trievel, 2000), and results were analyzed using Prism GraphPad software. Briefly, released coenzyme A is detected by a maleimide reagent (ThioGlo1; EMD, catalogue #595501) which fluoresces upon binding to the free sulfhydryl exposed on Coenzyme A. Rates were determined by comparison with standard curves of fluorescence obtained with known amounts of Coenzyme A (CoA; Sigma Aldrich, catalogue #C3144). Two-fold serial dilutions from 6-0.5 µM CoA were prepared in HAT reaction buffer for each plate, and an equal volume of isopropanol was added. To measure fluorescence, 100 µL per well of the stopped reactions or standards (in duplicate or triplicate, respectively) were plated in FluoTrac200 medium-binding black plates (Greiner, VWR, catalogue #655076). 100 µL of 30 µM ThiolGlo1 diluted in 1% Triton X-100 was added and mixed by pipetting. The plate was incubated at RT for 30 minutes in the dark and read at ex384/em513.

In the substrate titration experiments, reaction rates versus substrate concentration were fitted to a non-linear regression curve and analyzed using the Michaelis-Menten equation by Prism GraphPad. Three concentrations of inhibitor were tested per experiment for each substrate, including a 1% DMSO control (no inhibitor). Eight concentrations of substrate were tested per concentration of inhibitor. Due to day-to-day variation in reaction rates, a single representative experiment is shown for each substrate titration. The trends and conclusions between the individual experiments are consistent.

Example 12

Compound #4 Inhibits Hyphal Formation in *Aspergillus*

Figure 26:
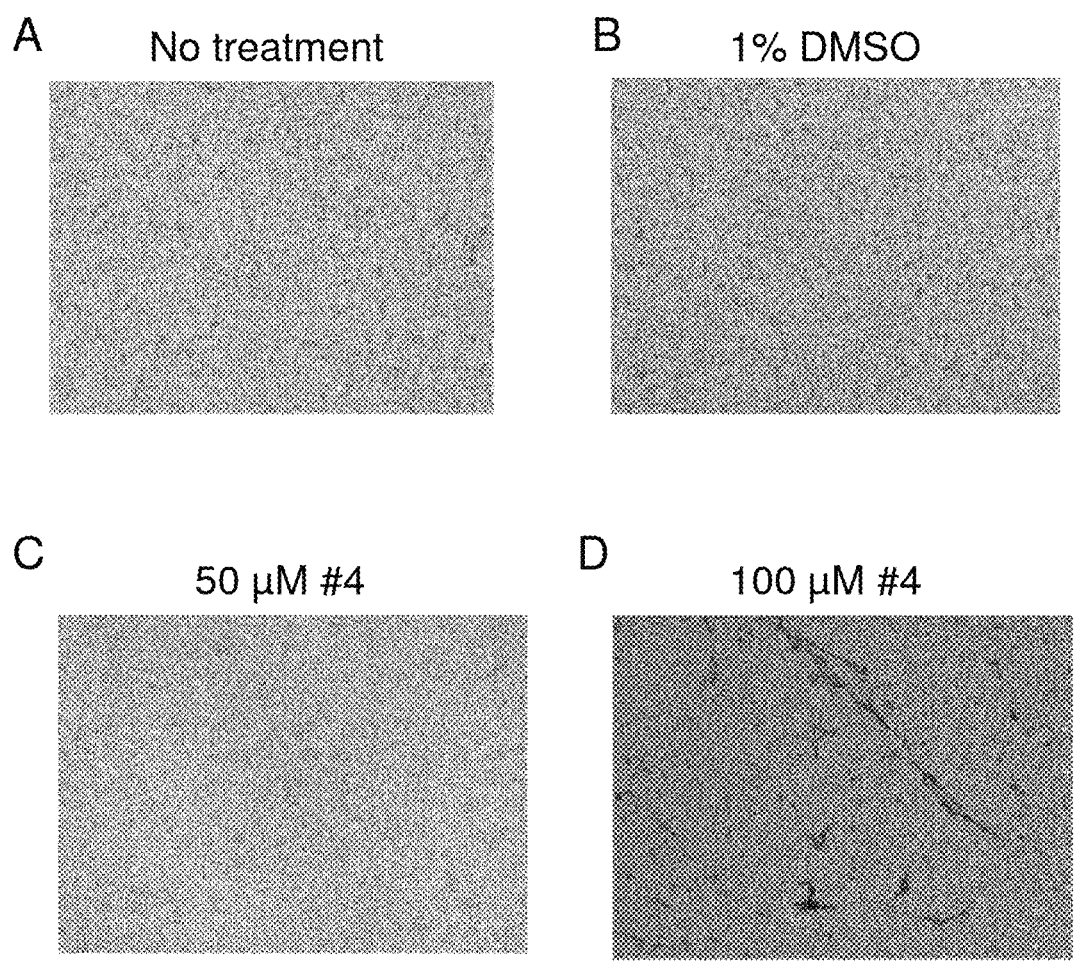
FIGS. 26A-26D. Compound #4 inhibits hyphal formation of *Aspergillus fumigatus*.

Compound #4 was also tested for its inhibitory effect on the growth of *Aspergillus fumigatus*. Fresh *Aspergillus fumigatus* conidia (spores) were grown in RPMI tissue culture media overnight in the presence of 1% DMSO (control), 50 µM compound #4, 100 µM compound #4, or no treatment (control) using methods similar to those described in Ramirez-Ortiz et al. (*Cell Host & Microbe* 9:415-424, 2011). As shown in FIG. 26, the conidia display the normal amount of hyphal elongation protruding from the cells in the untreated (FIG. 26A) and DMSO-treated (FIG. 26B) controls. This is the first step in germination of the spores, and is required for pathogenesis. As shown in FIGS. 26C and 26D, compound #4 blocks hyphal formation at both concentrations tested.

These data show: 1. That compound #4 exhibits anti-fungal activity that is desirable for fighting *Aspergillus* infections, and 2. That the similar inhibition of hyphal formation by compound #4 in *Aspergillus fumigatus* and *Candida albicans* (see above), organisms separated by 400 million years of evolution, suggests that compound #4 may have broad activity against many fungal species.

Example 13

Compound #4 Inhibits Hyphal Formation in *Cryptococcus*

Compound #4 was also tested for its inhibitory effect on the growth of *Cryptococcus* gatti. *Cryptococcus* cells were incubated at 37° C. in unsupplemented RPMI tissue culture media (+Glutamine–Phenol Red (Gibco #11835, Life Technologies, Grand Island, N.Y.; "RPMI") or RPMI tissue culture media supplemented with 100 U/ml Penicillin/100 ug/ml Streptomycin (Gibco 100× Pen/Strep #151500-122), 1 mM NaPyruvate, and 10 mM HEPES pH 7.0 ("Af medium") in the presence of 1% DMSO (control), 50 µM compound #4, or 100 µM compound #4, and cell numbers were counted after 18 hours. The assay was also performed with an untreated control.

Figure 27:
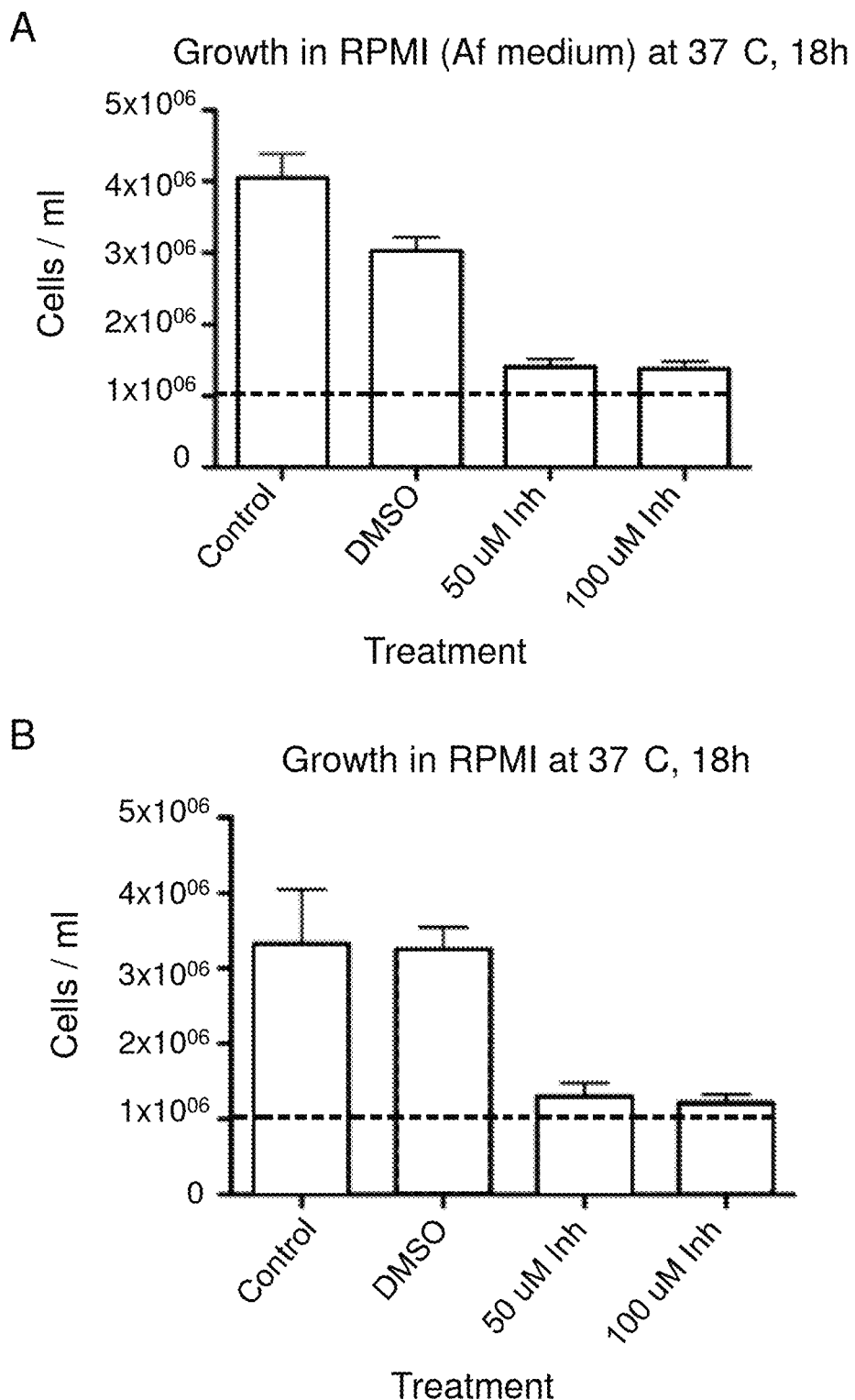
FIGS. 27A and 27B. Compound #4 inhibits proliferation of *Cryptococcus gatti*.

As shown in FIGS. 27A and 27B, compound #4 inhibited proliferation of *Cryptococcus* gatti at both concentrations tested. No difference in the results was observed using supplemented or unsupplemented RPMI.

These data show that compound #4 exhibits anti-fungal activity that is desirable for fighting this type of infection, and shows that this compound may be widely useful against many distantly related fungal species.

Example 14

Compound #4 Inhibits *C. albicans* Biofilm Formation and Inhibits Hyphal Morphogenesis and Normal Colony Morphology In the presence of DMSO vehicle, we confirmed that wildtype *C. albicans* cells efficiently formed biofilms on silicone mesh; in contrast, edt1−/− mutant cells did not, resulting in the majority of the cells dispersed throughout the media rather than adhered to the mesh (FIG. 5A). Measurements of the media turbidity and the biofilm dry weight measurements confirmed these assessments (FIG. 5B). Therefore, compound #4 has multiple activities, including the ability to inhibit adhesion of *C. albicans* to human cells.

Visual inspection of cells remaining at the end of adhesion assays suggested that some of the candidate compounds inhibit generation of hyphae. Because the ability to interconvert between yeast and hyphal morphologies is usually correlated with pathogenicity, we explored this in more detail, examining induction of hyphae upon carbon starvation (using Spider media). We used a strain that contains the Red Fluorescent Protein (RFP) open reading frame driven by the hyphal-specific HWP1 promoter (Ganguly et al., *Eukaryotic Cell* 10:1448, 2011), which provides a molecular reporter for hyphae formation in addition to cell morphology. We observed that compound #4, as well as a subset of the other compounds (e.g., compound #s 14, 26, 27, Q1, and Q2) blocked formation of hyphae. Our data also indicate that the related compound pairs (#4/#27 and Q1/Q2), were effective inhibitors of both hyphal morphogenesis and biofilm formation on silicone mesh (FIGS. 4A-C, 5A, and 5B). Therefore, the shared backbone of these compounds correlates with inhibition of multiple activities.

Figure 8:
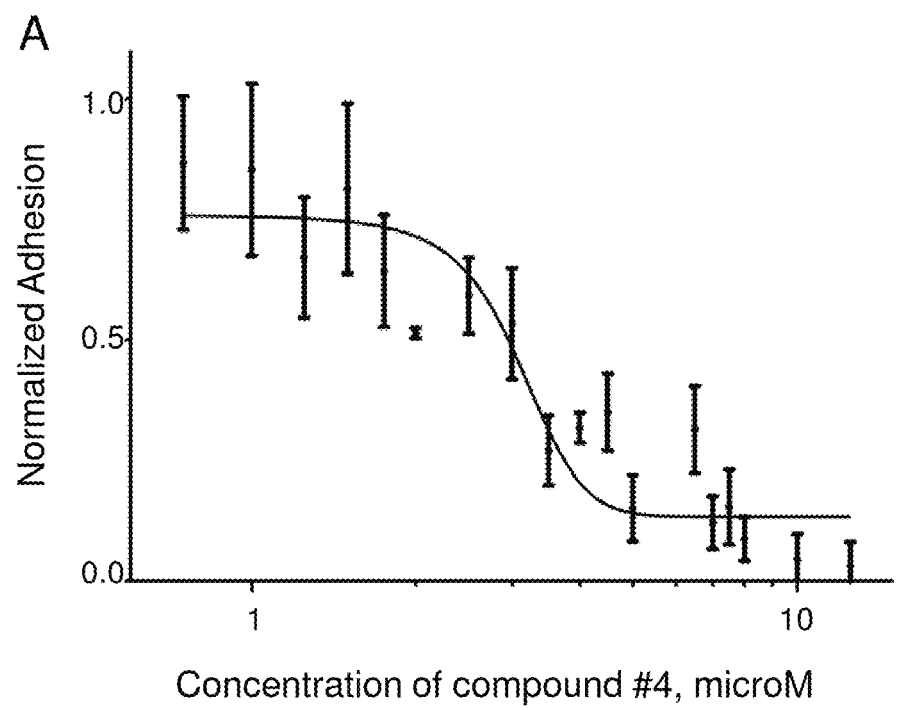
FIGS. 8A-8B. Characterization of compound #4.
Figure 8:
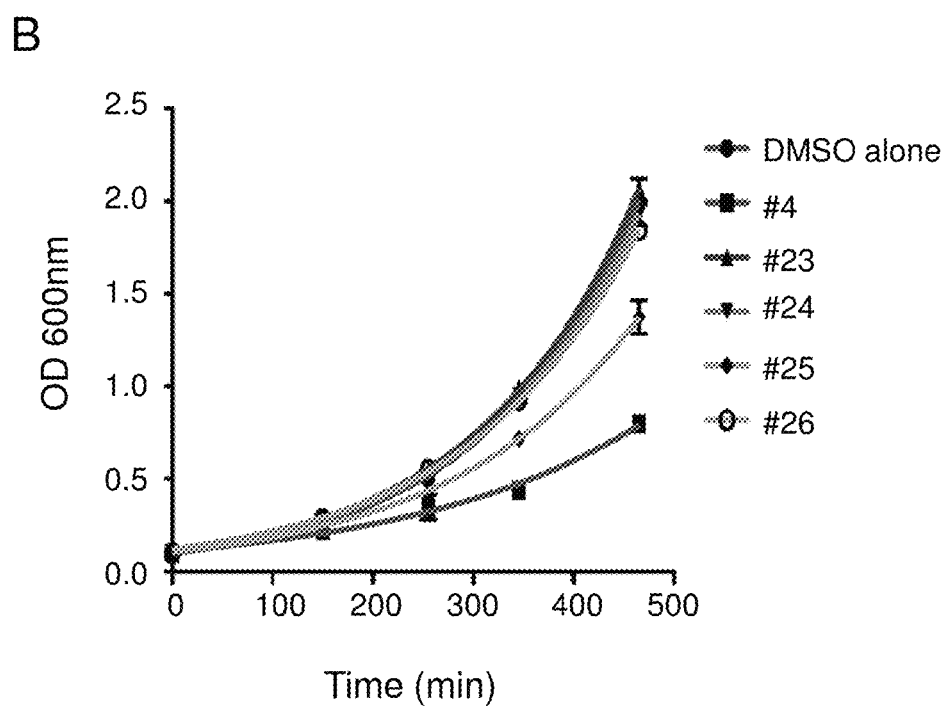
Figure 28:
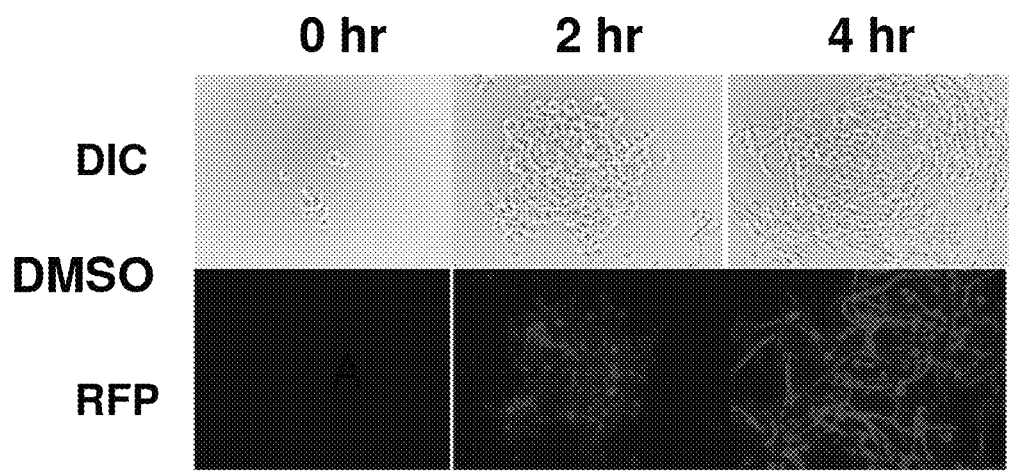
FIGS. 28A and 28B. Chemical modulation of *Candida albicans* morphogenesis.
Figure 28:
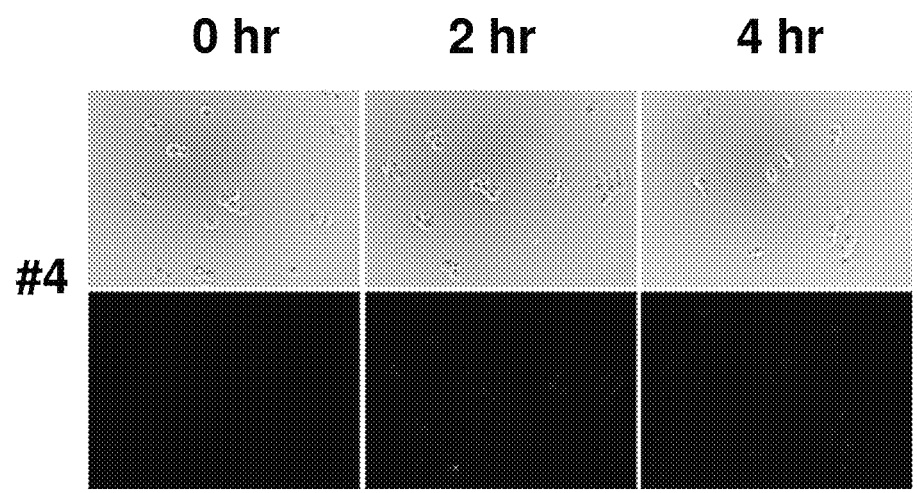

Upon titration, we observed that compound #4 is effective at inhibiting hyphae formation at concentrations >2.5 µM (FIG. 4A), similar to the results observed in the polystyrene adhesion assay (FIGS. 7 and 8). Using this protein reporter assay, the effect of the compound #4 could be detected within two hours of Spider media addition (FIGS. 28A and 28B).

Figure 29:
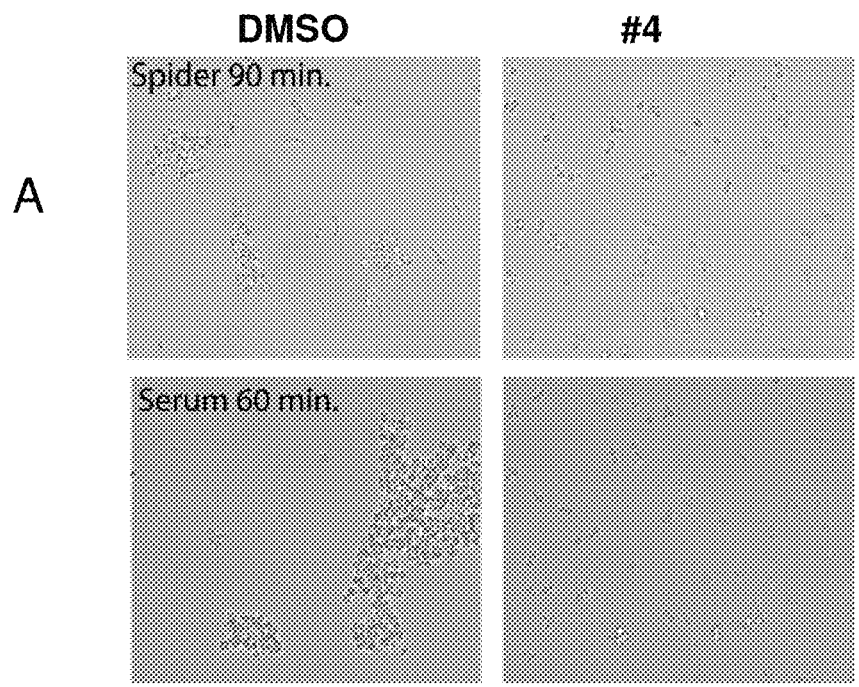
FIGS. 29A and 29B. Hyphal morphogenesis in response to serum and Spider media and colony morphology.
Figure 29:
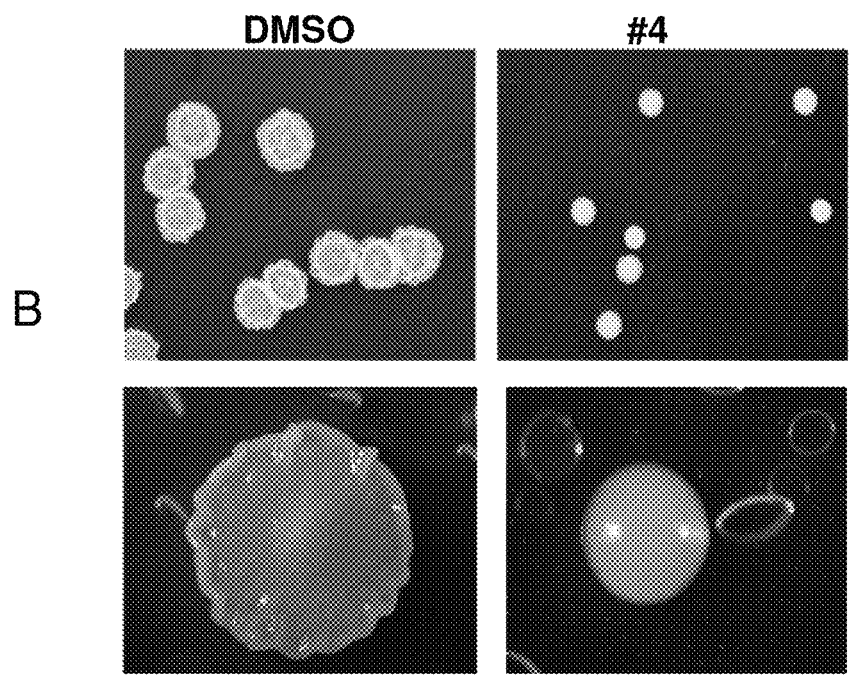

Hyphal morphogenesis is induced by multiple stimuli that act via multiple signal transduction pathways and is mediated by a complex transcriptional network. In addition to nutrient-poor Spider media, mammalian serum also induces hyphae, and we observed that compound #4 inhibited the response to both these stimuli (FIGS. 29A and 29B). We detected morphological difference between control and compound #4-treated cultures as early as 60 minutes in 10% serum, and 90 minutes in Spider media. Additionally, a wrinkled colony morphology is displayed by *C. albicans* when grown on solid Spider media, reflecting transitions between hyphal and yeast forms. Notably, this wrinkled phenotype was also abolished by compound #4 (FIGS. 29A and 29B). Together, our data indicate that compound #4 inhibits hyphal morphogenesis and a colony morphology phenotype that depends on the hyphal transition.

Figure 30:
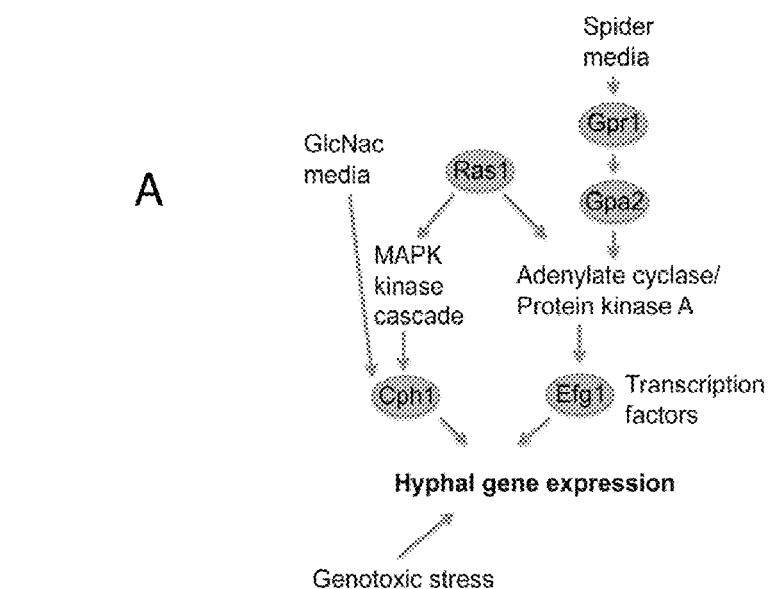
FIGS. 30A-30E. Compound #4 inhibits hyphal development induced by multiple signals.
Figure 30:
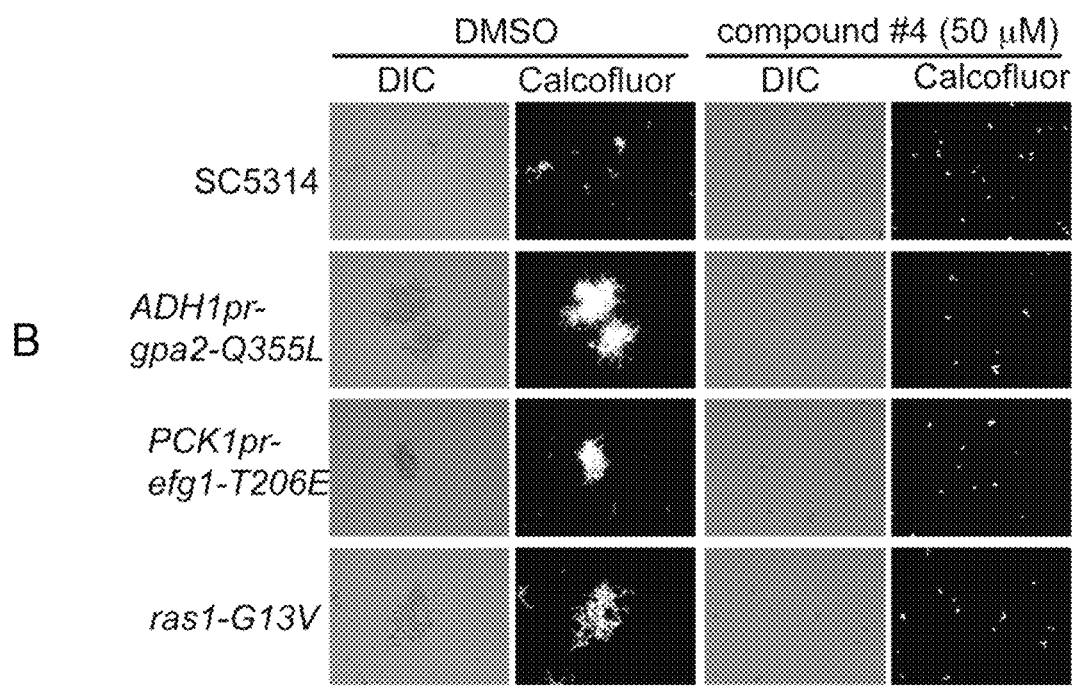
Figure 30:
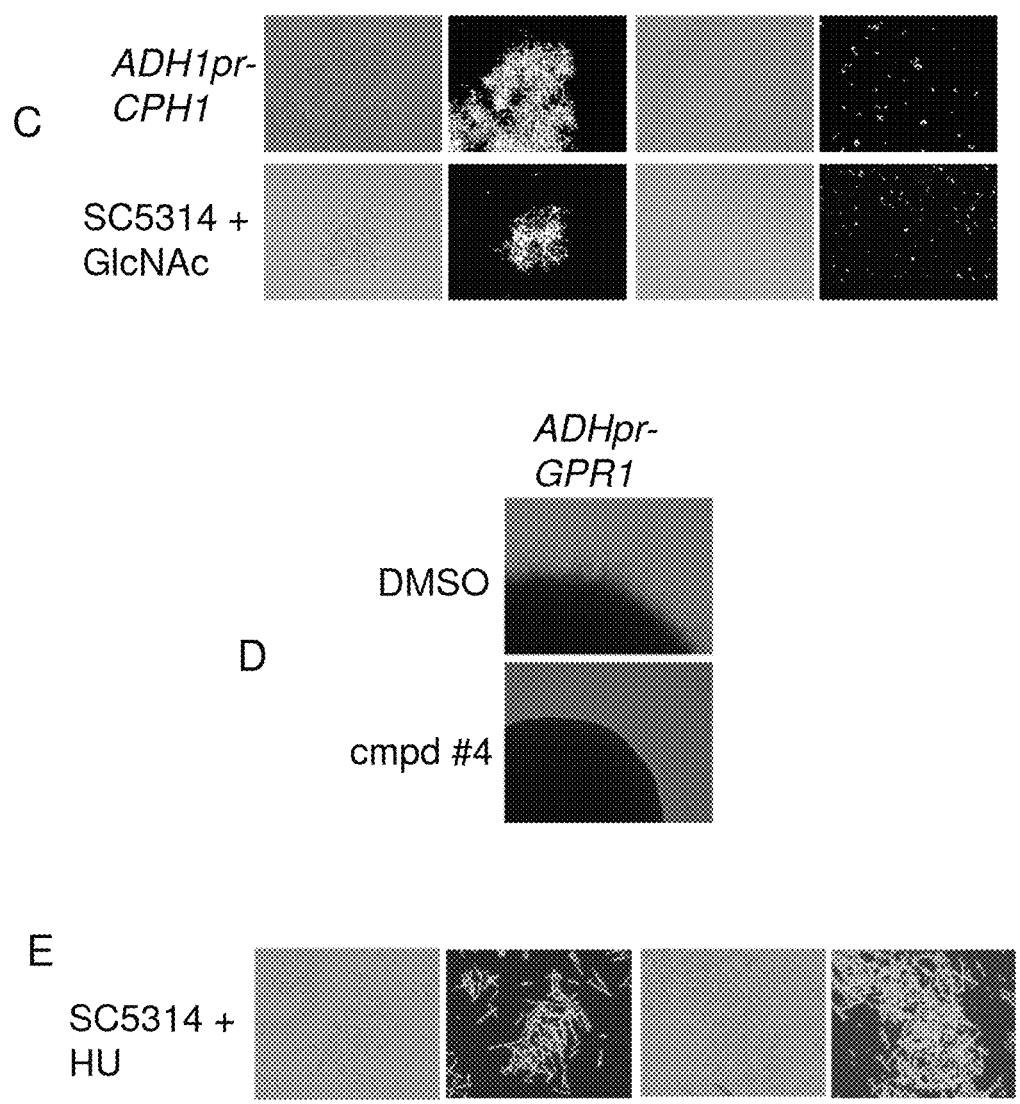

To explore the mechanism of compound #4 action, we tested whether compound #4 would alter hyphal induction in mutants that hyperactivate the filamentation process. For example, hyphal induction by Spider media requires the cyclic AMP-protein kinase A (cAMP-PKA) pathway; FIG. 30A. Stimulation of this pathway drives PKA to phosphorylate transcription factor Efg1, activating Efg1 to increase expression of genes required for hyphal morphogenesis. We confirmed that cells with a hyperactive Ras1 signaling protein (ras1-G13V; (34)), or an overexpressed, constitutively active G-alpha subunit that acts upstream of Efg1 (gpa2-Q355L) (35), or a constitutively expressed Efg1 transcription factor with a phosphomimetic mutation that simulates constitutive PKA signaling (PCKpr-efg1-T206E; (Bockmuhl and Ernst, *Genetics* 157:1523, 2011) indeed were all hyperfilamentous compared to wild-type cells in Spider media (FIG. 30B). However, in the presence of compound #4, cells from all these mutant strains retained a planktonic, budded morphology (FIG. 30B). Likewise, cells constitutively overexpressing the G protein-coupled receptor Gpr1 become hyperfilamentous on solid Spider media via the PKA pathway, and we observed that compound #4 blocked hyphal morphogenesis in these cells as well (FIG. 30C). On their own, these data would be consistent with compound #4 acting downstream of transcription factor Efg1 (FIG. 30A).

However, other experiments suggested that compound #4 affects more than one signaling pathway. For example, the modified sugar N-acetyl-glucosamine (GlcNac) also stimulates hyphal morphogenesis, but does so independently of the cAMP-PKA pathway, instead activating the transcription factor Cph1. Upon testing morphogenesis driven by GlcNac-containing media or constitutive overexpression of Cph1, we found that compound #4 also inhibits formation of hyphae in these cases (FIG. 30D). These data indicate that compound #4 may affect multiple signaling pathways, or could act by destroying the cell's ability to form elongated structures regardless of the inducing signal.

In addition to nutrient-mediated signals, genotoxic stress promotes hyphal morphogenesis in *C. albicans*, and the DNA damage signaling kinase Rad53 is required for the hyphal transition. In contrast to the above studies, cells treated with the DNA replication inhibitor hydroxyurea (HU) form hyphae regardless of the presence of compound #4 (FIG. 30E). Together, these data suggest that compound #4 is not incompatible with hyphal morphogenesis per se, but blocks multiple signaling mechanisms that promote it.

Other Embodiments

All publications, patents, and patent applications mentioned in the above specification are hereby incorporated by reference. Various modifications and variations of the described methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A method of treating a microbial infection comprising administering to a subject in need thereof a composition comprising a compound, or a salt thereof, wherein the compound comprises a structure selected from the following:

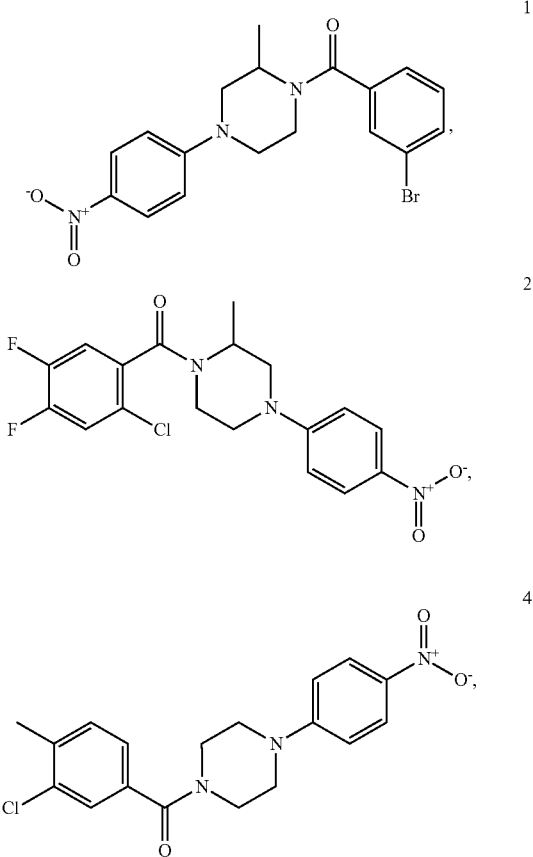

-continued

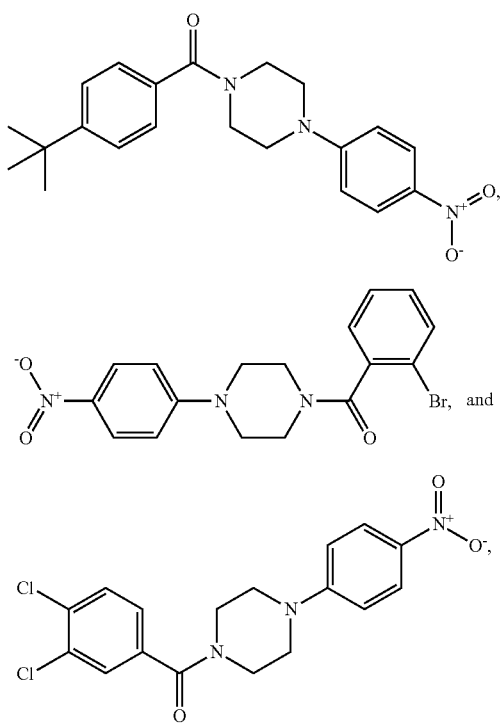
5

6 wherein, optionally, said composition comprises a pharmaceutically acceptable carrier.

2. The method of claim 1, wherein said microbial infection is a fungal, bacterial, yeast, or mold infection.

3. The method of claim 2, wherein said fungal infection is caused by a *Candida* spp.

4. The method of claim 1, wherein said subject is a human.

5. A composition comprising an anti-microbial compound, or a salt thereof, said compound comprising: a structure selected from the group consisting of:

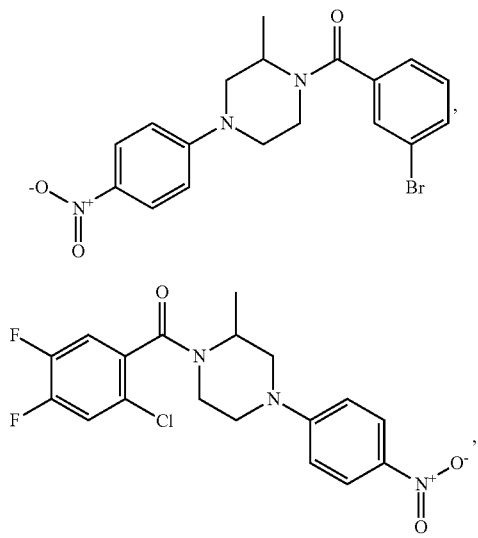
1

2

-continued

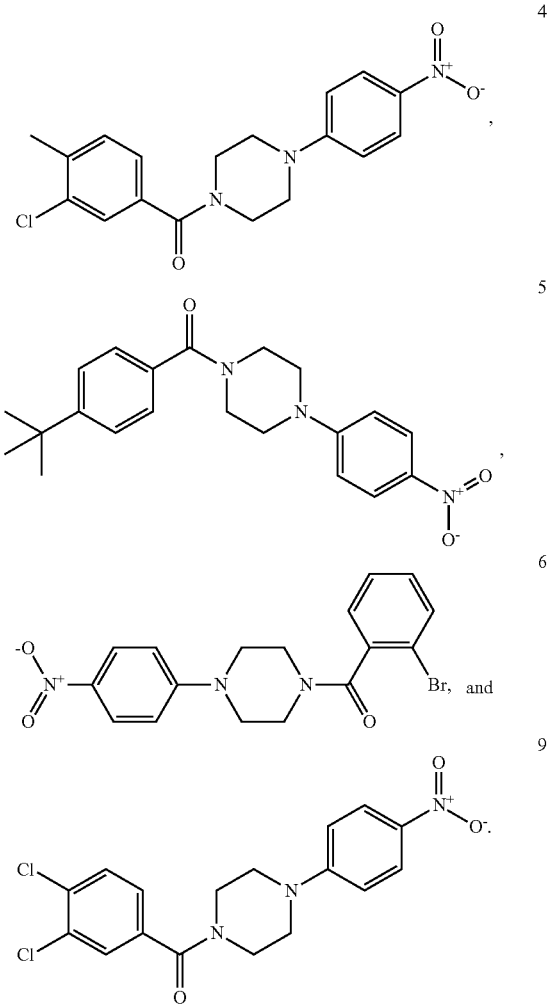
4

5

6

9

6. An article comprising the composition of claim 5 incorporated therein or coated thereto, wherein said article:
   a) is a medical device, a cuff, a dressing material, a mesh, a hernia patch, a wound dressing, a bandage, a syringe, gloves, or a household product, a cosmetic product, a pharmaceutical product, a washing or cleaning formulation, a medical device surface, a medical device material, a fabric, a plastic, a surface of a plastic article, a paper, a nonwoven material, a wood, leather, or a metal surface; or
   b) comprises a thermoset, thermoplastic, elastomeric, or crosslinked polymer.

7. The article of claim 6, wherein said medical device is a cardiac-assist device, an artificial heart valve, a catheter, a central line, an intravenous (IV) line, a joint, a stent, a prosthetic implant, a pacemaker, a conduit, a cannula, an appliance, a scaffold, an artificial sphincter, a pessary, a tube, a drain, a trochar or plug, an implant, a rod, a screw, an orthopedic or implantable prosthetic device or appliance, a suture, a drug delivery device, an oral implant, a denture, or a brace.

8. The composition of claim 5, wherein said anti-microbial compound reduces or inhibits at least one function of a microbial agent.

9. The composition of claim 8, wherein said at least one function is adhesion, yeast-to-hyphal morphological transition, biofilm formation, or growth.

10. The composition of claim 8, wherein said microbial agent is a fungus, bacteria, yeast, or mold.

11. The article of claim 6, wherein said polymer is selected from a polyolefin, polyamide, polyurethane, polyacrylate, polyacrylamide, polycarbonate, polystyrene, polyvinyl acetates, polyvinyl alcohol, polyester, halogenated vinyl polymer, a natural or synthetic rubber, an alkyd resin, an epoxy resin, an unsaturated polyester, an unsaturated polyamide, a polyimide, a silicone, a carbamate containing polymer, a fluorinated polymer, a crosslinkable acrylic resin, an epoxy acrylate, a urethane acrylate, or a polyester acrylate, or a block co-polymer thereof.

12. A method for achieving an antimicrobial, preservative, and/or microorganism adhesion inhibiting effect for the protection within an article and/or material or on the surface of an article and/or material, which method comprises applying the composition of claim 5 or an adduct or salt thereof to said article and/or material.

13. The method of claim 12, wherein said article and/or material:
a) is a medical device, a cuff, a dressing material, a mesh, a hernia patch, a wound dressing, a bandage, a syringe, gloves, a household product, a cosmetic product, a pharmaceutical product, a washing or cleaning formulation, a medical device surface, a medical device material, a fabric, a plastic, a surface of a plastic article, a paper, a nonwoven material, a wood, leather, or a metal surface; or
b) comprises a thermoset, thermoplastic, elastomeric, or crosslinked polymer.

14. The method of claim 13, wherein said medical device is a cardiac-assist device, an artificial heart valve, a catheter, a central line, an intravenous (IV) line, a joint, a stent, a prosthetic implant, a pacemaker, a conduit, a cannula, an appliance, a scaffold, an artificial sphincter, a pessary, a tube, a drain, a trochar or plug, an implant, a rod, a screw, an orthopedic or implantable prosthetic device or appliance, a suture, a drug delivery device, an oral implant, a denture, or a brace.

15. The method of claim 12, wherein said compound reduces or inhibits at least one function of a microbial agent.

16. The method of claim 15, wherein said at least one function is adhesion, yeast-to-hyphal morphological transition, biofilm formation, or growth.

17. The method of claim 15, wherein said composition inhibits or reduces adhesion or biofilm formation by a fungus, wherein said fungus is a *Candida* spp.

18. The method of claim 13, wherein said polymer is selected from a polyolefin, polyamide, polyurethane, polyacrylate, polyacrylamide, polycarbonate, polystyrene, polyvinyl acetates, polyvinyl alcohol, polyester, halogenated vinyl polymer, a natural or synthetic rubber, an alkyd resin, an epoxy resin, an unsaturated polyester, an unsaturated polyamide, a polyimide, a silicone, a carbamate containing polymer, a fluorinated polymer, a crosslinkable acrylic resin, an epoxy acrylate, a urethane acrylate, or a polyester acrylate, or a block co-polymer thereof.

19. The composition of claim 5, wherein said compound is

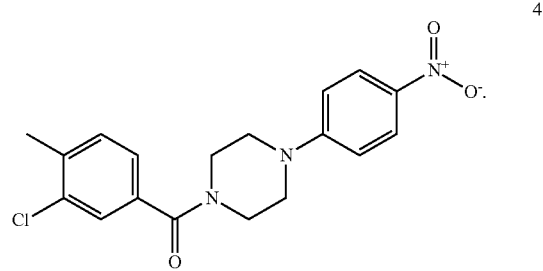

20. The article of claim 11, wherein said crosslinkable acrylic resin is a substituted acrylic ester.

21. The article of claim 11, wherein said halogenated vinyl polymer is polyvinyl chloride (PVC).

22. The method of claim 18, wherein said crosslinkable acrylic resin is a substituted acrylic ester.

23. The method of claim 18, wherein said halogenated vinyl polymer is polyvinyl chloride (PVC).

24. The method of claim 1, wherein the composition comprises the following compound:

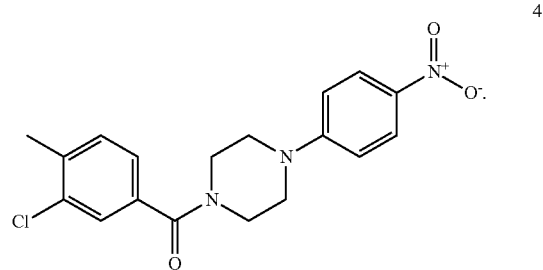

* * * * *

UNITED STATES PATENT AND TRADEMARK OFFICE
CERTIFICATE OF CORRECTION

PATENT NO. : 9,648,880 B2
APPLICATION NO. : 14/017914
DATED : May 16, 2017
INVENTOR(S) : Paul Kaufman et al.

It is certified that error appears in the above-identified patent and that said Letters Patent is hereby corrected as shown below:

In the Specification

Column 1 Lines 7-10 after the title, replace:
"STATEMENT OF FEDERALLY SPONSORED RESEARCH
This invention was made with government support under grant number R01 GM055712, R21 NS066432, F31 AI078726, and P30 AI42845-14 awarded by the NIH. The government has certain rights in this invention."

With:
--STATEMENT OF FEDERALLY SPONSORED RESEARCH
This invention was made with government support under grant nos. GM055712, NS066432, AI078726, and AI042845 awarded by the National Institutes of Health. The government has certain rights in this invention.--

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*